United States Patent
Park et al.

(10) Patent No.: US 11,426,441 B2
(45) Date of Patent: Aug. 30, 2022

(54) COMPOSITION COMPRISING PROTEIN PHOSPHATASE 1 INHIBITORY PEPTIDE FOR TREATING VASCULAR DISEASES

(71) Applicant: BethphaGen Inc., Gwangju (KR)

(72) Inventors: Woo Jin Park, Seoul (KR); Seung Pil Jang, Seoul (KR)

(73) Assignee: BethphaGen Inc., Gwangju (KR)

( * ) Notice: Subject to any disclaimer, the term of this patent is extended or adjusted under 35 U.S.C. 154(b) by 0 days.

(21) Appl. No.: 16/344,467

(22) PCT Filed: Oct. 24, 2017

(86) PCT No.: PCT/KR2017/011796
§ 371 (c)(1),
(2) Date: Apr. 24, 2019

(87) PCT Pub. No.: WO2018/080146
PCT Pub. Date: May 3, 2018

(65) Prior Publication Data
US 2019/0328823 A1 Oct. 31, 2019

(30) Foreign Application Priority Data
Oct. 24, 2016 (KR) .................. 10-2016-0138612

(51) Int. Cl.
*A61K 38/08* (2019.01)
*A61P 9/12* (2006.01)
*A23L 33/18* (2016.01)

(52) U.S. Cl.
CPC .............. *A61K 38/08* (2013.01); *A23L 33/18* (2016.08); *A61P 9/12* (2018.01); *A23V 2002/00* (2013.01)

(58) Field of Classification Search
CPC ...... A61K 38/005; A61K 38/08; C07K 14/00; C07K 14/47; C07K 14/4703; C07K 7/00; C07K 7/06; A23L 33/18; A61P 9/12
See application file for complete search history.

(56) References Cited

U.S. PATENT DOCUMENTS
2004/0214760 A1  10/2004  Gupta et al.

FOREIGN PATENT DOCUMENTS
| KR | 10-2014-0010889 A | 1/2014 |
| WO | WO-200025804 A2 | 5/2000 |
| WO | WO-03/004692 A2 | 1/2003 |
| WO | WO-2014007584 A1 * | 1/2014 |

OTHER PUBLICATIONS https://vascularcures.org/what-is-vascular-disease/, Vascular Diseases—Vascular Cures, accessed on Oct. 11, 2019.*
Persoulla Nicolaou, Role of protein phosphatase-1 inhibitor-1 in cardiac physiology and pathophysiology , J Mol Cell Cardiol. Sep. 2009 ; 47(3): 365-371.*
Bradley A. Maron, Emerging Concepts in the Molecular Basis of Pulmonary Arterial Hypertension (PAH): Part II: Neurohormonal Signaling Contributes to the Pulmonary Vascular and Right Ventricular Pathophenotype of PAH , Circulation. Jun. 9, 2015; 131(23): 2079-2091.*
Genscript, Transportan, https://www.genscript.com/peptide/RP20512-Transportan.html, accessed on Dec. 17, 2021.*
Kim, H.Y. et al. Discovery of a non-cationic cell penetrating peptide derived from membrane-interacting human proteins and its potential as a protein delivery carrier. Sci. Rep. 5, 11719; doi: 10.1038/srep11719 (2015).*
Uniprot Protein Database, UniProtKB-P22466 (GALA_HUMAN), accessed on Dec. 17, 2021.*
Eto, Masumi et al., "Regulation of cellular protein phosphatase-1 (PP1) by phosphorylation of the CPI-17 family, C-kinase-activated PP1 inhibitors", Journal of Biological Chemistry, 2009.
Nicolaou, Persoulla et al., "Role of protein phosphatase-1 inhibitor-1 in cardiac physiology and pathophysiology", Journal of Molecular and Cellular Cardiology, 2009.
Jang, Seung Pil et al., "A decoy peptide targeted to protein phosphatase 1 1-18,20 attenuates degradation of SERCA2a in vascular smooth muscle cells", PloS One, 2016.10.28.
Larissa Lipskaia et al., "Synergistic Role of Protein Phosphatase Inhibitor 1 and Sarco/Endoplasmic Reticulum Ca2+-ATPase in the Acquisition of the Contractile Phenotype of Arterial Smooth Muscle Cells", Circulation, vol. 129, pp. 773-785(2014).
Jae Gyun Oh et al., "Decoy peptides targeted to protein phosphatase 1 inhibit dephosphorylation of phospholamban in cardiomyocytes", Journal of Molecular and Cellular Cardiology, vol. 56, pp. 63-71 (2013).
International Search Report from corresponding PCT Application No. PCT/KR2017/011796, dated Feb. 27, 2018.
European Search Report issued to the corresponding European Patent Application No. 17863591.8, dated Oct. 2, 2019.

* cited by examiner

*Primary Examiner* — Julie Ha
*Assistant Examiner* — Erinne R Dabkowski
(74) *Attorney, Agent, or Firm* — Harness, Dickey & Pierce, P.L.C.

(57) ABSTRACT

The present invention relates to a composition comprising a protein phosphatase 1 inhibitory peptide for treating vascular diseases. The composition of the present invention inhibits protein phosphatase 1 (PP1)-mediated dephosphorylation to suppress abnormal proliferation of vascular smooth muscle cells (VSMCs), and activates eNOS of vascular endothelial cells (VECs) to induce the recovery from dysfunction, and thus can be favorably used in the treatment of vascular diseases including pulmonary hypertension.

5 Claims, 40 Drawing Sheets
Specification includes a Sequence Listing.

|  | Sham (n = 3) | MCT + Saline (n = 5) | MCT + ΨPLB-SE (n = 6) |
|---|---|---|---|
| RVESP (mmHg) | 33.7 ± 1.7 | 67.4 ± 6.4* | 33.5 ± 5.8 |
| RVEDP (mmHg) | 5.9 ± 2.7 | 2.9 ± 2.2 | 3.7 ± 2.7 |
| LVESP (mmHg) | 122.9 ± 19.7 | 104.3 ± 16.5 | 105.6 ± 13.1 |
| LVEDP (mmHg) | 7.9 ± 1.6 | 5.4 ± 1.8 | 6.1 ± 2.6 |
| CO (ml/min) | 41.5 ± 2.1 | 39.4 ± 11.3* | 47.9 ± 11.9 |

… # COMPOSITION COMPRISING PROTEIN PHOSPHATASE 1 INHIBITORY PEPTIDE FOR TREATING VASCULAR DISEASES

CROSS-REFERENCE TO RELATED APPLICATIONS

This application is a national phase application of PCT Application No. PCT/KR2017/011796, filed on Oct. 24, 2017, which claims priority to Korean Patent Application No. 10-2016-0138612, filed on Oct. 24, 2016. The entire disclosures of the applications identified in this paragraph are incorporated herein by reference.

FIELD

The present invention was made with the support of the Ministry of Science, ICT, and Future Planning of the Republic of Korea, under Project No. GF01330, which was conducted under the research subject named "Global Research Lab" within the research project entitled "Analysis of signal transduction of cardiac disorders and gene therapy" by Gwangju Institute of Science and Technology under the management of the National Research Foundation of Korea, from 1 Apr. 2013 to 31 Mar. 2014.

The present invention relates to a composition containing a protein phosphatase 1 inhibitory peptide for treatment of vascular diseases.

BACKGROUND

Vascular remodeling is a phenomenon induced by various diseases, such as pulmonary arterial hypertension and coronary artery restenosis arteriosclerosis, and proceeds by vascular injury or stimulation [Pasterkamp G et al. (2000) Cardiovasc Res 45(4): 843-852]. Such a phenomenon causing vascular structural changes results from cell proliferation, death, dysfunction, and the like. Out of vascular constituents, vascular endothelial cells (VECs) and vascular smooth muscle cells (VSMCs) are decisive mediators responding to injury and stimulation and lead vascular remodeling [Rabinovitch M et al. (2012) J Clin Invest 122(12): 4306-4313]. The interaction between VSMCs and VECs and respective roles thereof are important in maintaining vascular homeostasis, such as vascular tension/relaxation. In pathological conditions where such roles were abnormally taken, the dysfunction of VECs, abnormal proliferation of VSMCs, and the like occur. As described above, extracellular matrix changes occurring by fibrosis cells existing on arterial adventitia in addition to an endothelial phenotype showing contractile characteristics due to abnormal proliferation accelerate vascular fibrosis, and as a result, arterial stiffness is further increased, leading to a phenotype of hypertension [Harvey A et al. (2016) Can J Cardiol 32(5): 659-668; Michell G F (2014) Hypertension 64(1):13-18].

The abnormal proliferation of VSMCs is a fundamental cause of vascular proliferative diseases, such as the above-mentioned pulmonary arterial hypertension or aortic restenosis [Dzau V J et al. (2002) Nature med 8:1249-1256; Novak K et al. (1998) Nature Med 4: 989-990]. The damage to arterial walls induces the migration of VSMCs to an intimal layer, thereby rapidly changing the phenotype from contraction and arrest, resulting in synthesis and proliferation. The abnormal proliferation of VSMCs having a synthetic phenotype causes an expansion of the artery intima, which is a phenomenon called neointimal growth [Austin G E et al. (1985) J Am Coll Cardiol 6: 369-375; Hanke H et al. (1992) Herz 12: 300-308]. In pulmonary arterial hypertension (PAH), a vasodilator substance, such as nitric oxide (NO) or prostacyclin (PGI2), inhibiting VSMC proliferation are reduced, and the abnormal proliferation of VSMCs is caused according to an effect of a vasohypertonic substance, such as endothelin-1 [Hoeper M M et al. (2000) Engl J Med 342: 1866-1870; Giaid A et al. (1993) N Engl J Med 328: 1732-1739]. Therefore, the regulation of VMSC proliferation is an important factor in the treatment for vascular proliferative diseases.

The proliferation of VSMCs is related with an chronic increase in the cytosolic $Ca^{2+}$ level, and this is caused by the loss of $Ca^{2+}$ handling proteins, such as ryanodine receptors and sarco/endoplasmic reticulum (SR) $Ca^{2+}$-ATPase (SERCA2a) [Vallot O et al. (2000) Aerterioscler Thromb Vasc Biol 20: 1225-1235]. The gene transfer-mediated restoration of SERCA2a attenuates VSMC proliferation and neointimal formation [Lipskaia L et al. (2005) Circ Res 97: 488-495; Lipskaia L et al. (2013) Gene Ther 20: 396-406]. Therefore, the maintenance of a low cytosolic $Ca^{2+}$ level by regulating SERCA2a activity may be a reasonable strategy to prevent and relieve VSMC proliferation.

SERCA2a activity is inhibited by a direct interaction with phospholamban (PLB). The inhibitory activity thereof is enhanced by dephosphorylation at Ser16 or Thr17 by protein phosphatase 1 (PP1) [Steenaart N A et al. (1992) Arch Biochem Biophys 293: 17-24; Mattiazzi A et al. (2005) Cardiovasc Res 68: 366-375; Schwinger R H et al. (1999) J Mol Cell Cardiol 31: 479-491; Sande J B et al. (2002) Cardiovasc Res 53: 382-391]. Therefore, the inhibition of the PP1-mediated dephosphorylation of PLB is a reasonable approach to upregulate SERCA2a activity in failing hearts. The present inventors previously reported that a 9-mer peptide, ψPLB-SE, mimics phosphorylated PLB, and thus functions as a decoy for PP1 [Oh J G et al. (2013) J Mol Cell Cardiol 56: 63-71]. This peptide restored SERCA2a activity in the heart after ischemia/reperfusion by inhibiting the dephosphorylation of PLB in vitro and ex vivo.

Meanwhile, the meaning of VECs is merely an anatomical barrier in vascular proliferation-related cardiovascular diseases. VECs correspond to an important organ that secretes substances for maintaining vascular homeostasis. The occurrence of various cardiovascular diseases and VEC functions are closely related, and VECs play an important role in the development and progression of arteriosclerosis causing, especially, hypertension. The endothelial dysfunction of VECs is known to be an important cause of pulmonary arterial hypertension, and actually, NO and prostacyclin among several substances secreted by VECs act as vascular relaxants, and suppress platelet aggregation and inhibit VSMC proliferation, which are important processes for inhibiting the progression of arteriosclerotic diseases, such as pulmonary arterial hypertension [Giaid A et al. (1995) N Engl J Med 333: 214-221; Christman B W et al. (1992) N Engl J Med 327: 70-75].

The reduction of vascular relaxants in pulmonary arterial hypertension patients is commonly reported, and cyclic guanosine monophosphate (cGMP), which is a product of guanylate cyclase (GC) activated by NO, is hydrolyzed by the activation of phosphodiesterase-5 (PDE-5). The cGMP functions to inhibit vasodilation and cell proliferation, and PDE-5 activity reduce the duration of cGMP action. In this context, sildenafil, tadalafil, and the like, as PDE-5 inhibitors, have now been developed. However, it is known that in pulmonary arterial hypertension, PDE-5 activity is increased as well as the ability to produce NO in VECs is lost, and thus the cGMP level is also fundamentally reduced, and therefore, the inhibition of PDE-5 activity has limits. In fact, recent clinical results have raised the risk of long-term use [Siehr S L et al. (2015) Front Pediatr 3: 12]. Therefore, eNOS-expressing stem cell therapy and GC activators for increasing NO production are basically passing through clinical trial phases [Wei L et al. (2013) Hypertens Res 36(5): 414-421; Granton J et al (2015) Circ Res 117(7): 645-654].

Meanwhile, 70-80% of pulmonary arterial hypertension patients with family history are reported to have a mutation in the bone morphogenetic protein receptor 2 (BMPR2) gene, and the BMPR2 reduction is shown to increase the production of inflammation-related cytokines, such as granulocyte macrophage colony-stimulating factor (GM-CSF), IL-6, and IL-8, in VECs. In particular, the translation of GM-CSF is increased due to activation of eukaryotic translation initiation factor (eIF2α) [Sawada H et al (2014) J Exp Med 211(2): 263-280]. Studies on gene therapy using the BMPR2 gene are currently being actively conducted at the pre-clinical phase, and FK506 (tacrolimus), which is a BMPR2 signaling system activator, is in the clinical trial phase for PAH patients [Spiekerkoetter E et al. (2009) Circ Res 105: 639-647; Spiekerkoetter E et al (2013) Respir Crit Care Med 192: 254-257].

Cell permeable peptide (CPP), which is a kind of signal peptide, is a peptide used for the purpose of penetrating a polymer substance into cells. CCP is composed of about 7-30 sequences, and related research has been carried out in earnest, starting with research of TAT derived from HIV. Antennapedia derived from *Drosophila*, VP22 derived from HSV-1 virus, are pep-1 derived from SV40 large antigen T are first-generation CPPs, and peptides in which arginine and lysine are continuously linked, has been reported to also have cell penetration. However, these CPPs are not sequences derived from human proteins, and thus have a risk of cytotoxicity and immunogenicity. Moreover, recent clinical trial results of CCP-bound biomedicine candidates showed that the delivery efficacy of such candidates to human cells was degraded or the effects of cargos were difficult to investigate. As a result, studies on CPPs derived from human proteins, such as Hph-1, LPIN3, and dNP2, having improved delivery efficiency to human cells, have been conducted [Jung M R et al. (2011) J Control Relase 152(2): 294-302; Lim S et al. (2012) Mol Cells 34(6) 577-582; Lim S et al. (2016) PLos One 11(5):e0155689; Lim S et al. (2015) Nat Commun 6:8244].

Throughout the present specification, many papers and patent documents are used as references, and the citations thereof are represented. The disclosure of the cited papers and patent documents is incorporated in the present specification by reference in its entirety to describe the level of the technical field to which the present invention pertains and the content of the present invention more clearly.

SUMMARY

Technical Problem

The present inventors have made research efforts to develop novel peptide medicines for vascular diseases, capable of regulating abnormal proliferation of vascular smooth muscle cells (VSMCs). As a result, the present inventors, ψPLB-SE, which is a peptide targeting protein phosphatase 1 (PP1), balloon-injured rat carotid arteries, The present inventors have made research efforts to develop novel peptide medicines for vascular diseases, capable of regulating abnormal proliferation of vascular smooth muscle cells (VSMCs). As a result, the present inventors found that ψPLB-SE, which is a peptide targeting protein phosphatase 1 (PP1), attenuated neointimal growth in balloon-injured rat carotid arteries, and also confirmed that ψPLB-SE regulates the abnormal $Ca^{2+}$ level by activating SERCA2a, thereby protecting SERCA2a from calpain-dependent degradation in vascular smooth muscle cells (VSMCs). Furthermore, the present inventors found a novel mechanism in which the dysfunction of VECs is restored by increasing endothelial nitric oxide synthase (eNOS) activity of VECs, thereby mitigating pulmonary arterial hypertension. The present inventors confirmed from the above effects that ψPLB-SE can form a basis of therapy strategy for vascular proliferative diseases, and thus completed the present invention.

Accordingly, an aspect of the present invention is to provide a pharmaceutical composition for treatment of vascular diseases.

Another aspect of the present invention is to provide a food composition for mitigation or alleviation of vascular diseases.

Still another aspect of the present invention is to provide a method for treatment of vascular diseases.

Still another aspect of the present invention is to provide a pharmaceutical composition for use in the treatment of vascular diseases.

Other purposes and advantages of the present disclosure will become more obvious when taken with the following detailed description of the invention, claims, and drawings.

Technical Solution

In accordance with an aspect of the present invention, there is provided a pharmaceutical composition for treatment of vascular diseases, the composition containing: (a) a pharmaceutically effective amount of a protein phosphatase 1 inhibitory peptide; and (b) a pharmaceutically acceptable carrier.

The present inventors have made research efforts to develop novel peptide medicines for vascular diseases, capable of regulating abnormal proliferation of vascular smooth muscle cells (VSMCs). As a result, the present inventors found that ψPLB-SE, which is a peptide targeting protein phosphatase 1 (PP1), attenuated neointimal growth in balloon-injured rat carotid arteries, and also confirmed that ψPLB-SE regulates the abnormal $Ca^{2+}$ level by activating SERCA2a, thereby protecting SERCA2a from calpain-dependent degradation in vascular smooth muscle cells (VSMCs). Furthermore, the present inventors found a novel mechanism in which the dysfunction of VECs is restored by increasing endothelial nitric oxide synthase (eNOS) activity of VECs, thereby mitigating pulmonary arterial hypertension. The present inventors confirmed from the above effects that ψPLB-SE can form a basis of therapy strategy for vascular proliferative diseases, and thus completed the present invention.

The protein phosphatase 1 inhibitory peptide of the present invention is a mimic peptide in which the phosphorylated serine 16th amino acid residue serine (Ser) is substituted with glutamic acid (Glu) or aspartic acid (Asp) in a phosphorylated form of phospholamban (amino acid sequence of SEQ ID NO: 1), and acts as a substrate mimetic inhibitor to protein phosphatase 1. A serine residue binds with a polar phosphate group to be negatively charged, and the present invention employed a phosphorylated serine substitution model by using characteristics in which such the phosphorylated serine has structural and electric similarity to negatively charged glutamic acid and aspartic acid among amino acids. In general, when the dephosphorylation of an amino acid occurs after the protein phosphate 1 inhibitory peptide binds to an active site of protein phosphatase 1 (PP1), a substrate and an enzyme are separated into each other. However, the peptide of the present invention is not separated (irreversible) from an active site of the PP1 enzyme, and thus the peptide of the present invention is expected to show a strong inhibitory effect.

That is, the "protein phosphatase 1 inhibitory peptide" of the present invention is a peptide designed to include a peptide sequence that mimics a linkage loop of phosphorylated PLB, and can block PP1 action more strongly compared with a peptide including phosphorylated serine.

The present invention shows that the protein phosphatase 1 inhibitory peptide "ψPLB-SE" can inhibit neointimal growth in restenosis, which is a vascular proliferative disease, and can also mitigate symptoms of pulmonary arterial hypertension. The abnormal proliferation of VSMCs and the dysfunction of VECs, which have been reported as phenotypes of disease, are solved by ψPLB-SE through respective characteristic mechanisms thereof.

The first mechanism shows that ψPLB-SE attenuates neointimal growth in rat carotid arteries by inhibiting the degradation of SERCA2a in VSMCs. Under pathological conditions, the increased cytosolic $Ca^{2+}$ level induces the activation of calpain that is in turn responsible for the degradation of SERCA2a, which sequentially increases the cytosolic $Ca^{2+}$ level. According to the present invention, ψPLB-SE inhibits a vicious circle of $Ca^{2+}$ level increase and SERCA2a level decrease.

The neointimal growth in the injured vasculature is largely facilitated by the proliferation of vascular smooth muscle cells (VSMCs), which associates with sarco/endoplasmic reticulum $Ca^{2+}$-ATPase (SERCA2a) activity. The gene transfer-mediated restoration of the SERCA2a level attenuates neointimal growth and VSMC proliferation. The present inventors previously reported that a peptide targeted to protein phosphatase 1, that is, ψPLB-SE, normalizes SERCA2a activity in cardiomyocytes. The present inventors found that ψPLB-SE attenuated neointimal growth in balloon-injured rat carotid arteries, and also found the proliferation and migration of VSMCs cultured in high-serum media (synthetic conditions).

Simultaneously, ψPLB-SE inhibited the degradation of SERCA2a in the injured carotid arteries and VSMCs under synthetic conditions. The calpain inhibitor MDL28170 also attenuated SERCA2a degradation and VSMC proliferation under synthetic conditions, indicating that calpain degrades SERCA2a. The $Ca^{2+}$ ionophore A23187 induced SERCA2a degradation in VSMCs, which was blocked by either ψPLB-SE or MDL28170. Additionally, ψPLB-SE normalized the cytosolic $Ca^{2+}$ level in VSMCs that was increased by either A23187 or synthetic stimulation. Collectively, these data indicate that ψPLB-SE regulates the abnormal $Ca^{2+}$ handling by activating SERCA2a, which further protects SERCA2a from calpain-dependent degradation in VSMCs. The abnormal proliferation of VSMCs in pulmonary arterial hypertension can also be corrected through the same mechanism, which was proved by verifying the phosphorylation of the 16th serine residue in phospholamban and measuring the activity of SERCA2a, and confirmed through expression and proliferation assay tests of cell proliferation representative proteins that the proliferation of pulmonary artery smooth muscle cells is actually inhibited.

In addition, a novel mechanism shows that the dysfunction of VECs was restored by enhancing endothelial nitric oxide synthase (eNOS) activity of VECs, thereby mitigating pulmonary arterial hypertension. It was proved that ψPLB-SE attenuated characteristic phenotypes, vascular thickening, fibrosis of vascular adventitial tissues, and inflammation, in monocrotaline (MCT)-induced pulmonary arterial hypertension rats and mice. It was also confirmed that the ψPLB-SE treatment restores not only the phosphorylation of eNOS, but also the expression of BMPR2 and the phosphorylation level of eIF2α associated with a mechanism of inflammation in pulmonary tissue of pulmonary arterial hypertension animal models.

To establish a new mechanism in VECs, the interactions of PP1 with eNOS and, a known high-order substance, Akt, were investigated, and through this, it was confirmed that PP1 has a direct interaction with Akt but not eNOS and PP1 action was inhibited by ψPLB-SE. Also, in order to investigate whether the increased phosphorylation of Akt and eNOS due to the treatment with ψPLB-SE can be actually regulated by PP1 inhibition, it was confirmed that the phosphorylation by the treatment with LY294002, an inhibitor of PI3K, which is a high-order kinase of Akt, was offset and the Akt-eNOS phosphorylation was increased by the treatment with ψPLB-SE. In addition, it was confirmed that the increase effect of eNOS phosphorylation by ψPLB-SE was offset after the treatment with Inhibitor IV, an Akt inhibitor. Such an increase of eNOS activity by ψPLB-SE could also be confirmed through animal tissue experiments using an induction of pulmonary arterial hypertension with MCT.

In addition, experiments to investigate the cell penetrating effect of CPP were carried out, and it was verified that various forms of cell penetrating peptides can obtain the same effect on ψPLB-SE through cell penetrating peptide (CPP) comparison experiments. The present inventors concluded through these effects that ψPLB-SE can form a basis of therapy strategy for vascular proliferative diseases.

The protein phosphatase 1 inhibitory peptide of the present invention may be a mimic peptide including a sequence of the 14th to 22nd amino acids in the amino acid sequence of SEQ ID NO: 1, and composed of an amino acid sequence in which the phosphorylated serine residue as the 16th amino acid residue is substituted with glutamic acid (Glu) or aspartic acid (Asp). More specifically, in the protein phosphatase 1 inhibitory peptide of the present invention, the 16th amino acid sequence is not serine or phosphorylated serine.

According to an embodiment of the present invention, the protein phosphatase 1 inhibitory peptide may be selected from the group consisting of amino acid sequences of SEQ ID NO: 2 to SEQ ID NO: 6. According to another embodiment of the present invention, the protein phosphatase 1 inhibitory peptide may be composed of the amino acid sequence of SEQ ID NO: 1 or SEQ ID NO: 3. The protein phosphatase 1 inhibitory peptides of SEQ ID NO: 2 to SEQ ID NO: 6 are described in detail in Korean Patent No. 10-1516791.

A protein phosphatase 1 inhibitory peptide used in an embodiment of the present invention may be produced by substituting the phosphorylated serine residue with glutamic acid (Glu) or aspartic acid (Asp) in "Arg-Ala-Ser (P)-Glu-Ile-Glu-Met-Pro-Gln".

SEQ ID NO: 2 to SEQ ID NO: 6 above are as follows. The underlined parts represent amino acid sites substituted with glutamic acid or aspartic acid.

SEQ ID NO: 2: Arg-Ala-Glu-Thr-Ile-Glu-Met-Pro-Gln.

SEQ ID NO: 4: Arg-Ala-Asp-Thr-Ile-Glu-Met-Pro-Gln.

-continued

SEQ ID NO: 4: Ala-Glu-Thr-Ile-Glu-Met-Pro-Gln.

SEQ ID NO: 5: Arg-Ala-Glu-Thr-Ile-Glu-Met.

SEQ ID NO: 6: Arg-Ala-Glu-Thr-Ile-Glu.

According to the present invention, the protein phosphatase 1 inhibitory peptide may be composed of an amino acid sequence represented by General Formula I:

$$X_1\text{-Ala-}X_2\text{-}X_3\text{-Ile-Glu-}X_4 \tag{I}$$

wherein $X_1$ represents 0-20 amino acid residues; $X_2$ represents Glu or Asp; $X_3$ represents Thr, Glu, or Asp; and $X_4$ represents 0-30 amino acid residues.

According to an embodiment of the present invention, wherein in General Formula 1, $X_1$ represents 0-20, 0-20, 0-3, or 0-1 amino acid residue. According to an embodiment of the present invention, wherein in General Formula 1, $X_4$ represents 0-30, 0-20, 0-10, or 0-3 amino acid residues.

According to another embodiment of the present invention, $X_1$ represents 0-20 amino acid residues; and $X_4$ represents 0-20 amino acid residues.

According to another embodiment of the present invention, $X_1$ represents 0-1 amino acid residue; and $X_4$ represents 0-3 amino acid residues. According to a particular embodiment of the present invention, $X_1$ is Arg. According to another particular embodiment of the present invention, $X_4$ is Met, Met-Pro, or Met-Pro-Gin.

The amino acid sequence represented by General Formula I may be selected from the group consisting of the amino acid sequences of SEQ ID NO: 2 to SEQ ID NO: 6.

In General Formula I, neither $X_1$ nor $X_4$ include an amino acid domain (e. g., a membrane-spanning domain and/or an organelle-targeting domain) capable of preventing the presence of the peptide of the present invention in the cytoplasm.

The protein phosphatase 1 inhibitory peptide of the present invention may include a peptide containing at least one amino acid and having a side chain modification. Examples of the side chain modification include modifications of amino groups, such as, reductive alkylation; amidination with methylacetimidate; acylation with acetic anhydride; carbamolyation of amino groups with cyanate; trinitrobenzylation of amino acid with 2,4,6-trinitrobenzene sulfonic acid (TNBS); alkylation of amino groups with succinic anhydride; and pyridoxylation with pyridoxal-5-phosphate followed by reduction with $NaBH_4$.

The guanidine group of the arginine residue may be modified by the formation of a heterocyclic condensate using a reagent, such as 2,3-butanedione, phenylglyoxal, and glyoxal. The carboxyl group may be modified by carbodiimide activation via O-acylisourea formation, followed by derivatization, for example, to a corresponding amide.

The sulfhydryl group may be modified by methods, such as carboxymethylation with iodoacetic acid or iodoacetamide; performic acid oxidation with cysteic acid; formation of mixed disulfides by other thiol compounds; a reaction by maleimide, maleic anhydride, or other substituted maleimide; formation of mercury derivatives using 4-chloromercuribenzoate, 4-chloromercuriphenylsulfonic acid, phenylmercury chloride, 2-chloromercuri-4-nitrophenol, and other mercurial agents; and carbamoylation with cyanate at alkaline pH. Any modification of the cysteine residue should not affect the formation of a disulfide bond, which is required by the peptide. In addition, the sulfhydryl group of cysteine may be substituted with a selenium equivalent, whereby a diselenium bond may be formed at at least one disulfide bonding site in the peptide.

The tryptophan residue may be modified by, for example, oxidation with N-bromosuccinimide or alkylation of the indole ring by 2-hydroxy-5-nitrobenzyl bromide or sulfonyl halide. Meanwhile, the tyrosine residue may be modified by nitration using tetranitromethane to form a 3-nitrotyrosine derivative.

The modification of the imidazole ring of the histidine residue may be accomplished by alkylation with an iodoacetic acid derivative or N-carbethoxylation with diethylpyrocarbonate.

The proline residue may be modified by, for example, hydroxylation at the 4-position.

The protein phosphatase 1 inhibitory peptide of the present invention can have more improved stability by modifying an amino acid reside thereof. For example, at least one amino acid in the protein phosphatase 1 inhibitory peptide of the present invention may include an acetyl group, a fluorenyl methoxy carbonyl group, a formyl group, a palmitoyl group, a myristyl group, a stearyl group, or polyethylene glycol (PEG).

According to an embodiment of the present invention, a protective group of the acetyl group may be bound to the protein phosphatase 1 inhibitory peptide of the present invention.

As used herein, the term "stability" refers to storage stability (e.g., room-temperature stability) as well as in vivo stability. The foregoing protective group protects the peptide of the present invention from the attack of protein cleavage enzymes in vivo.

According to the present invention, the amino acid sequence of the protein phosphatase 1 inhibitory peptide usable in the present invention is construed to include a peptide sequence having substantial identity to the sequence of the protein phosphatase 1 inhibitory peptide of the present invention. As used herein, the term "substantial identity" means that two amino acid sequences, when optimally aligned and then analyzed by an algorithm ordinarily used in the art, such as BLAST, GAP, or BESTFIT, or by visual inspection, share at least about 60%, 70%, 80%, 85%, 90%, or 95% sequence homology. Methods of alignment for sequence comparison are known in the art. Various methods and algorithms for the alignment are disclosed in Smith and Waterman. (1981) Adv. Appl. Math. 2:482; Needleman and Wunsch. (1970) J Mol Bio 48:443; Pearson and Lipman. (1988) Methods Mol Biol 24: 307-31; Higgins and Sharp. (1988) Gene 73:237-44; Higgins and Sharp. (1989) CABIOS 5:151-3; Corpet et al. (1988) Nuc Acids Res 16:10881-90; and Huang et al. (1992) Comp Appl BioSci 8:155-65 and Pearson et al. (1994) Meth Mol Biol 24:307-31.

According to the present invention, a cell penetrating peptide (CPP) may be further bound to the protein phosphatase 1 inhibitory peptide. The cell penetrating peptide may be bound to the N-terminus and/or the C-terminus of the protein phosphatase 1 inhibitory peptide.

In order to deliver the protein phosphatase 1 inhibitory peptide of the present invention into cells, the protein phosphatase 1 inhibitory peptide needs to include a cell penetrating peptide or a delivery means capable of performing a similar function to the cell penetrating peptide. As used herein, the term "cell penetrating peptide" refers to a peptide essential to deliver a particular peptide into cells, and the cell penetrate peptide may be composed of typically a sequence of 10-50 amino acids or more.

The cell penetrating peptide has an amino acid sequence per se capable of penetrating the phospholipid bilayer of the cell membrane, and includes, for example, dNP2, a Tat-derived peptide, a signal peptide (e. g., a cell penetrating peptide), an arginine-rich peptide, a transportan, or an amphipathic peptide carrier, but is not limited thereto (Morris, M. C. et al. (2001) Nature Biotechnol. 19:1173-1176; Dupont A J. and Prochiantz A. (2002) CRC Handbook on Cell Penetrating Peptides, Langel, Editor, CRC Press; Chaloin, L. et al. (1997) Biochemistry 36(37):11179-87; and Lundberg P and Langel U. (2003) J. Mol. Recognit. 16(5): 227-233). In addition to the above naturally occurring peptides, various antennapedia-based peptides having a cell penetrating property are well known, and include retroinverso and D-isomer peptides [Brugidou J. et al. (1995) Biochem Biophys Res Commun. 214(2):685-93; and Derossi D et al. (1998) Trends Cell Biol. 8:84-87].

According to an embodiment of the present invention, the protein phosphatase 1 inhibitory peptide of the present invention and the cell penetrating peptide may be connected via a linker peptide. The linker peptide may be composed of 1 to 50 amino acids, 4 to 20 amino acids, or 4 to 15 amino acids. In addition, the linker peptide may be composed of glycine (G), serine (S), alanine (A), or a combination thereof. According to an embodiment of the present invention, the sequence of the linker peptide may be composed of an amino acid sequence of $(G)_n$ (provided that n is an integer of 1 to 20). According to another embodiment of the present invention, the linker peptide may be composed of $(G)_3$ to $(G)_{10}$ amino acids. According to another embodiment of the present invention, the linker peptide may be composed of $(G)_3$ to $(G)_5$ amino acids. According to a particular embodiment of the present invention, the linker peptide may be composed of $(G)_3$ amino acids.

As used herein, the term "vascular diseases" includes cardiovascular diseases, pulmonary vascular diseases, cerebral vascular diseases, peripheral vascular diseases, arteriosclerosis, vascular stenosis, or hypertension, but is not limited thereto.

As used herein, the term "hypertension" refers to various forms, diagnoses, levels, or stages of hypertension. According to an embodiment of the present invention, the hypertension is pulmonary hypertension. The pulmonary hypertension includes pulmonary arterial hypertension and pulmonary venous hypertension, but is not limited thereto. According to a particular embodiment of the present invention, the hypertension is pulmonary arterial hypertension.

Meanwhile, the hypertension may include hypertensive vascular disease, hypertensive pulmonary disease, hypertensive encephalopathy, hypertensive heart disease, hypertensive nephrosclerosis, or hypertensive retinitis.

As used herein, the vascular stenosis includes cardiovascular stenosis, carotid artery stenosis, cerebral vascular stenosis, pulmonary stenosis, renal artery stenosis, femoral artery stenosis, lower limb artery stenosis, and vascular restenosis, but is not limited thereto. The vascular restenosis may be caused by vascular surgery or angioplasty.

As used herein, the term "vascular proliferative diseases" refers to diseases caused by abnormal growth of vascular smooth muscle cells (VSMCs). The abnormal growth of vascular smooth muscle cells (VSMCs) is a fundamental cause of several vascular proliferative diseases, such as atherosclerosis or aortic restenosis. Therefore, for a mechanism for inhibiting the proliferation of vascular smooth muscle cells, the present invention employed a method for upregulating SERCA2a activity by inhibiting SERCA2a degradation, and specifically, used a protein phosphatase 1 inhibitory peptide (PP1 inhibitory peptide). The protein phosphatase 1 inhibitory peptide strongly inhibits the protein phosphatase-1 (PP1)-mediated dephosphorylation of phospholamban (PLB).

Specifically, the vascular proliferative diseases are caused by abnormal proliferation of VSMCs having a synthetic phenotype. According to an embodiment of the present invention, rat aortic smooth muscle cells (RASMCs) cultured in 10% FBS high-concentration serum medium (synthetic conditions) exhibits a synthetic phenotype. According to another embodiment of the present invention, the SERCA2a levels is decreased (obtaining a synthetic phenotype) under synthetic conditions in RASMCs, and such attenuation of SERCA2a is again completely inhibited by the protein dephosphorylation 1 inhibitory peptide of the present invention (e.g., ψPLB-SE) (FIG. 2b).

The pharmaceutical composition of the present invention can be administered orally or parenterally, and the parenteral administration can be made by intravenous injection, subcutaneous injection, intra-muscular injection, intraperitoneal injection, transdermal administration, nasal administration/inhalation, or airway inhalation.

The drug delivery via inhalation is one of the non-invasive methods, by which a drug is directly delivered to lung cells through mucous membranes of lungs through nasal cavities or airway. In particular, nucleic acid or peptide delivery through aerosol (or spray) delivery can be advantageously used in an extensive range of treatments of pulmonary disease. This is because the anatomical structure and location of lungs allows an immediate, non-invasive approach, without affecting the other organs, or can receive a topical application of a peptide delivery system. Therefore, in the therapeutic composition of the present invention, the delivery of (i) a nucleic acid delivery complex with a conjugated nucleic acid or (ii) a peptide-supported carrier or powder particles, which are associated with pulmonary diseases, especially, pulmonary vascular diseases, into the lungs in an aerosol manner can expect preventive or therapeutic effects on the above disease. For a formulation for inhalation administration, the nucleic acid delivery complex or peptide delivery carrier can be prepared to have a nanoparticle size.

For example, in order to prepare an aerosol-type pharmaceutical preparation for respiratory administration containing a nucleic acid delivery complex active ingredient, a nucleic acid delivery complex may be prepared by (i) binding with a copolymer for stabilization of a structure of the nucleic acid, or (ii) inserting the nucleic acid sequence into a viral/non-viral vector.

For another example, in order to prepare an aerosol-type pharmaceutical preparation for respiratory administration containing a peptide active ingredient, a peptide may be prepared by collecting the peptide active ingredient in a stable carrier or vehicle, followed by mixing with a pharmaceutically acceptable aqueous or non-aqueous liquid, such as a suspension, a solution, or a water in oil or oil in water emulsion. Also, the composition of the present invention may be prepared as a soil fine particle composition containing respirable dry particles of the peptide active ingredient. The solid fine particle composition containing the peptide active ingredient may optionally contain a dispersant, which is provided to promote aerosol formation.

The composition of the present invention, when used as an aerosol- or spray-type pharmaceutical composition for nasal/respiratory administration, may be prepared as a kit including a respiratory or nasal inhalation/administration device. This kit may contain an aerosol or spray generator, and an inhaler. The inhaler may include a neubulizer or insufflator.

As used herein, the term "pharmaceutically effective amount" refers to an amount sufficient to the treatment of vascular disease, to be administered to a subject.

The pharmaceutical composition of the present invention may contain a pharmaceutically acceptable carrier. The pharmaceutically acceptable carrier is normally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in Remington's Pharmaceutical Sciences (19th ed., 1995).

The appropriate dose of the pharmaceutical composition of the present invention varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present invention, the daily dose of the pharmaceutical composition of the present invention is 0.001-10000 mg/kg.

The pharmaceutical composition of the present invention may be formulated into a unit dosage form or may be prepared in a multi-dose container by using a pharmaceutically acceptable carrier and/or excipient according to a method that can be easily implemented by a person having an ordinary skill in the art to which the present invention pertains. Here, the formulation may be a solution in an oily or aqueous medium, a suspension, an emulsion, an extract, a powder, granules, a tablet, or a capsule, and may further contain a dispersant or a stabilizer. For example, the therapeutic composition of the present invention may be prepared as a formulation for inhalation administration (aerosol) so as to deliver a protein phosphatase 1 inhibitory peptide or a nucleic acid delivery complex expressing the peptide to a target site through aerosol delivery.

In accordance with another aspect of the present invention, there is provided a pharmaceutical composition for use in the treatment of vascular diseases, the composition containing: (a) a pharmaceutically effective amount of a protein phosphatase 1 inhibitory peptide; and (b) a pharmaceutically acceptable carrier.

In accordance with still another aspect of the present invention, there is provided a food composition containing a protein phosphatase 1 inhibitory peptide for mitigation or alleviation of vascular diseases.

Since the food composition of the present invention employs the same active ingredient as the pharmaceutical composition for treatment of vascular diseases of the present invention, overlapping descriptions therebetween are omitted to avoid excessive complexity of the specification.

In accordance with still another aspect of the present invention, there is provided a method for treatment of vascular diseases, the method including administering a pharmaceutical composition to a subject, the composition containing: (a) a pharmaceutically effective amount of a protein phosphatase 1 inhibitory peptide; and (b) a pharmaceutically acceptable carrier.

Since the method for treatment of a vascular disease employs the foregoing pharmaceutical composition for treatment of vascular diseases of the present invention, overlapping descriptions therebetween are omitted to avoid excessive complexity of the specification.

As used herein, the term "administration" refers to the provision of a predetermined material for a patient by any appropriate method, and the pharmaceutical composition of the present invention may be administered orally or parenterally through all general routes as long as the pharmaceutical composition can arrive at target tissues. In addition, the composition of the present invention may be administered using any apparatus (e. g, a nanoparticle sprayer) that can deliver an active ingredient to target cells.

As used herein, the term "subject" refers to, for example, but is not particularly limited to, a human, monkey, cow, horse, sheep, pig, chicken, turkey, quail, cat, dog, mouse, rat, rabbit, or guinea pig, preferably a mammal, and more preferably a human.

Advantageous Effects

Features and advantages of the present invention are summarized as follows.

(a) The present invention is directed to a composition containing a protein phosphatase 1 inhibitory peptide for treatment of vascular diseases.

(b) The present inventors prepared a mimic peptide (ψPLB-SE) including a sequence of the 14th to 22nd amino acids in the amino acid sequence of SEQ ID NO: 1 (phospholamban), and verified that ψPLB-SE restores both the level and activity of SERCA2a in VSMCs under synthetic conditions by targeting protein phosphatase 1 (PP1).

(c) Furthermore, the present inventors found a new mechanism in which the dysfunction of VECs is restored by enhancing activity of endothelial nitric oxide synthase (eNOS) of vascular endothelial cells (VECs), thereby mitigating pulmonary arterial hypertension.

(d) Accordingly, ψPLB-SE can be a basis of therapy strategy for treatment of vascular proliferative diseases.

DETAILED DESCRIPTION

Figure 1A:
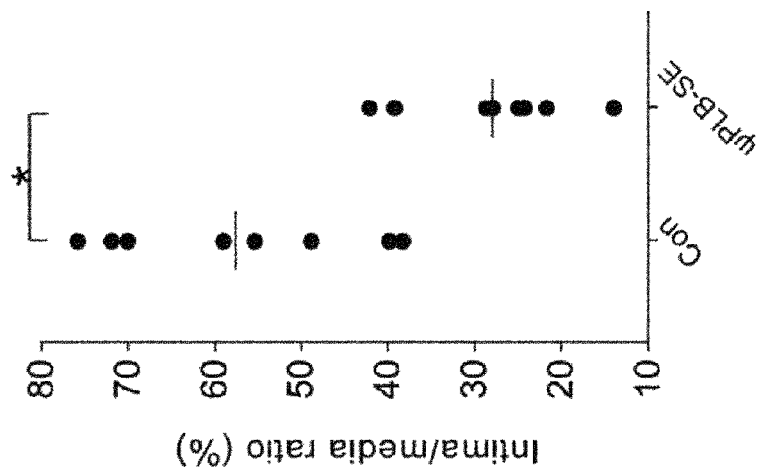
FIGS. 1a, 1b and 1c. The rat carotid artery was subjected to catheter-induced balloon injury. The injured region was treated with 5 μl of ψPLB-SE or control (Con) peptide for 30 min. (1a) Carotid arteries were sectioned, and stained with haematoxylin and eosin (top panels), or immunostained with antibodies against α-SMA (middle panels) and PCNA (bottom panels) 10 days after treatment. The intima/media ratio was calculated (n=8). Scale bar, 50 μm. (1b) RASMCs isolated from the thoracic aorta were incubated in DMEM supplemented with 0.1% (v/v) FBS for 5 days to induce a contractile phenotype, followed by incubation in DMEM supplemented with 10% (v/v) FBS for 24 hours to induce a synthetic phenotype in the presence of 3 μM ψPLB-SE or control peptide. Immunostaining was performed with an antibody against PCNA (red). Nuclei were stained with Hoechst (blue). Representative merged images are shown. Scale bar, 50 μm. (1c) Cell proliferation was quantified using a cell viability assay kit (n=6).
Figure 1A:
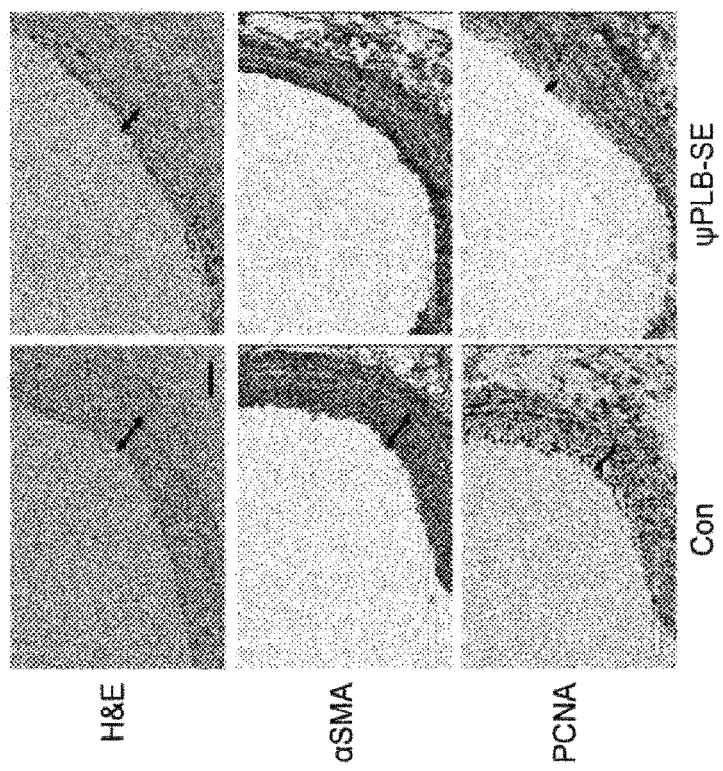

Hereinafter, the present invention will be described in detail with reference to examples. These examples are only for illustrating the present invention more specifically, and it will be apparent to those skilled in the art that the scope of the present invention is not limited by these examples depending on the purposes or gist of the present invention.

EXAMPLES

Methods
1. Ethics Statement

Animal experiments using Sprague-Dawley rats were granted by approval of the Institutional Animal Care and Use Committee (IACUC) of Seoul National University Hospital, Ewha Womans University, and Gwangju Institute of Science and Technology, and conformed to the Guide for Care and Use of Laboratory Animals published by the US National Institutes of Health (The National Academies Press, 8th Edition, 2011). All experiments were performed using 8-week-old male Sprague-Dawley rats from Charles River. Environmental conditions were controlled to provide a temperature of 25±2° C., a relative humidity of 50±5%, and a 12:12 hour light/dark cycle.

2. Chemicals and Synthesis of Protein Phosphatase 1 Inhibitory Peptides

ψPLB-SE (RAE16TIEMPQ; SEQ ID NO: 2) was derived from the PLB protein sequence surrounding the Ser16 phosphorylation site. To facilitate uptake into cells, the peptide was conjugated to the cell penetrating peptide dNP2 (KIKKVKKKGRKGSKIKKVKKKGRK; SEQ ID NO: 21) or TAT (YGRKKRRQRRR; SEQ ID NO: 22). The peptides used in the present invention were PLB-SE (RAETIEMPQ; SEQ ID NO: 2) and control peptide (RASTIEMPQ; SEQ ID NO: 23). PLB-SE and cell penetrating peptide were connected by a linker peptide (GGG; SEQ ID NO: 24) The peptides (purity of 95% or higher, AnyGen, Gwangju, Korea) was resuspended in double-distilled water or physiological saline at a stock concentration of 3 mM (cells), 2.5 mg/ml (rats), or 500 μg/ml (mice). The rats were treated with 1 mg/kg peptides and mice were treated with 2 mg/kg peptides. The rat aortic smooth muscle cells (RASMCs), human coronary smooth muscle cells (HCSMCs), pulmonary arterial endothelial cells (PAECs), and pulmonary arterial smooth muscle cells (PASMCs) were treated with the peptides at a final concentration of 3 μM for 1 hour. The PI3K inhibitor LY294002 (Millipore, USA), the Akt inhibitor Inhibitor IV (Calbiochem, USA), and the PP1 inhibitor okadaic acid (Sigma Aldrich, USA), used in the experiments using pulmonary arterial endothelial cells (PAECs), were purchased. For the monocrotaline aqueous solution, the monocrotaline powder (Sigma Aldrich, USA) was dissolved in a small amount of a 1 M hydrochloric acid solution (HCL), diluted with sterilized distilled water, and adjusted to pH 7.35 by addition of sodium hydroxide (NaOH). The animals were bred and observed in the same conditions as in the control group during the experiment periods. In addition, the calcium ionophore A23187 and the calpain I and II inhibitors MDL28170 and cycloheximide were purchased from Sigma-Aldrich (St. Louis, Mo., USA).

3. Balloon-Induced Injury of Rat Carotid Artery

The left common carotid artery was injured by an infiltration of 2F Fogarty balloon embolectomy catheter. In brief, the rats were anesthetized with isoflurane gas (70% $N_2O$/ 30% $O_2$), the left external carotid artery was exposed, and branches thereof were electro-coagulated. A catheter was inserted approximately 1 cm into the external carotid artery via a transverse arteriotomy, and endothelial denudation was achieved by three passes of the catheter along the common carotid artery. After removal of the catheter, the penetrated area was clamped, and 5 μg of the peptides solubilized in 200 μL of phosphate-buffered saline (PBS) was injected. After incubation for 15 minutes, the sealed carotid artery was re-opened to resume blood flow. The rats were allowed to recover for 10 days, unless otherwise stated. For histological analyses, the rats were anesthetized, and the common carotid artery was excised after transcardiac perfusion with heparinized saline containing 3.7% (w/v) formaldehyde. The specimens were embedded in paraffin, and paraffin blocks were sectioned with the Leica RM2255 rotary microtome. Two serial tissue sections (thickness, 4 μm) were obtained from the centre of the common carotid artery and stained with haematoxylin and eosin. The lamina, internal elastic lamina, and external elastic lamina were measured with the National Institutes of Health ImageJ software (version 1.62). The intimal and medial areas were determined by subtracting the laminal area from the internal elastic laminal area and by subtracting the internal elastic laminal area from the external elastic laminal area, respectively. The values from two serial sections per rat were averaged for analysis.

4. Immunohistochemistry

The carotid artery was fixed in 4% (w/v) paraformaldehyde for 48 hours at room temperature and then washed with PBS. After embedding the specimens in paraffin and sectioning the tissue blocks, the sections were treated with hydrogen peroxide to quench endogenous peroxidase activity, followed by boiling in antigen retrieval buffer. The specimens were immunostained with antibodies against α-SMA (Sigma-Aldrich), SERCA2a, SERCA2b (21st Century Biochemical), and PCNA (Abcam).

5. Cell Culture

The rat aortic smooth muscle cells (RASMCs) were isolated from the medial layer of the thoracic aorta derived from male Sprague-Dawley rats (body weight, 180-200 g) by an enzymatic reaction with collagenase (50 U/mL, Worthington) and pancreatic elastase (0.25 mg/mL, Sigma-Aldrich) for 4 hours at 37. The cells were collected and resuspended in DMEM containing 20% (v/v) fetal bovine serum. The resuspension was then plated on collagen I (Sigma-Aldrich)-coated glass coverslips and incubated at 37 in an atmosphere of 5% (v/v) $CO_2$ and 95% (v/v) air. Human coronary smooth muscle cells (HCSMCs), pulmonary arterial endothelial cells (PAECs), and pulmonary arterial smooth muscle cells (PASMCs) were purchased from Lonza and cultured in EBM or SmBM (Lonza) supplemented with 0.5 mg/mL hEGF, 5 mg/mL insulin, 1 mg/mL hFGF, 50 mg/mL gentamicin/amphotericin-B, and 5% fetal bovine serum. All the cells were cultured at 37 in 5% (v/v) $CO_2$ and 95% (v/v) air. RASMCs and HCSMCs were, respectively, plated at the densities of $1\times10^4$ cells/$cm^2$ and $1\times10^5$ cells/$cm^2$ for immunostaining and western blotting experiments. For RASMC and PASMC cell proliferation experiments, these cells were cultured in fetal bovine serum-free media for 3 days, and then proliferation was induced by serum addition.

6. Fluorescent Immunostaining

Rat aortic smooth muscle cells (RASMCs) were fixed in 4% (w/v) paraformaldehyde at room temperature for 10 min, washed with PBS, and then transmitted with 0.1% (v/v) Triton X-100 in PBS for 40 min. After washing and blocking with 3% (w/v) BSA in PBS, the cells were incubated overnight at room temperature with antibodies against SERCA2a (1:250), SERCA2b (1:250), and PCNA (1:50). On the following day, the cells were washed with PBS and incubated with anti-rabbit and anti-mouse IgG conjugated to Alexa Fluor 488 and 594, respectively, for 1 hour at room temperature. The cells were treated with FluoroGuard antifade reagent (Bio-Rad, Hercules, Calif., USA), and the coverslips were examined under a fluorescent microscope.

7. Proliferation Assay

The rat aortic smooth muscle cells (RASMCs) and pulmonary arterial smooth muscle cells (PASMCs) ($1\times10^4$ cells/well) were seeded on a 96-well microplate and treated with peptides at a final concentration of 3 μM for 24 hours. Cell proliferation assays were performed using the EZ-CyTox cell viability assay Kit (Daeil Lab Services Co., Ltd.).

8. Aorta Ex Vivo Organ Culture

A rat thoracic aorta was harvested and incubated in RPMI-1640 medium containing 20 mM HEPES, 2 mM L-glutamine, 100 IU/mL penicillin, and 100 μg/mL streptomycin. The adventitia was removed, and the aorta was cut longitudinally and fixed onto a resin. To investigate the degradation of SERCA2a, tissue fragments were cultured for 7-10 days in RPMI-1640 medium containing 20% (v/v) FCS. The medium was replaced every 48 hours.

9. Western Blotting

Vascular smooth muscle cells (VSMCs) were homogenized in a minimal volume of 50 mM Tris-HCl, pH 7.4, supplemented with a broad-spectrum protease inhibitor cocktail (Calbiochem). The proteins were separated by SDS-PAGE and then transferred to polyvinylidene fluoride membranes (Schleicher & Schuell). After blocking with 5% (w/v) non-fat milk for 1 hour and washing with TBST, the membranes were incubated with antibodies against SERCA2a, SERCA2b (21st century biochemical), PCNA (abcam), GAPDH (Sigma-Aldrich), phospho-eNOS, eNOS, phospho-eIF2α, eIF2α (cell signaling), Vimentin, α-SMA, BMPR2 (Santa cruz), phospho-Akt, Akt (cell signaling), phospho-phospholamban (Merck), and Phospholamban (cell signaling). The membranes were then incubated with horseradish peroxidase-conjugated secondary antibodies (Jackson ImmunoResearch, West Grove, Pa., USA) and developed using a chemiluminescent substrate (Dogen). The blots were scanned and quantified using LAS software.

10. Intracellular $Ca^{2+}$ Measurements

The intracellular $Ca^{2+}$ level was measured in VSMCs by loading cells with 0.5 μM Fura2-AM (Molecular Probes, Eugene Oreg., USA), a $Ca^{2+}$-sensitive indicator, for 15 minutes at 37. The fluorescence was recorded using the IonOptix calcium imaging system. VSMCs were stimulated by the exposure to light emitted by a 75 W halogen lamp through either a 340 nm or 380 nm filter. The fluorescent emissions were detected between 480 nm and 520 nm by a photomultiplier tube after an initial illumination at 340 nm for 0.5 second and then at 380 nm during recording. The 340 nm excitation scan was repeated at the end of the protocol, and qualitative changes in the intracellular $Ca^{2+}$ level were inferred from the ratio of the Fura2 fluorescent intensity at both wavelengths.

11. In Vitro Cell Scratch Assay

RASMCs isolated from the thoracic aorta were cultured in DMEM supplemented with 0.1% (v/v) FBS (Contractile) or in DMEM supplemented with 10% (v/v) FBS (Synthetic) in the presence of 3 μM of control peptide (Con; SEQ ID NO: 23) or ψPLB-SE peptide (SEQ ID NO: 2). Alternatively, RASMC cultured in DMEM supplemented with 0.1% (v/v) FBS were treated with 10 ng/ml of PDGF-BB (R&D Systems) (Synthetic) in the presence of 3 μM control or ψPLB-SE peptide. A region of the RASMC layer was removed by scratching the plate with a sterile 200 μL pipette tip. The cells were incubated for 12 hours or 24 hours and then observed under an 1×80 microscope (Olympus). The distance traveled by the cells was measured using MetaMorph software.

12. Assay for SERCA2a Stability

RASMCs were cultured in DMEM supplemented with 0.1% (v/v) FBS (Contractile) or in DMEM supplemented with 10% (v/v) FBS (Synthetic) in the presence of 3 μM control or ψPLB-SE peptide. Cycloheximide (Sigma) was added to media to a final concentration of 5 μg/ml. Cells were harvested after 0, 3, and 5 days of incubation and their protein extracts were subjected to western blotting.

13. Pulmonary Arterial Hypertension Animal Models

Eleven Sprague-Dawley rats (Damool science, Korea) weighing 250-300 g were administered with 60 mg/kg monocrotaline (MCT) (Sigma Aldrich) via intraperitoneal injection, and three animals of a control group were administered with 0.9% physiological saline. According to the dosing schedule, simultaneously with the administration of MCT, six animals for the control group were administered with ψPLB-SE peptide diluted in 300 μl via respiratory inhalation four times at intervals of one week. Five animals for the control group were administered with control peptide. The rats were sacrificed one week after the administration with last peptide, and then histological analysis and molecular biological experiments were conducted.

As for mice, fifteen C57BL/6 mice (Damool science, Korea) weighing 25-30 g were treated with 600 mg/kg MCT five times a week. Out of the mice, eight animals for a comparison group were administered with ψPLB-SE peptide four times at intervals of one week from day 15 after the administration of MCT. Five animals for a control group were administered with a control peptide. The mice were sacrificed one week after last administration, and then histological analysis and molecular biological experiments were conducted.

14. Rat Right Heart Catheterization for Measurement of Pulmonary Artery Pressure In order to indirectly measure the pulmonary artery pressure, right heart catheterization was conducted on the basis of a procedure reported in Nature Protocols in 2008. Rats were anesthetized, followed by tracheal intubation. The rats were placed on a homeothermic plate (AD Instruments, Spechbach, Germany) for the maintenance of body temperature during heart catheterization, and then kept breathing using an artificial respiratory device only for an animal (MiniVent type 845, Hugo Sachs Elektronik, March-Hugstetten, Germany). The chest of the rats was opened, and then high-fidelity 1.4 F micromanometer/Mikro-Tip Pressure catheter (Millar Instruments, Houston, Tex.) was allowed to infiltrate the tricuspid site, to measure the right ventricular end-systolic pressure, right ventricular end-diastolic pressure, left ventricular end-systolic pressure, and left ventricular end-diastolic pressure (RVESP, RVEDP, LVESP, LVEDP). Related values and data were collected and analyzed using the PowerLab data acquisition system (MPVS-Ultra Single Segment Foundation System, AD Instruments) and LabChart 7 for Windows software.

15. Histopathological Staining (Hematoxylin-Eosin, Masson-Trichrome Staining)

Pulmonary tissues were taken from animal models, fixed with 4% (w/v) paraformaldehyde for 5 days at room temperature, and then washed with PBS. After embedding the specimens in paraffin and sectioning the tissue blocks into a thickness of 7 μm, the sections were stained with haematoxylin and eosin (Sigma Aldrich) to investigate the vascular thickness and inflammation, and the sections were stained with Masson-trichrome (Sigma Aldrich) to investigate the extent of perivascular fibrosis, and then observed through an optical microscope.

16. Cytokine Analysis

The pulmonary tissues were obtained from rats and mice, and the cytokine levels in the tissues were quantitatively analyzed using human proinflammatory 10plex Meso Scale Diagnostics plates (MSD; Rockville, Md.).

17. Quantitative RT-PCR

Quantitative RT-PCR was performed using SYBR premix Ex Taq™ (Takara), though which the transcriptional levels of target genes were analyzed. RNA was isolated from pulmonary tissues using trizole (ambion), and synthesized into cDNA. Quantitative RT-PCR conditions were 40 cycles: 10 sec at 94° C., 30 sec at 59° C., and 10 sec at 72° C. The information of primers used in the experiment are shown in Table 1 below.

TABLE 1

| Genes | Forward primer | Reverse primer |
|---|---|---|
| Mousr TGF-β1 | 5'-CAACAATTCCTGGCGTTACCTTGG-3' (SEQ ID NO: 7) | 5'-GAAAGCCCTGTATTCCGTCTCCTT-3' (SEQ ID NO: 8) |
| Mouse Collagen 1 | 5'-CCCAAGGAAAAGAAGCACGTC-3' (SEQ ID NO: 9) | 5'-AGGTCAGCTGGATAGCGACATC-3' (SEQ ID NO: 10) |
| Mouse α-SMA | 5'-ATCGTCCACCGCAAA-3' (SEQ ID NO: 11) | 5'-AAGGAACTGGAGGCGCTG-3' (SEQ ID NO: 12) |
| Mouse IL-1β | 5'-CAACCAACAAGTGATATTCTCCAT-3' (SEQ ID NO: 13) | 5'-GATCCACACTCTCCAGCTGCA-3' (SEQ ID NO: 14) |
| Mouse TNF-α | 5'-CATCTTCTCAAAATTCGAGTGACAA-3' (SEQ ID NO: 15) | 5'-TGGGAGTAGACAAGGTACAACCC-3' (SEQ ID NO: 16) |
| Mouse F4/80 | 5'-CTTGGCTATGGGCTTCCAGTC-3' (SEQ ID NO: 17) | 5'-GCAAGGAGGACAGAGTTTATCGTG-3' (SEQ ID NO: 18) |
| Mouse MCP-1 | 5'-GCTCAGCCAGATGCAGTTAA-3' (SEQ ID NO: 19) | 5'-TCTTGAGCTTGGTGACAAAAACT-3' (SEQ ID NO: 20) |

18. Calcium Uptake Assay

Pulmonary arterial smooth muscle cells (PASMCs) were homogenized in a solution of pH 7.0 containing 40 mM imidazole, 10 mM NaF, 1 mM EDTA, 300 mM sucrose, and 0.5 mM DTT, and 250 μg of the lysate was added to an uptake buffer of pH 7.0 containing 100 mM KCl, 5 mM $MgCl_2$, 5 mM $NaN_3$, 0.5 M EGTA, and 40 mM imidazole, and calcium uptake assay was performed with a calcium concentration of pCa 6, containing radioactive isotopes. The cells were treated with 1 μM ruthenium red (Sigma Aldrich), followed by waiting at 37° C. for 3 min, and then treated with 5 mM K-oxalate and Mg-ATP (Sigma Aldrich). In addition, 500 μl of the reaction material was filtered out through a 0.45 μm filter (Millipore) from the start of a reaction to 4 minutes at intervals of 1 minute, and cpm (count per minute) was measured using a scintillation counter (Beckman).

19. Statistical Analysis

All data are reported as the means±SD. Statistical significance was determined by Student's t-test or one-way ANOVA with Bonferroni post-hoc analysis using StatView 5.0 software (SAS Institute, Cary, N.C., USA). A p-value <0.05 was considered statistically significant.

Results

1. ψPLB-SE Inhibits the Proliferation of VSMCs

The present inventors invented a 9-mer peptide, ψPLB-SE, that improves cardiomyocyte contractility by preserving SERCA2a activity during ischemia-reperfusion injury, in the previous studies [Oh J G et al. (2013) J Mol Cell Cardiol 56: 63-71]. In the present invention, experiments were carried out whether the peptide can also inhibit the proliferation of vascular smooth muscle cells (VSMCs) through a similar molecular mechanism. An injury in the rat carotid artery was induced by balloon angioplasty, and then ψPLB-SE or control peptide was administered to the injured site. The arteries were harvested 4 weeks after treatment, and tissue sections were subjected to haematoxylin and eosin staining and immunocytochemistry. Haematoxylin and eosin staining results showed that neointimal formation was inhibited in arteries treated with ψPLB-SE compared with those treated with the control peptide. The intimal layer affected by ψPLB-SE was positively immunostained with antibodies against α-smooth muscle actin (α-SMA) and proliferating cell nuclear antigen (PCNA). These results indicate that ψPLB-SE inhibits neointimal growth and in vivo VSMC proliferation (FIG. 1a).

Figure 1B:
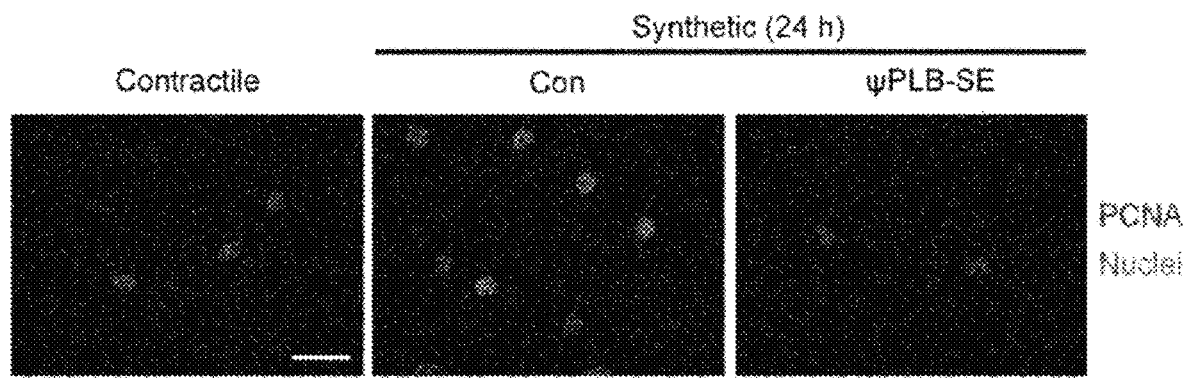
Figure 1C:
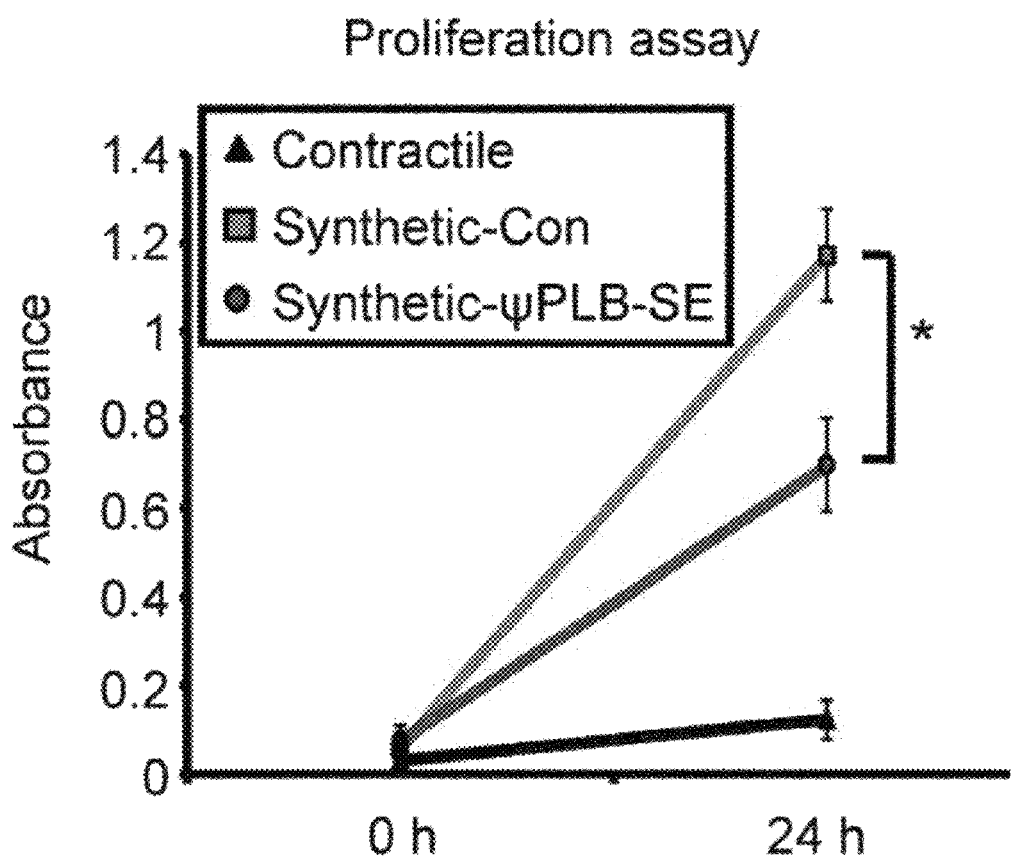

The present inventors examined the effects of ψPLB-SE on rat aortic smooth muscle cells (RASMCs). RASMCs exhibited a contractile phenotype when cultured in medium supplemented with a low concentration of serum (0.1% FBS), whereas the cells exhibited a synthetic phenotype in medium with a high concentration of serum (10% FBS). The present inventors, therefore, defined high serum culture conditions. RASMCs showed active cell division under synthetic conditions, as shown by prominent PCNA expression, but this was completely blocked by ψPLB-SE (FIG. 1b). Cell proliferation assays also showed that the increased proliferation of RASMCs under synthetic conditions was inhibited by ψPLB-SE (FIG. 1c). The increased migratory activity of RASMCs under synthetic conditions or upon the treatment with PDGF-BB was also inhibited by ψPLB-SE (FIGS. 5a-5f). These data indicate that ψPLB-SE markedly inhibits the proliferation of VSMCs under in vitro synthetic condition.

2. ψPLB-SE Prevents Degradation of SERCA2a in VSMCs

Figure 2A:
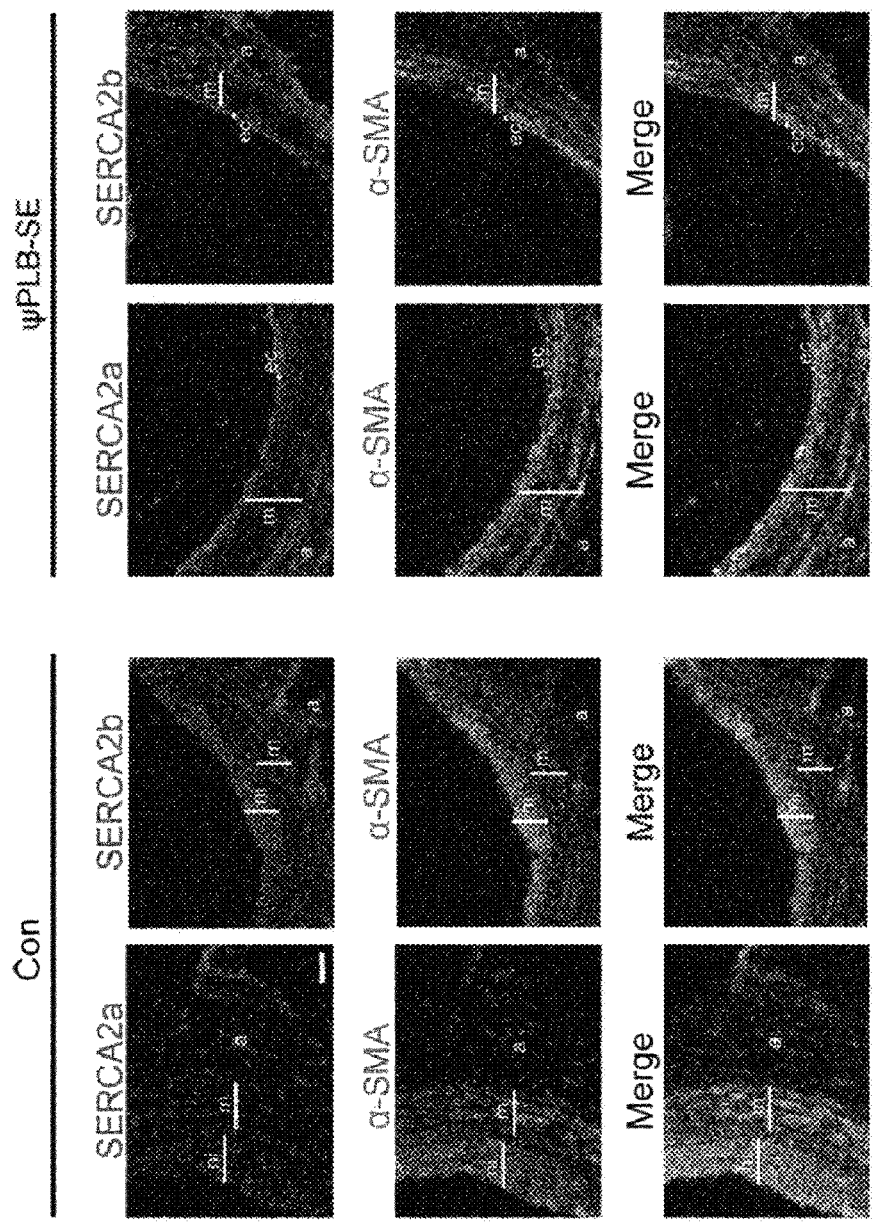
FIGS. 2a, 2b, 2c and 2d. (2a) Carotid arteries were sectioned, and immunostained with antibodies against SERCA2a or SERCA2b (red) and α-SMA (green) 10 days after peptide treatment. Merged images are shown (bottom). a, adventitia; ec, endothelial cell layer; m, medial layer; ni, neointimal layer. Scale bar, 50 μm. (2b) RASMCs isolated from the thoracic aorta were incubated in DMEM supplemented with 0.1% (v/v) FBS for 5 days to induce a contractile phenotype, followed by incubation in DMEM supplemented with 10% (v/v) FBS for 5 days to induce a synthetic phenotype in the presence of 3 μM ψPLB-SE or control peptide. Immunostaining was performed with antibodies against SERCA2a or SERCA2b (green) and PCNA (red). Nuclei were stained with Hoechst (blue). Representative merged images are shown. Scale bar, 50 μm. (2c) Western blot analysis of cell extracts (2d) Ex vivo cultures of the thoracic aorta treated with ψPLB-SE or control peptide. Tissue extracts were subjected to western blotting. Data are expressed as the means±SD (n=3-4; *, P<0.05).
Figure 2B:
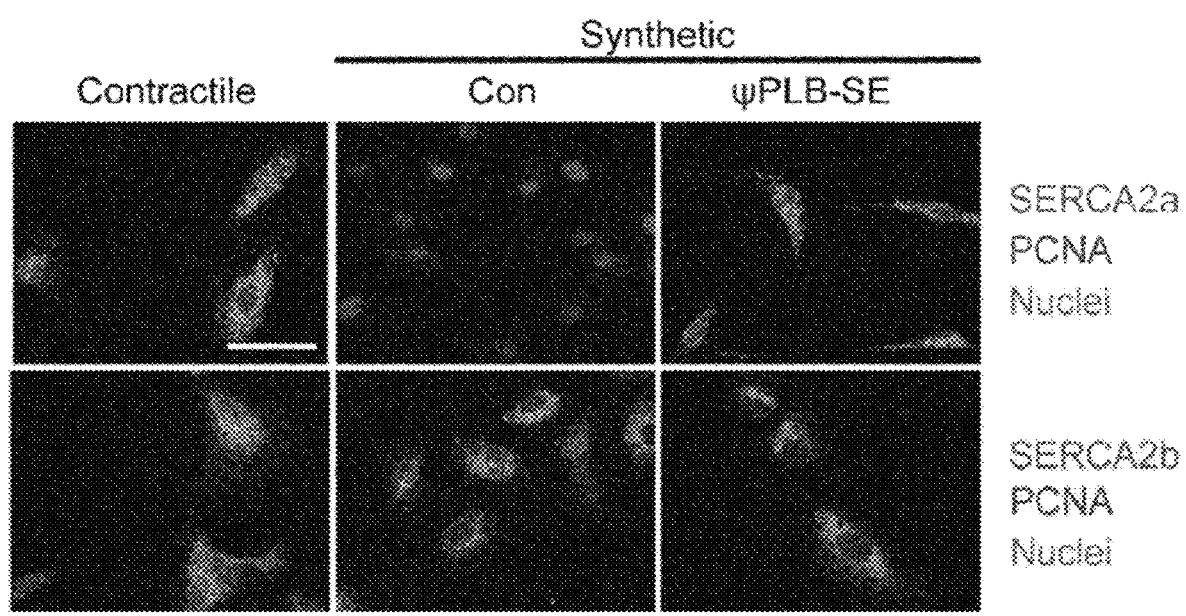
Figure 2C:
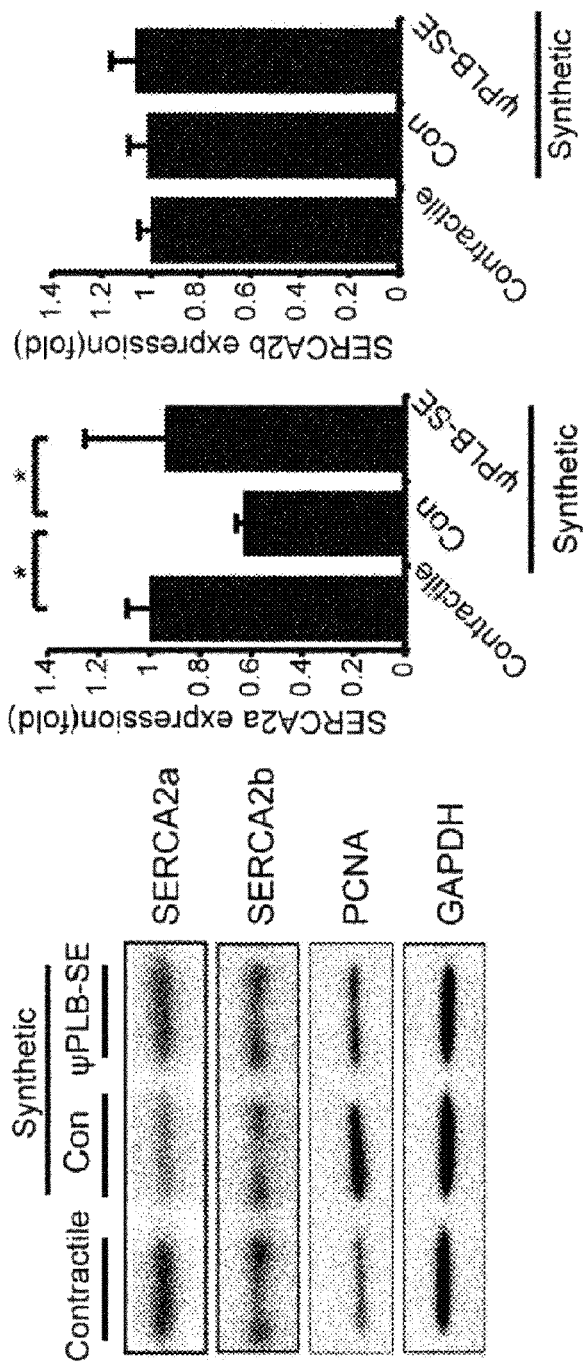
Figure 2D:
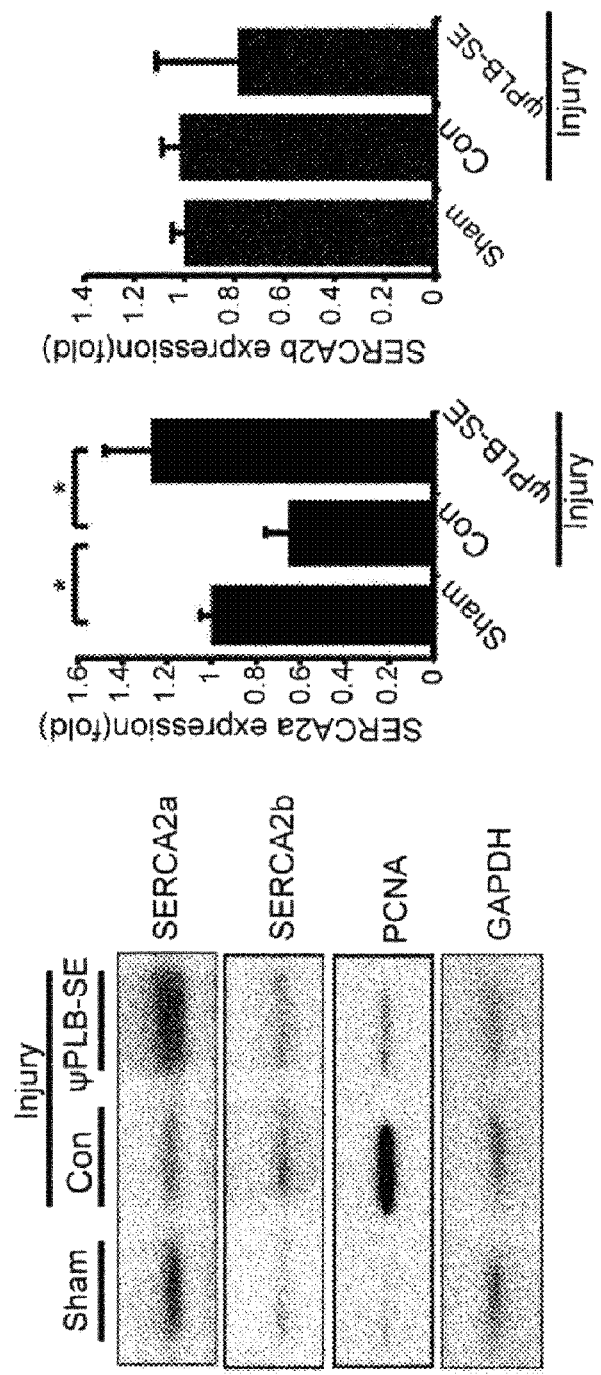
Figure 6A:
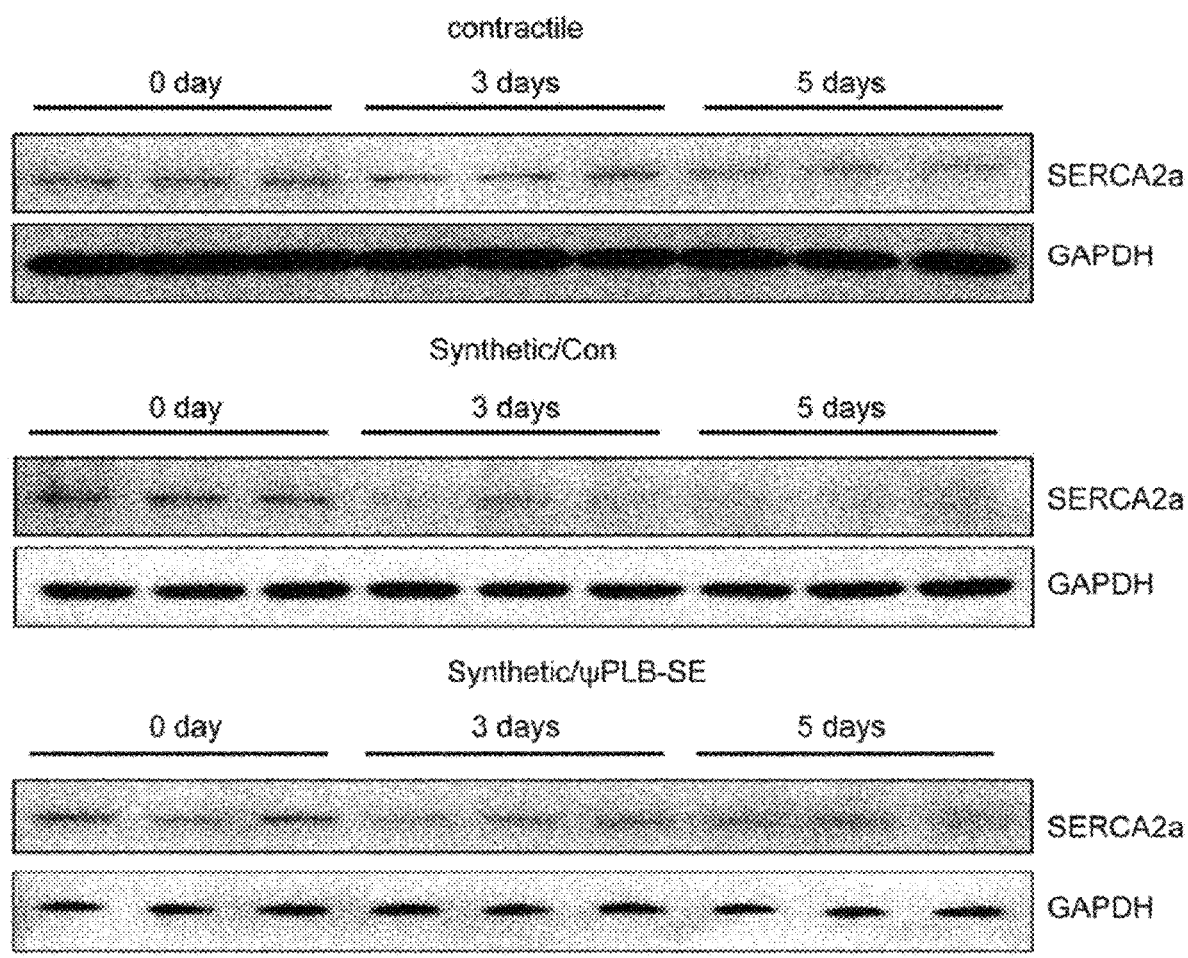
FIGS. 6a and 6b. RASMCs were cultured in contractile or synthetic media in the presence of control or 3 μM ψPLB-SE peptide. Cycloheximide was added to media to a final concentration of 5 μg/ml to prevent de novo protein synthesis. Cells were harvested after 0, 3, and 5 days of incubation and their protein extracts were subjected to western blotting. Data are expressed as the means±SD (n=3-4; *, P<0.05).
Figure 6B:
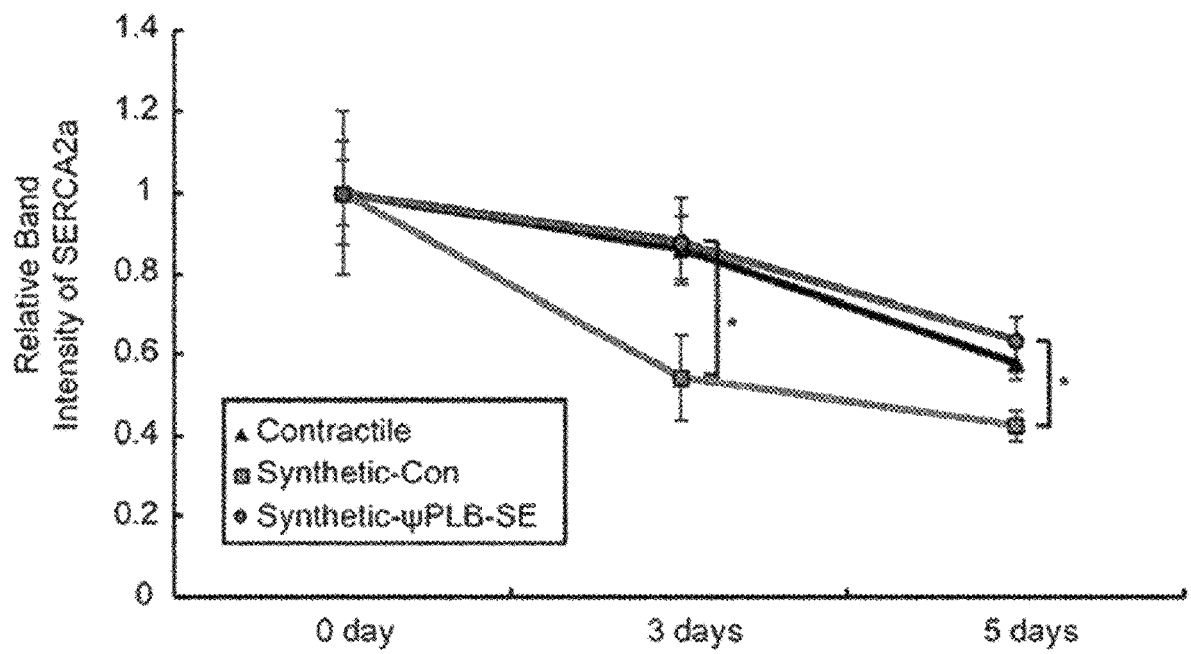

SERCA2a is rapidly degraded in proliferative VSMCs, whereas SERCA2b is relatively stable. The restoration of the SERCA2a level by gene transfer inhibits the proliferation of VSMCs under synthetic conditions. Therefore, the present inventors reasoned that the anti-proliferative effects of ψPLB-SE may be associated with the maintenance of the SERCA2a level and activity under synthetic conditions. The carotid artery sections obtained from the experiment shown in FIG. 1A were immuno-stained with antibodies against SERCA2a, SERCA2b, and α-SMA. While the SERCA2b protein level was not changed, the SERCA2a level was significantly reduced by balloon angioplasty-mediated injury, which was inhibited by ψPLB-SE (FIG. 2a). In addition, immunostaining showed that the SERCA2a level decreased in RASMCs under synthetic conditions, and that this SERCA2a reduction was again completely inhibited by ψPLB-SE (FIG. 2b). Western blotting in the same conditions confirmed that ψPLB-SE inhibited the reduction of SERCA2a in RASMCs under synthetic conditions (FIG. 2c). The present inventors measured the SERCA2a level in RASMCs under conditions where de novo protein synthesis was blocked with cycloheximide. The stability of SERCA2a was significantly attenuated under synthetic conditions, and the stability was restored nearly to the level observed under contractile conditions upon the treatment with ψPLB-SE (FIGS. 6a-6b). An ex vivo culture of the rat thoracic aorta was prepared. After the induction of injury by scratching, VSMCs showed a reduced SERCA2a level, which implies the acquisition of a synthetic phenotype. This injury-dependent reduction of SERCA2a in VSMCs was completely inhibited by ψPLB-SE (FIG. 2d). Collectively, these data indicate that ψPLB-SE inhibits the degradation of SERCA2a in VSMCs.

3. Calpain is Involved in SERCA2a Degradation in VSMCs

Figure 3A:
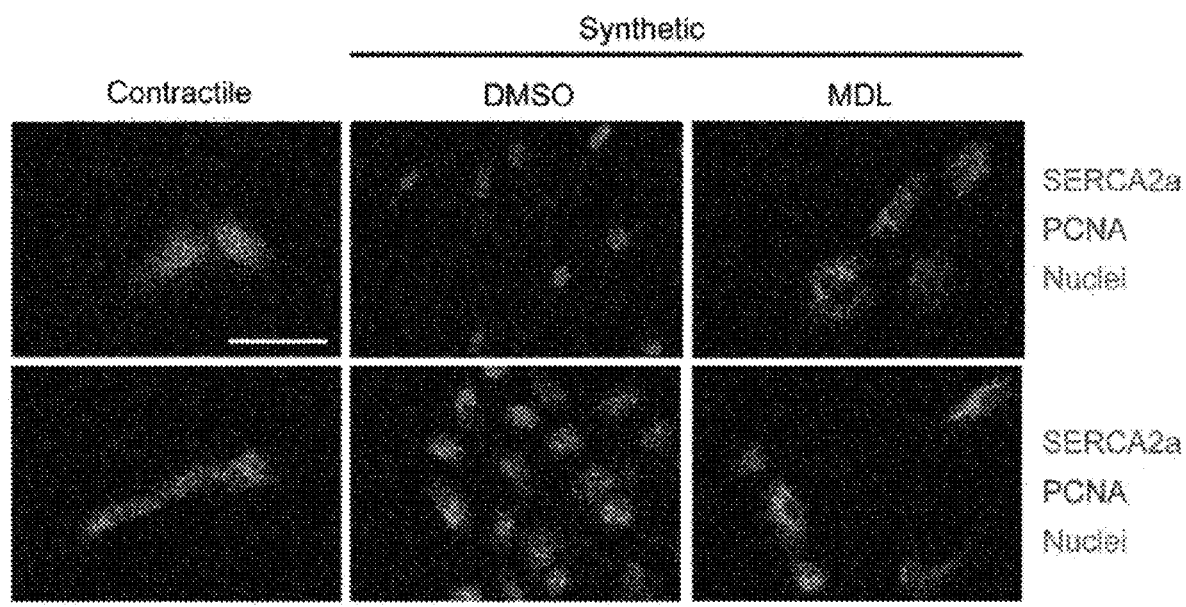
FIGS. 3a and 3b. (3a) RASMCs were treated with the calpain inhibitor MDL28170 or DMSO under the same conditions as described for FIG. 2B. Immunostaining was performed with antibodies against SERCA2a or SERCA2b (green) and PCNA (red). Nuclei were stained with Hoechst (blue). Representative merged images are shown. Scale bar, 50 μm. (3b) Western blot analysis of cell extracts Data are expressed as the means±SD (n=3-4; *, P<0.05).
Figure 3B:
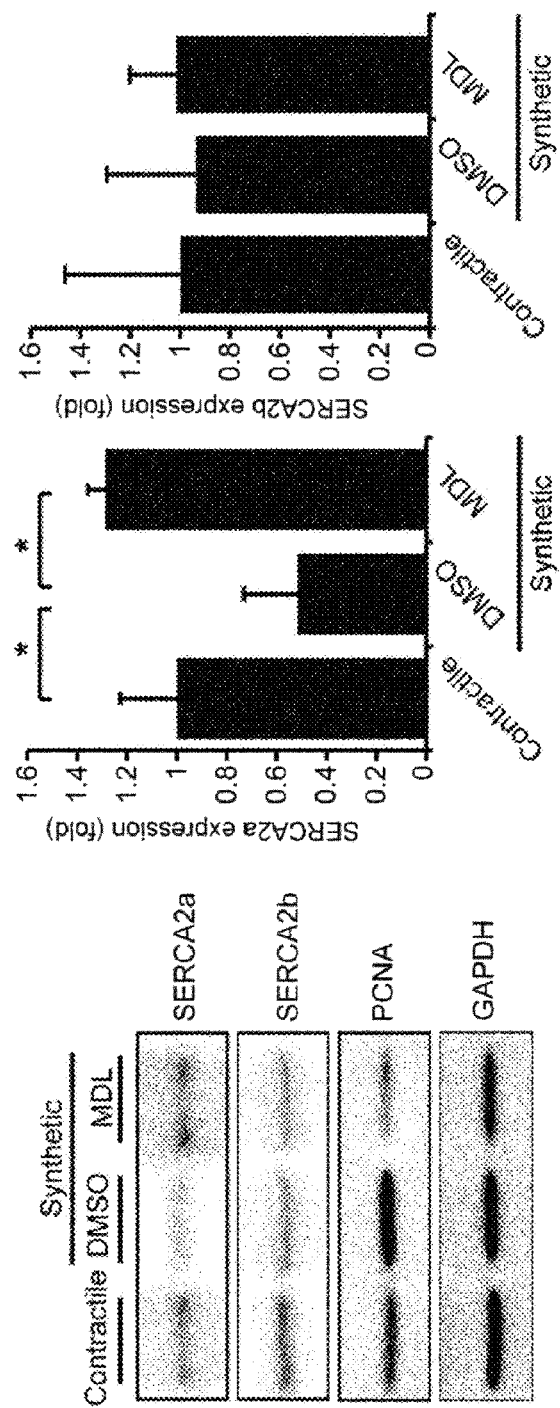

An increase in the cytosolic $Ca^{2+}$ level induces calpain-mediated degradation of cytosolic proteins [Saido T C et al. (1994) Faseb J 8: 814-822; and Matsumura Y et al. (2001) J Mol Cell Cardiol 33: 1133-1142]. Since calpain is involved in the proliferation of VSMCs [Ariyoshi H et al. (1998) Arterioscler Thromb Vasc Biol 18: 493-498], the present inventors examined the roles of calpain in the degradation of SERCA2a in VSMCs. As can be shown from the immunostaining results, the calpain inhibitor MDL28170 inhibited the degradation of SERCA2a in RASMCs under synthetic conditions (FIG. 3a). The protective effect of MDL28170 was further confirmed by western blotting (FIG. 3b). These data indicate that calpain mediates the degradation of SERCA2a in VSMCs under synthetic conditions. The PCNA level decreased by MDL28170 indicates that the sustained SERCA2a level inhibits the inhibition of VSMCs proliferation (FIG. 3a).

4. ψPLB-SE Inhibits Calpain-Dependent Degradation of SERCA2a

Figure 4A:
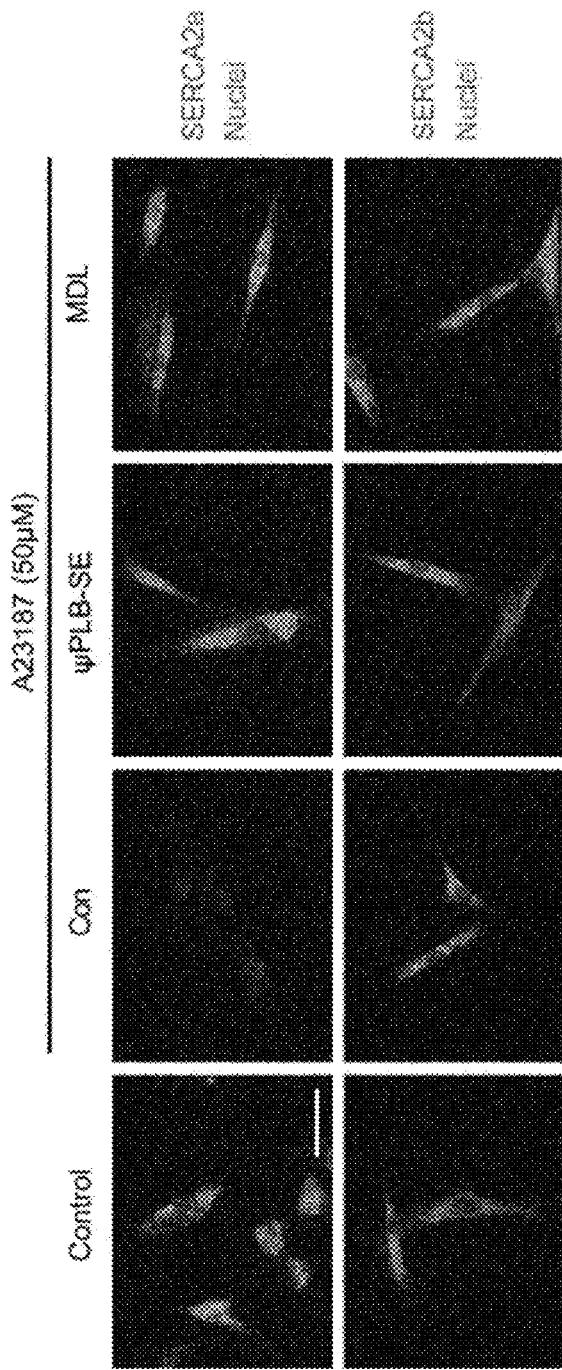
FIGS. 4a, 4b, 4c and 4d. (4a-4c) HCSMCs were pretreated with 3 μM ψPLB-SE and 15 μM MDL28170 for 1 hour, and then treated with 50 μM A23187 for 2 hours. (4a) Immunostaining was performed with antibodies against SERCA2a and SERCA2b (green). Nuclei were stained with Hoechst (blue). Representative merged images are shown. Scale bar, 50 μm. (4b) Western blot analysis was performed with cell extracts. Data are expressed as the means±SD (n=3-4; *, P<0.05). (4c) Baseline $Ca^{2+}$ concentration was measured by IonOptix calcium imaging system. (4d) RASMC were treated with ψPLB-SE or control peptide under the same conditions as described for FIG. 1B. The baseline $Ca^{2+}$ concentration was measured by IonOptix calcium imaging system (*, P<0.05).
Figure 4B:
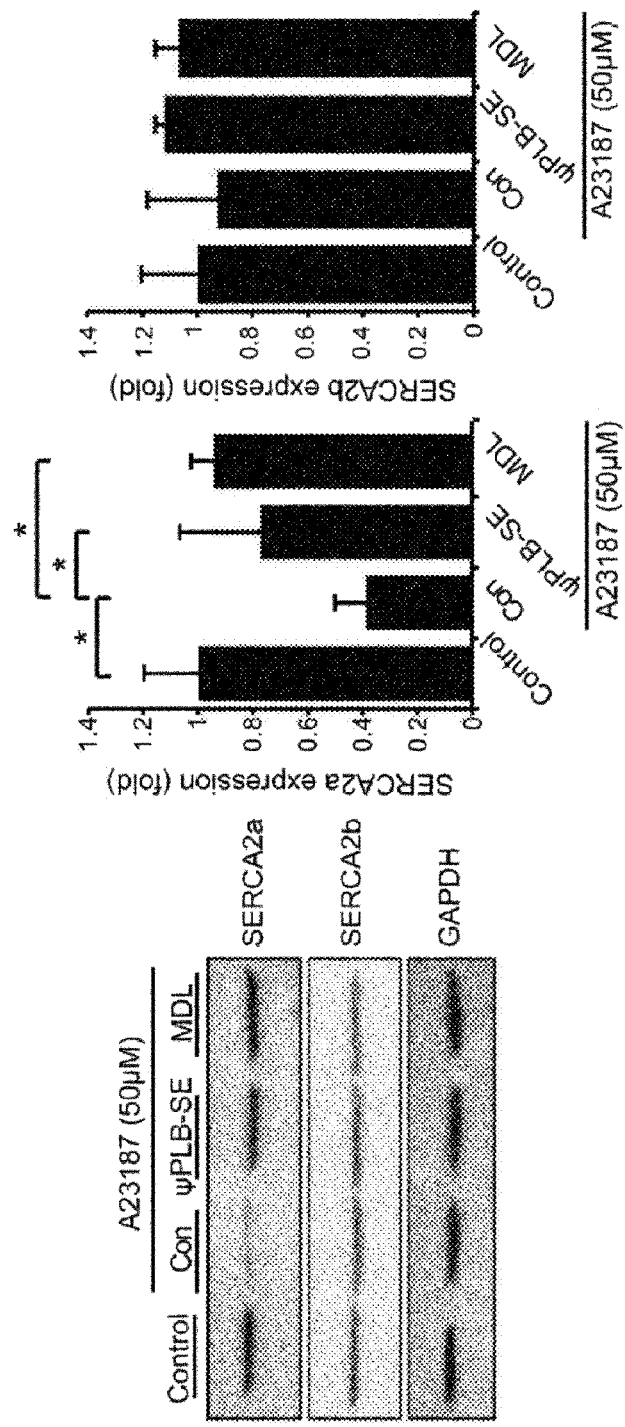
Figure 4C:
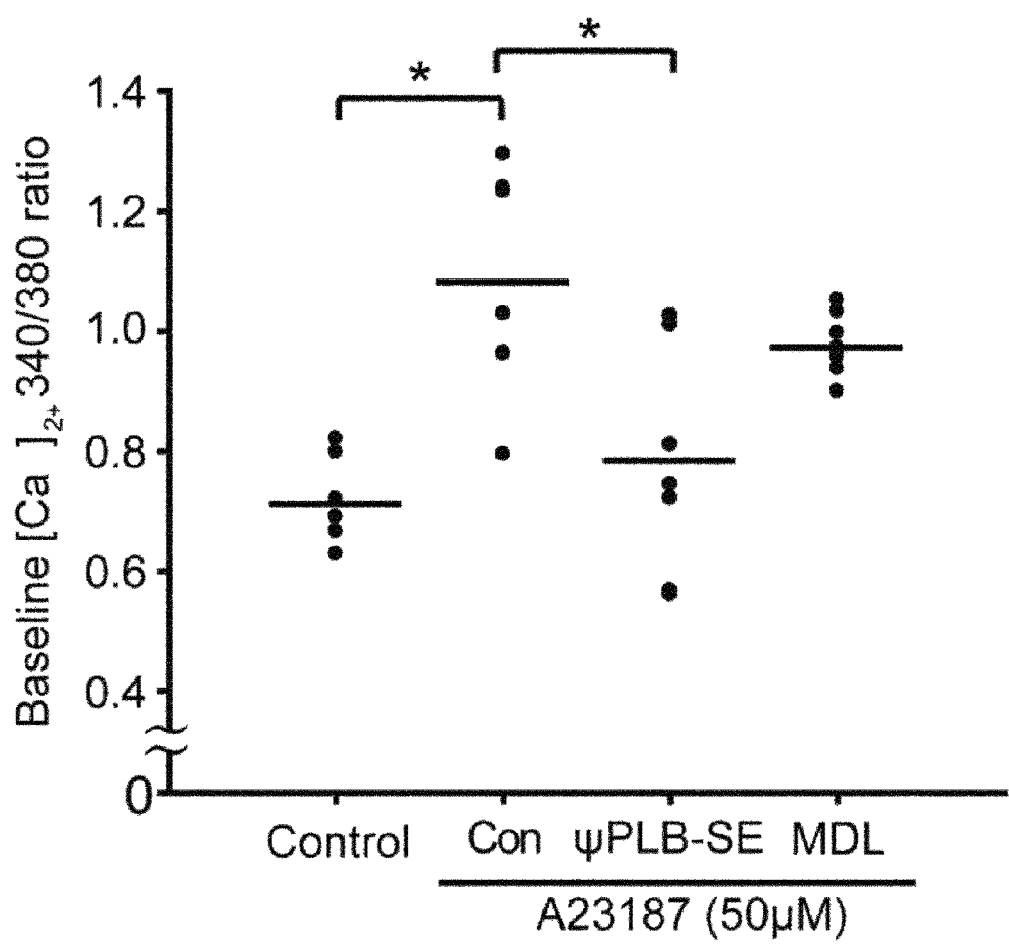
Figure 4D:
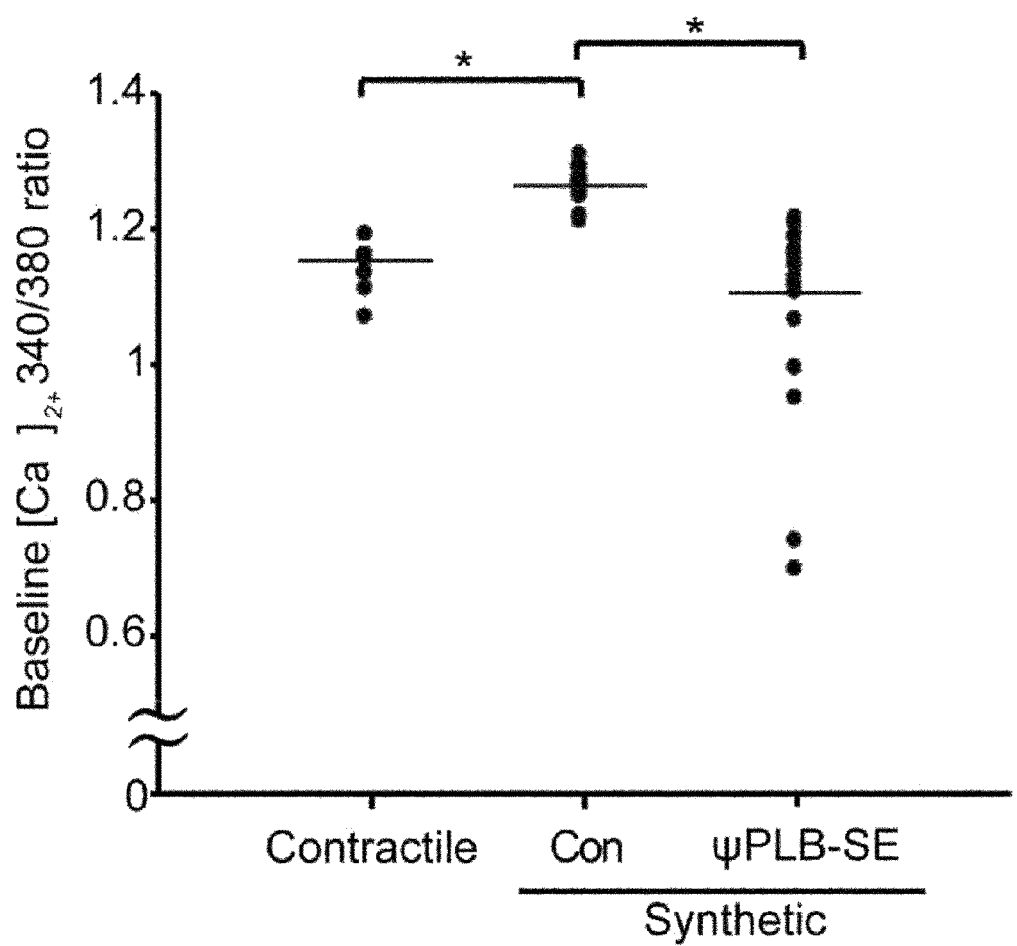
Figure 5A:
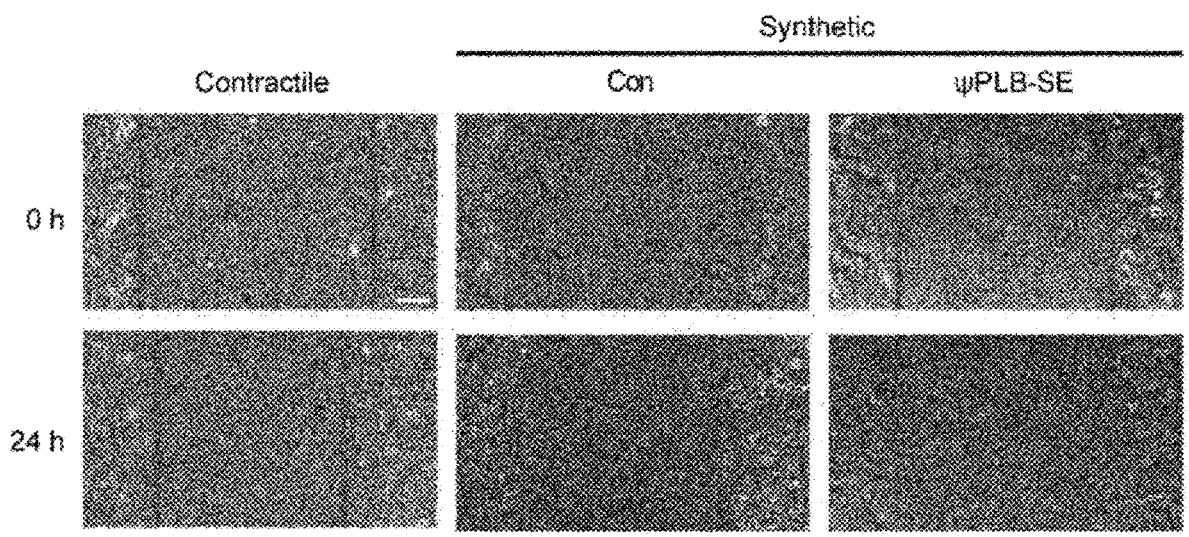
FIGS. 5a, 5b, 5c, 5d, 5e and 5f. (5a-5b) RASMCs were cultured in contractile or synthetic media and scratched. Control or ψPLB-SE peptide was added and further culture was performed for 24 hours. The relative distance of cell migration was measured under a phase contrast microscope. Red lines indicate the boundaries of the RASMC cultures. Representative images (left) and cell migration distances (right) are shown (n=4). Scale bar, 50 μm. (5c) RASMCs were cultured in contractile media, and synthetic phenotypes were induced by addition of PDGF-BB in the presence of 3 μM of control or ψPLB-SE peptide. Immunostaining was performed with an antibody against PCNA (red). Nuclei were stained with Hoechst (blue). Representative merged images are shown. Scale bar, 50 μm. (5d) Cell proliferation was quantified using a cell viability assay kit. (5e-5f) RASMCs were subjected to scratch assay under the same conditions as described in FIG. 5c. Representative images (left) and cell migration distances (right) are shown. Scale bar, 50 μm.
Figure 5B:
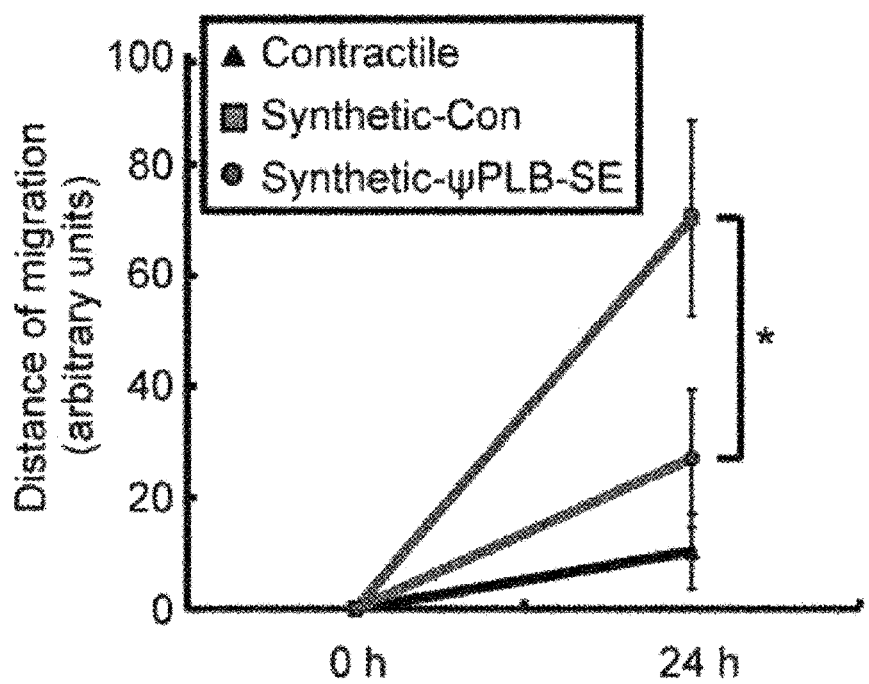
Figure 5C:
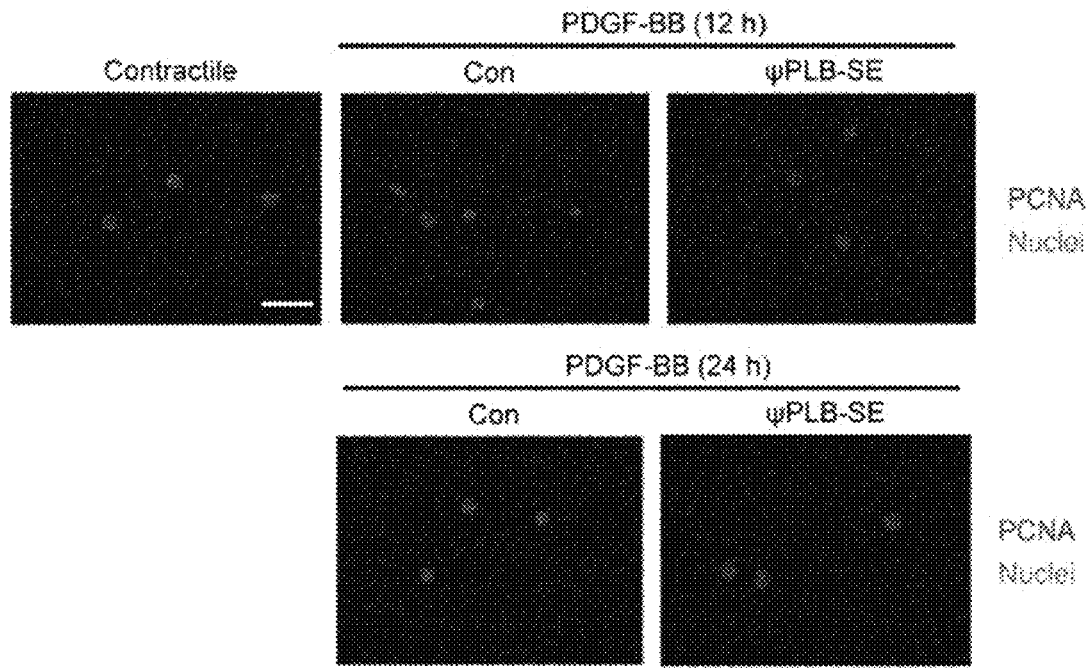
Figure 5D:
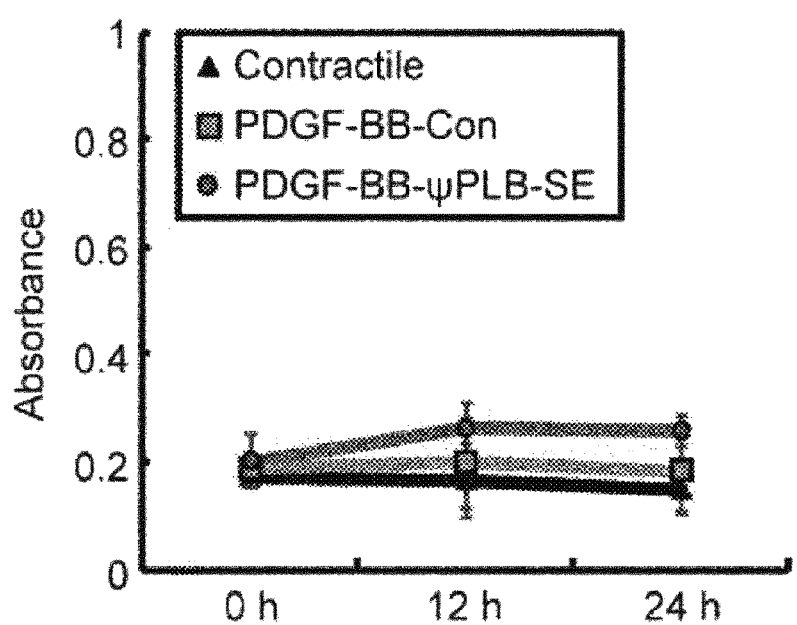
Figure 5E:
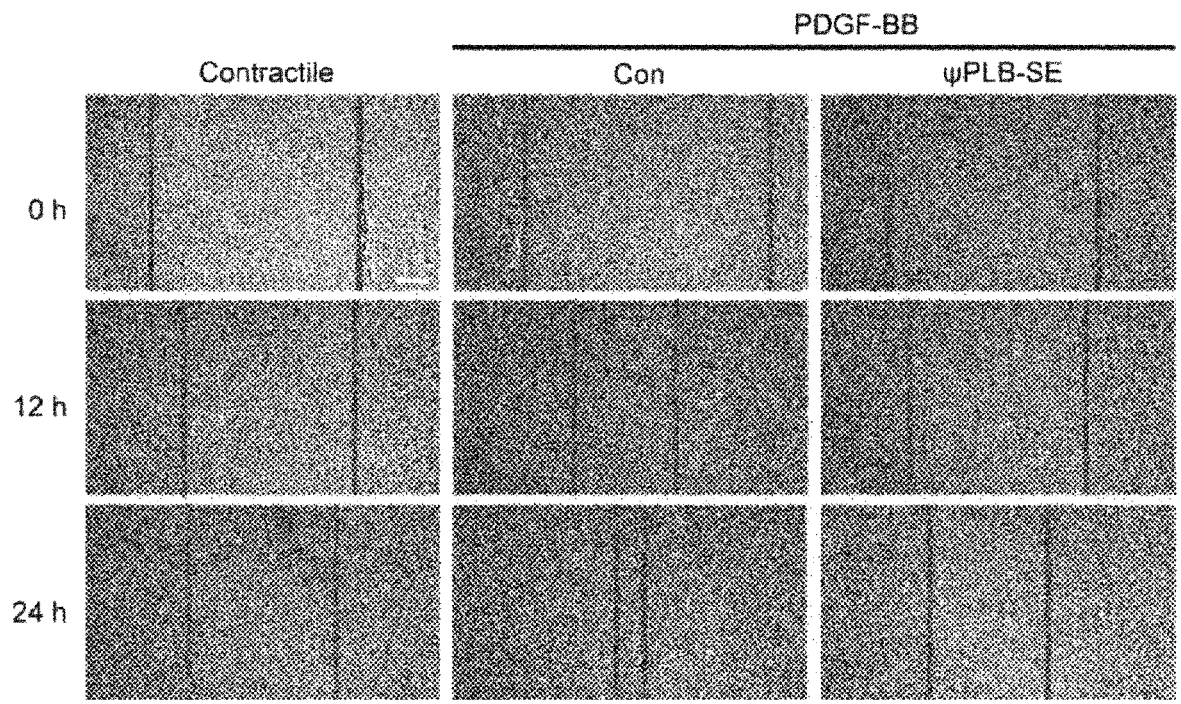
Figure 5F:
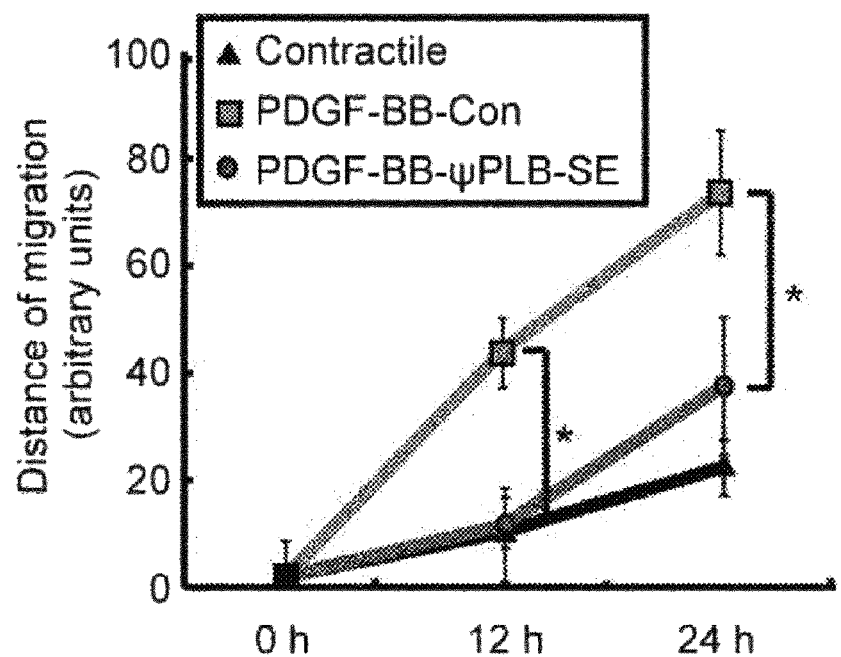

The $Ca^{2+}$ ionophore A23187 evoked the degradation of SERCA2a, but not SERCA2b, in human coronary smooth muscle cells (HCSMCs), indicating that the increased cytosolic $Ca^{2+}$ level triggers the degradation of SERCA2a. The effect of A23187 was completely blocked by MDL28170, indicating that calpain is involved in the degradation of SERCA2a in VSMCs upon the increase of the cytosolic $Ca^{2+}$ level. The $Ca^{2+}$-dependent degradation of SERCA2a was also completely inhibited by ψPLB-SE (FIGS. 4a-4b). The elevation of the cytosolic $Ca^{2+}$ level by A23187 was normalized by ψPLB-SE, but not by the calpain inhibitor (FIG. 4c). The cytosolic $Ca^{2+}$ level elevated under synthetic conditions was also decreased by ψPLB-SE (FIG. 4d). Taken together, these data suggest that ψPLB-SE inhibits the calpain-mediated degradation of SERCA2a by normalizing the elevated cytosolic $Ca^{2+}$ level in VSMCs under synthetic conditions.

5. ψPLB-SE Treats Pulmonary Arterial Hypertension of Rats

Figure 8A:
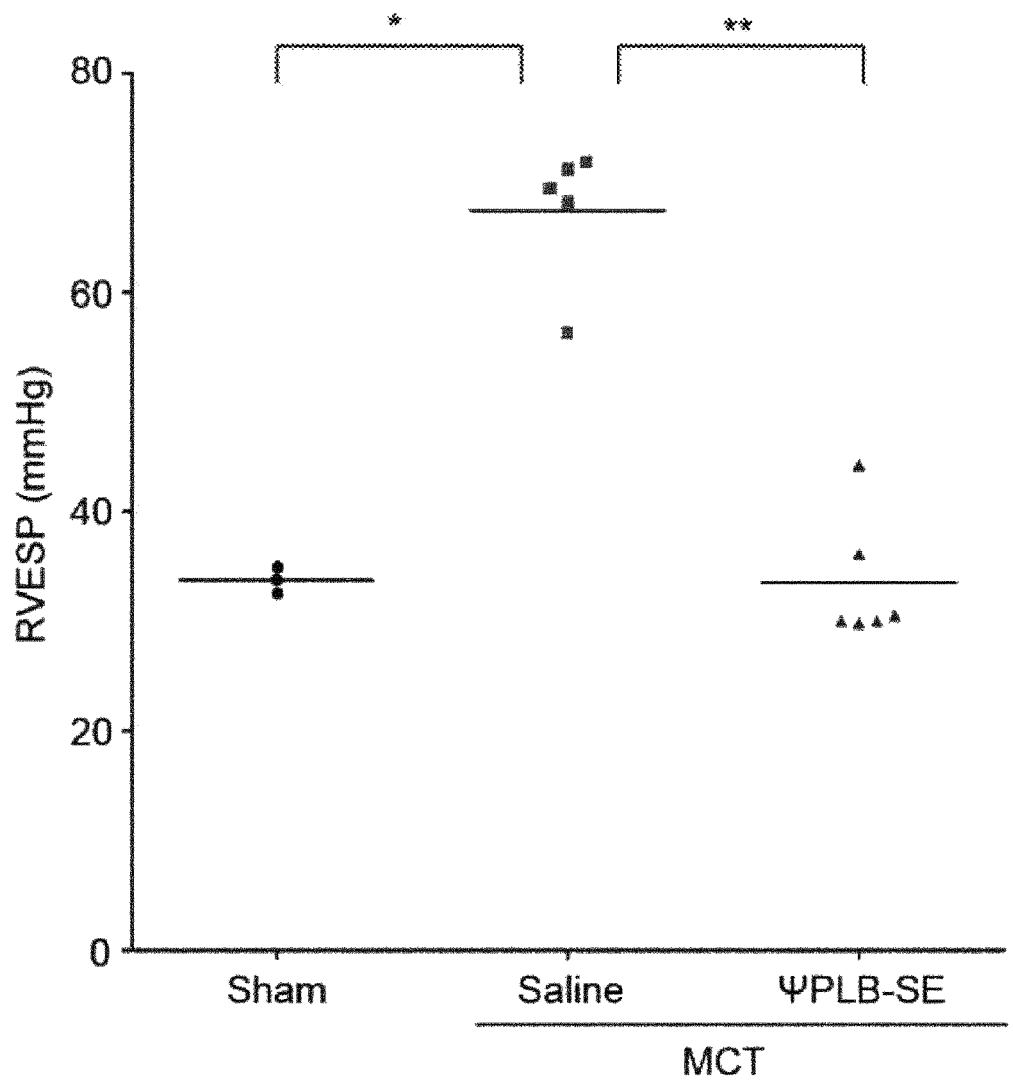
FIGS. 8a and 8b. These figures show an experiment in which rats were injected with 60 mg/kg MCT, and administered with the peptide (ψPLB-SE) via respiratory inhalation four times at intervals of one week, to investigate therapeutic effects. Four-week-old rats were subjected to right heart catheterization in an open chest state to measure right ventricular end-systolic pressure (RVESP), left ventricular end-systolic pressure (LVESP), right ventricular end-diastolic pressure (RVEDP), left ventricular end-diastolic pressure (LVEDP), and cardiac output (CO). (Sham n=3, MCT n=5, ψPLB-SE n=6; *, P<0.05 vs sham,)
Figures 8B, 9A:
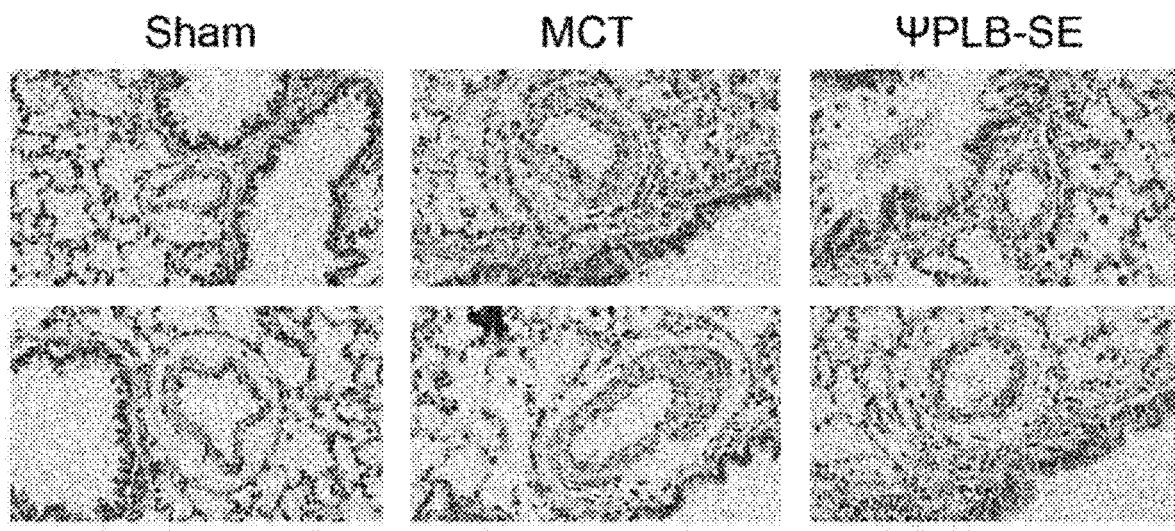
FIGS. 9a and 9b. In the same conditions as in FIGS. 8a-8b, (9a) the thickening of the pulmonary artery was checked through hematoxylin and eosin staining, and (9b) protein expression was quantitatively analyzed through western blotting using an antibody against GAPDH.
Figure 9B:
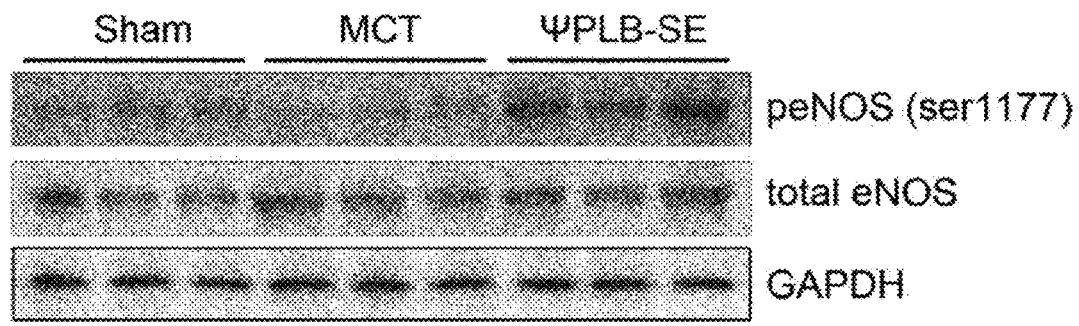
Figure 10A:
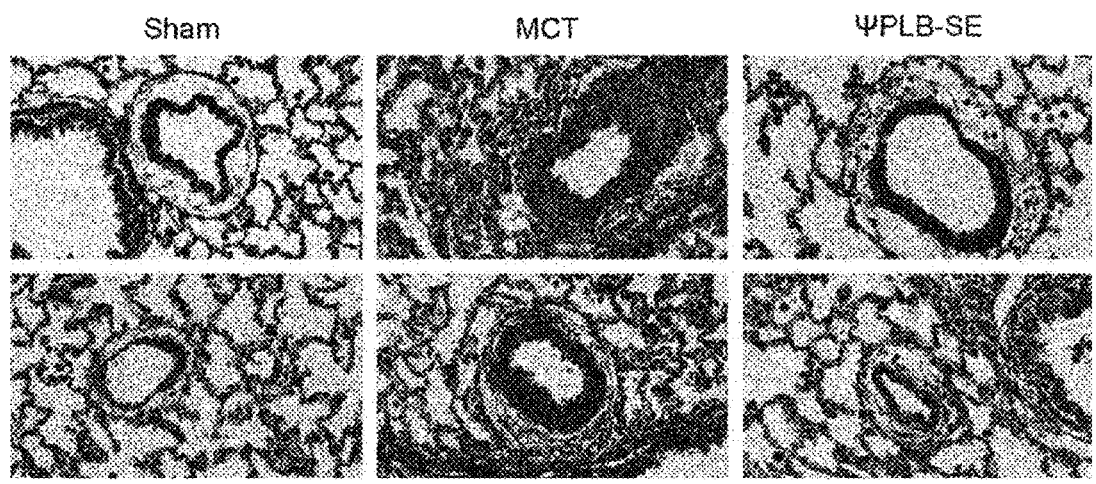
FIGS. 10a and 10b. In the same conditions as in FIGS. 8a-8b, (10a) the fibrosis extent of pulmonary artery adventitia was investigated through Masson-trichrome staining, and (10b) protein expression was quantitatively analyzed through western blotting using antibodies against vimentin, αSMA, and GAPDH (10b).
Figure 10B:
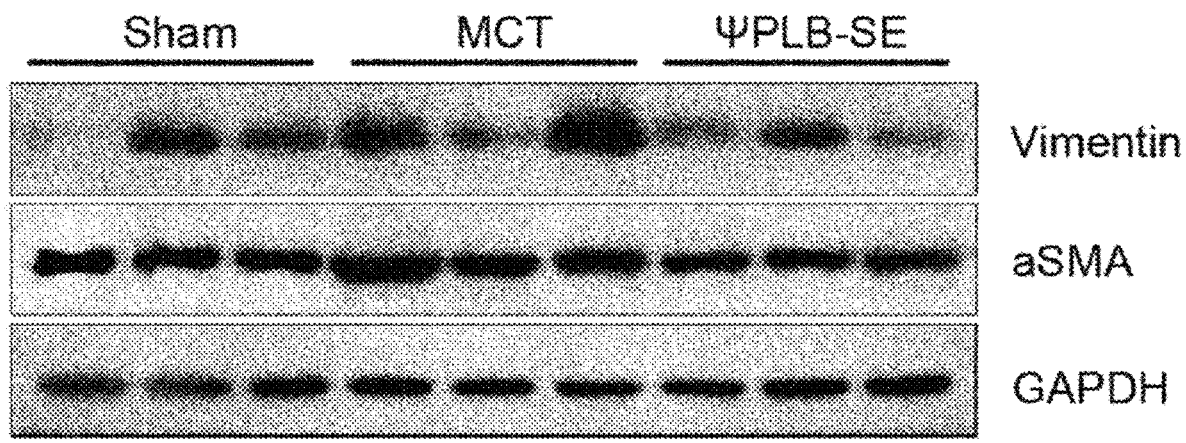
Figure 11A:
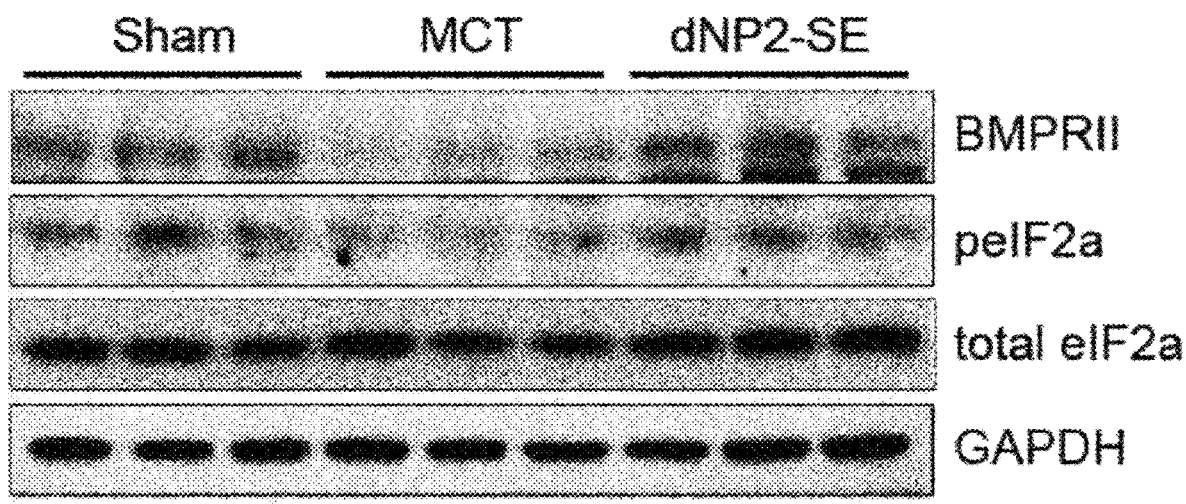
FIGS. 11a, 11b, 11c and 11d. In the same conditions as in FIGS. 8a-8b, (11a) protein expression was quantitatively analyzed through western blotting using antibodies against BMPR2, phospho-eIF2α, eIF2α, and GAPDH, and (11b-11d) the content degrees of inflammatory cytokines in pulmonary tissue were measured using a cytokine mixture kit. (Sham n=3, MCT n=4, ψPLB-SE n=6; *, P<0.05 vs sham; #, P<0.05 vs MCT)
Figure 11B:
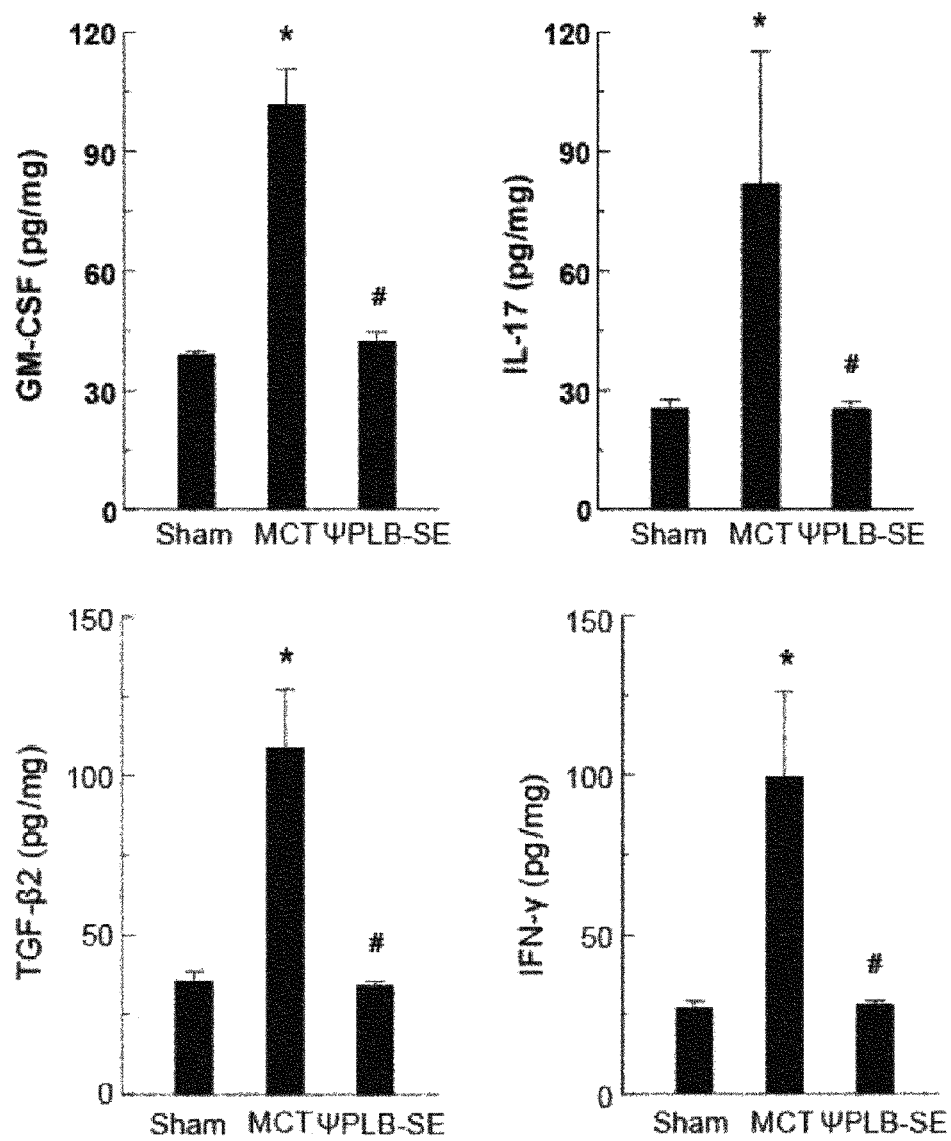
Figure 11C:
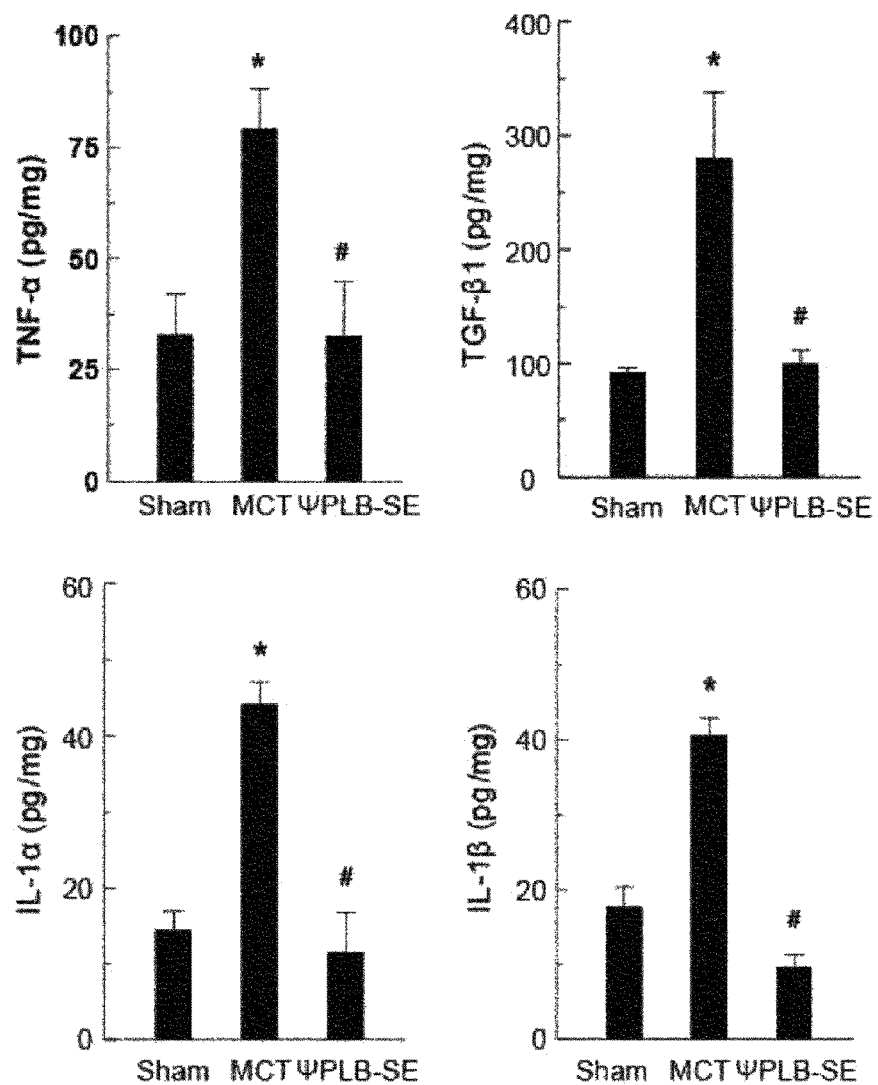
Figure 11D:
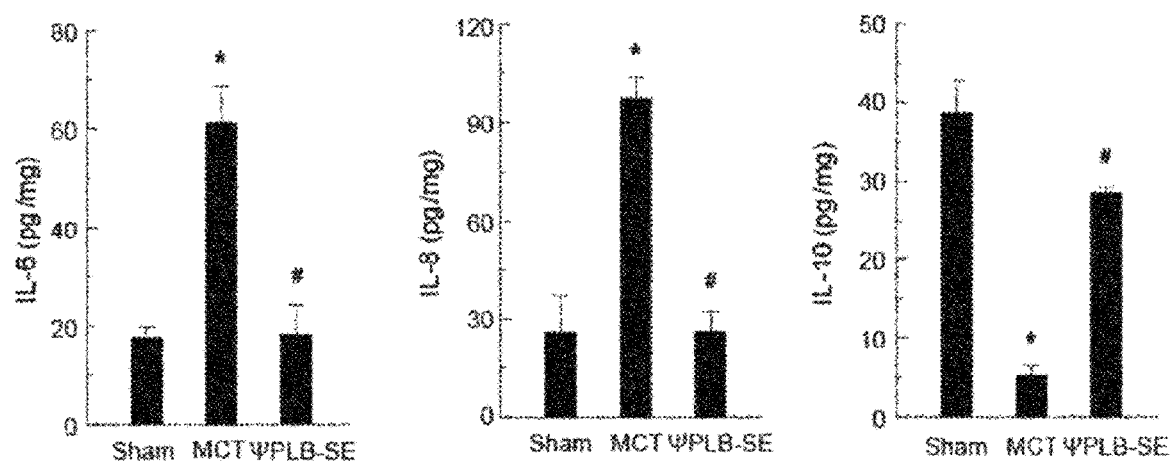

In the present invention, experiments were carried out to investigate whether the peptide had a therapeutic effect on pulmonary arterial hypertension through a similar or new mechanism. The rats were injected with monocrotaline (MCT) to induce pulmonary arterial hypertension, and administered with ψPLB-SE via respiratory inhalation once a week for a total of 4 weeks. The right ventricular end-systolic pressure was measured through right heart catheterization 4 weeks after the induction of pulmonary arterial hypertension. It could be confirmed from the blood pressure measurement results that the right ventricular end-systolic pressure was increased in the groups with pulmonary arterial hypertension induced through MCT (67.4±6.4 vs sham=33.7±1.7), and was lowered to the levels of the control group by the treatment with ψPLB-SE (33.5±5.8) (FIGS. 8a-8b). The characteristic phenotypes in pulmonary arterial hypertension include thickening of vascular walls due to abnormal proliferation of pulmonary artery endothelial cells and smooth muscle cells, increased fibrosis in vascular adventitia, inflammation occurring throughout pulmonary tissues and characterized by monocyte infiltration and increased cytokines, and the like [Thompson A A et al. (2017) Trends Mol Med 23(1): 31-45; Stenmark K R et al. (2011) Compr Physiol 1(1): 141-161; and Aihara K et al, (2012) Int J Vasc Med 2012:596796]. For the investigation the phenotypes of pulmonary arterial hypertension through histological study, the vascular thickening was investigated through hematoxylin and eosin staining in the pulmonary tissues obtained from the rats after blood pressure measurement, and as a result, it could be confirmed that the increase in vascular thickening shown in the group with induced pulmonary arterial hypertension was attenuated by the treatment with ψPLB-SE (FIG. 9a). In addition, through quantitative analysis of proteins obtained from pulmonary tissues, the increase in the eNOS phosphorylation level could confirm that the eNOS activity reduction shown characteristically in pulmonary arterial hypertension was increased by the treatment with ψPLB-SE (FIG. 9b). In addition, in order to investigate effects of ψPLB-SE on vascular adventitia fibrosis, pulmonary tissues was subjected to Masson-Trichrome staining to investigate the extent of collagen deposition. It could be confirmed that the fibrosis extent increased due to pulmonary arterial hypertension was reduced through ψPLB-SE (FIG. 10a). It was also confirmed through protein quantitative analysis that the increases in the expression of vimentin and α-SMA, known as fibrosis target genes, were attenuated through ψPLB-SE treatment (FIG. 10b). Last, in order to verify the inflammation reduction effect of ψPLB-SE, the expression degree of BMPR2, an inflammation mechanism-related protein, and the phosphorylation level of eIF2α, a signaling system substance associated with BMPR2, were investigated, and as a result, it was confirmed that the reduced expression and activity in pulmonary arterial hypertension were restored by the treatment with ψPLB-SE (FIG. 11a). As a result of measurement of actual cytokine levels, it was confirmed that the proinflammatory cytokines, such as GM-CSF, TNF-α, IL-17, IL-1β, IL-6, and TGF-β, were increased in pulmonary arterial hypertension, and restored to nearly to the normal levels thereof by the treatment with ψPLB-SE (FIGS. 11b-11d).

6. ψPLB-SE Treats Pulmonary Arterial Hypertension of Mice

Figure 12A:
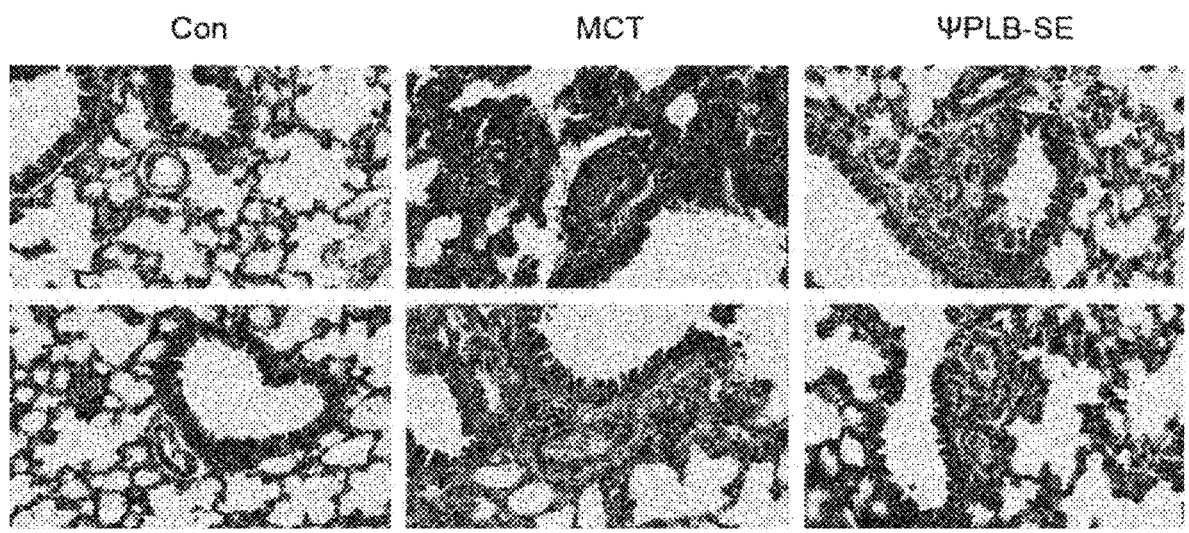
FIGS. 12a and 12b. These figures show an experiment in which mice were injected with 600 mg/kg MCT, and administered with the peptide (ψPLB-SE) via respiratory inhalation four times at intervals of one week from the second week, to investigate therapeutic effects. (12a) The thickening degree of the pulmonary artery was checked through hematoxylin and eosin staining. (12b) Protein expression was quantitatively analyzed through western blotting using antibodies against phospho-eNOS, total eNOS, SERCA2a, and GAPDH.
Figure 12B:
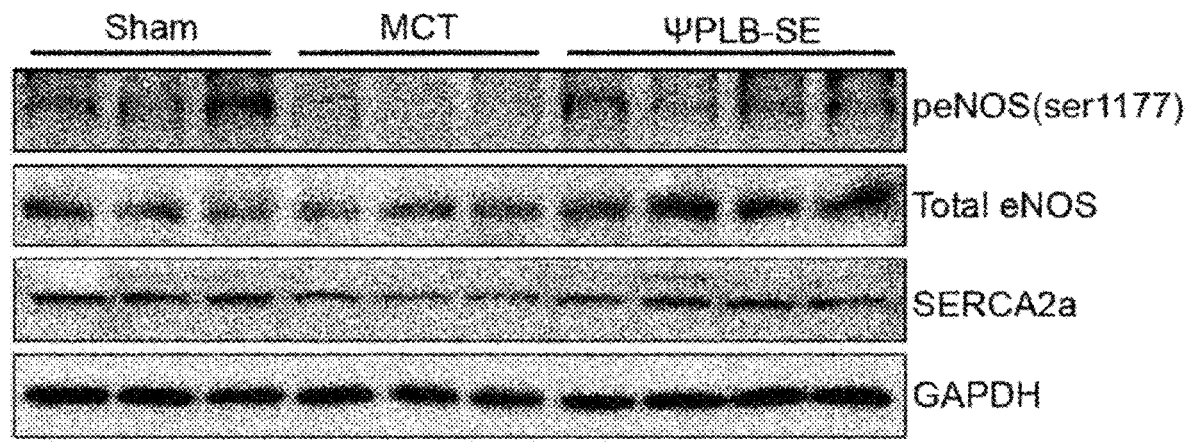
Figure 13A:
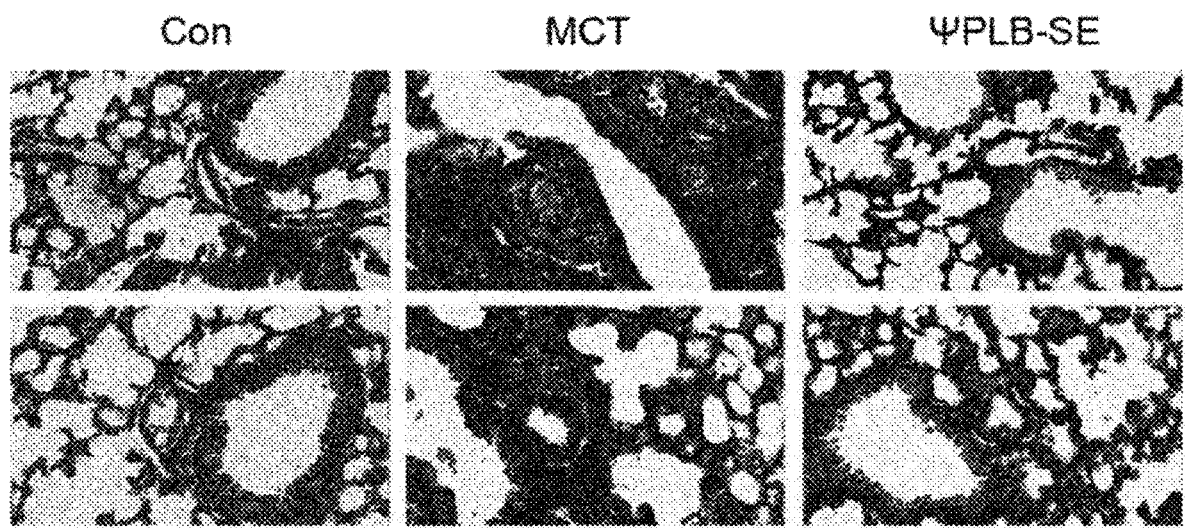
FIGS. 13a, 13b and 13c. In the same conditions as in FIGS. 12A-12B, (13a) the fibrosis extent of pulmonary artery adventitia was investigated through Masson-trichrome staining, and (13b) protein expression was quantitatively analyzed through western blotting using vimentin, αSMA, and GAPDH. In addition, (13c) mRNA expression levels of TGF-β1, Collagen 1, and αSMA were quantitatively analyzed through real-time quantitative RT-PCR.
Figure 13B:
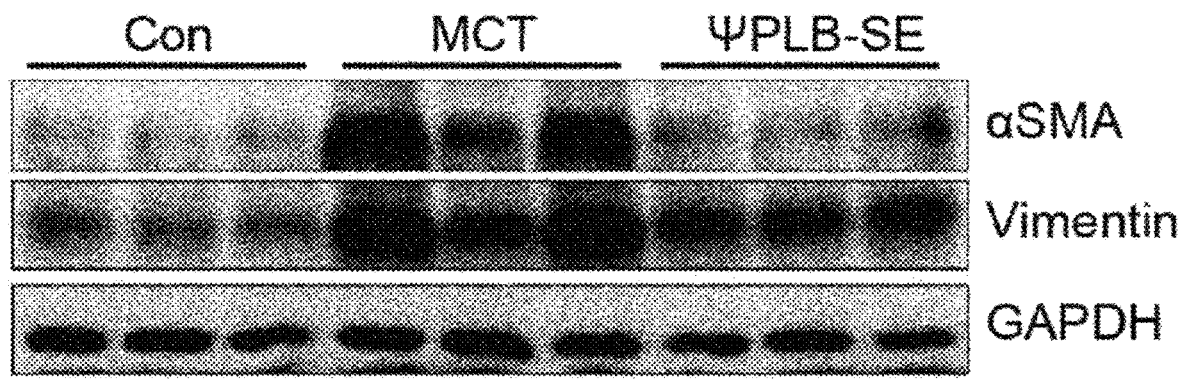
Figure 13C:
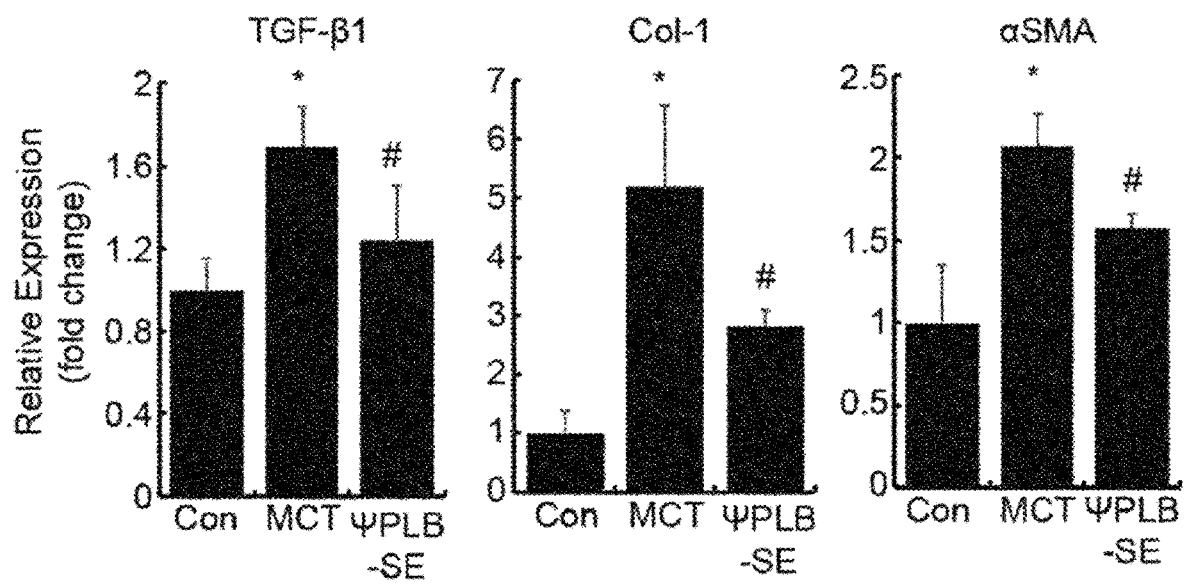
Figure 14A:
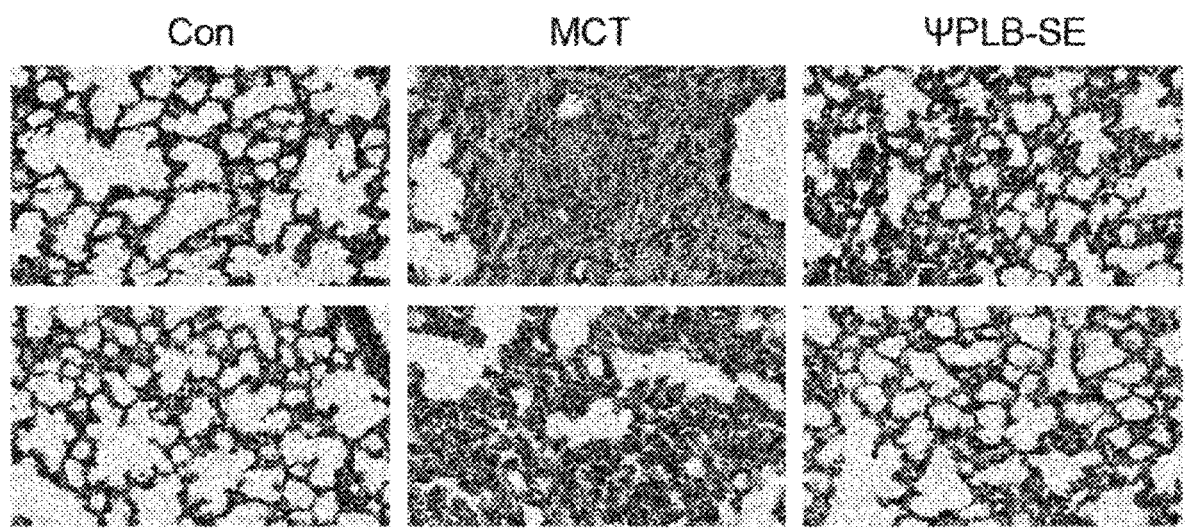
FIGS. 14a and 14b. In the same conditions as in FIGS. 12a-12b, (14a) the inflammation degree, such as monocyte infiltration, in the entire pulmonary tissue, was investigated through hematoxylin and eosin staining, and (14b) mRNA expression levels of TNF-α, IL-1β, F4/80, and MCP-1 were quantitatively analyzed through real-time quantitative RT-PCR. (sham, MCT, ψPLB-SE, n=4; *, P<0.05 vs sham; #, P<0.05 vs MCT)
Figure 14B:
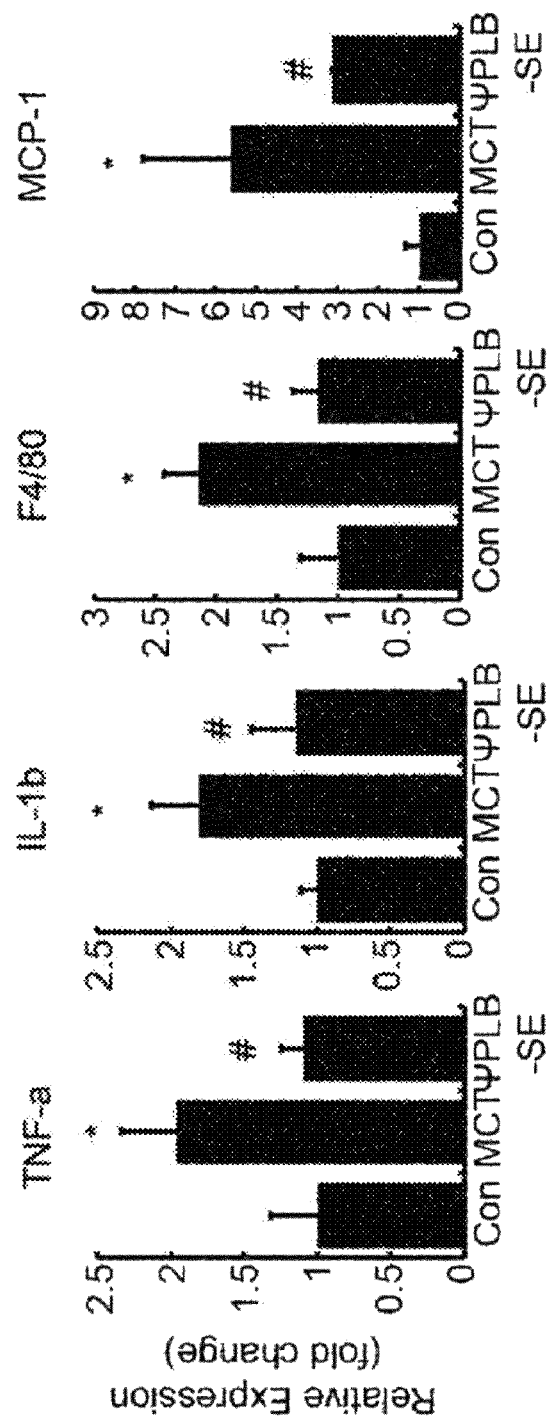
Figure 15A:
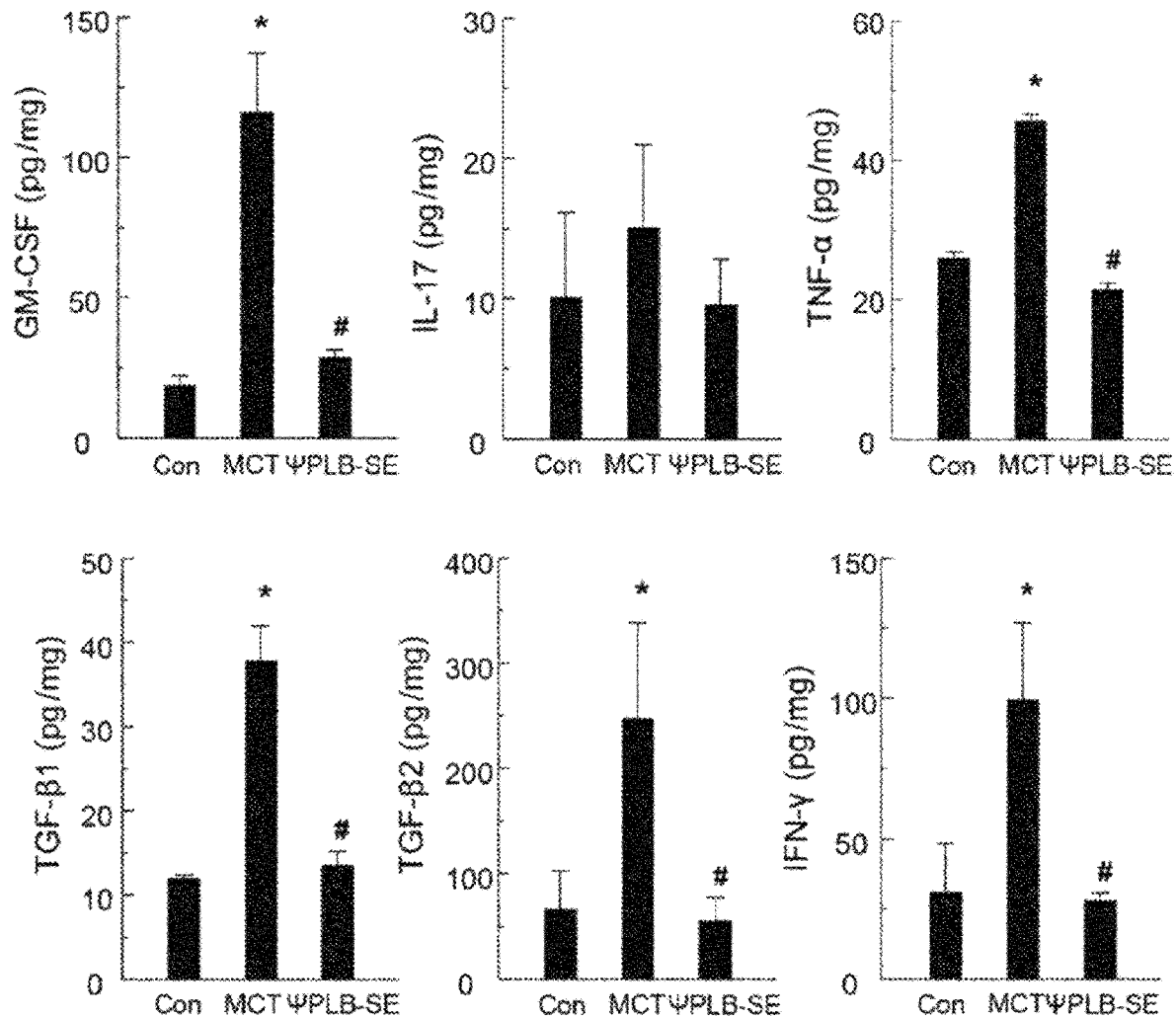
FIGS. 15a and 15b. In the same conditions as in FIGS. 12a-12b, the content degrees of inflammatory cytokines in pulmonary tissue were measured using a cytokine mixture kit. (Sham n=3, MCT n=4, ψPLB-SE n=6; *, P<0.05 vs sham; #, P<0.05 vs MCT)
Figure 15B:
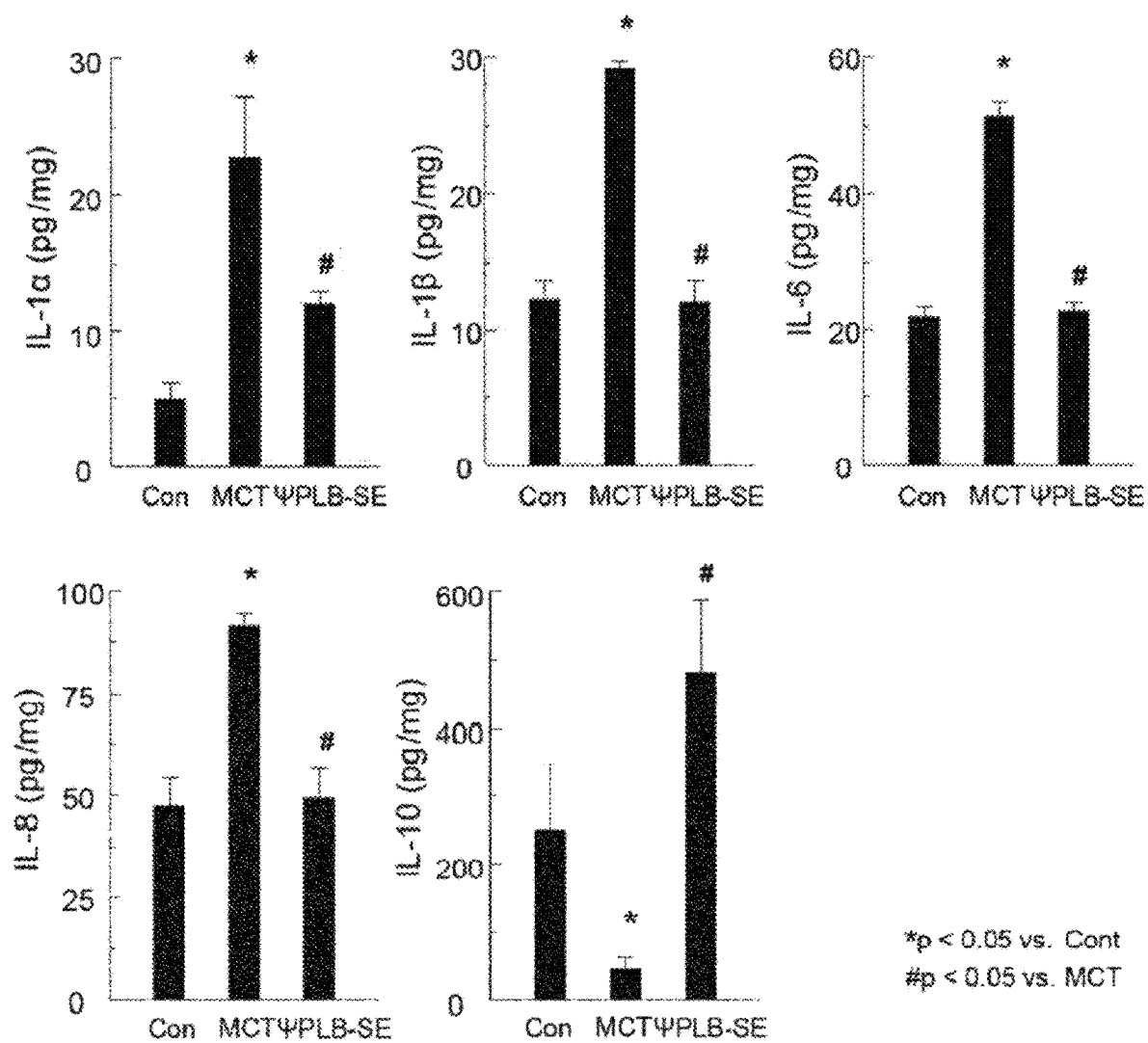

The restoration effect of the peptide, confirmed in rats, was investigated in mice models as another type of animal models. Mice were injected with monocrotaline (MCT) to induce pulmonary arterial hypertension, and administered with ψPLB-SE via respiratory inhalation from the second week once a week for a total of 4 weeks. The same experiments excluding blood pressure measurement were carried out in mouse pulmonary tissues 4 weeks after the administration of ψPLB-SE. First, the vascular thickening in the pulmonary tissues obtained from the mice was checked through hematoxylin and eosin staining. It was confirmed that the increase in vascular thickening, shown in the group with induced pulmonary arterial hypertension, was attenuated by the treatment with ψPLB-SE (FIG. 12a). In addition, through quantitative analysis of proteins obtained from pulmonary tissues, the increase in eNOS phosphorylation level could confirm that the eNOS activity reduction shown characteristically in pulmonary arterial hypertension was increased by the treatment with ψPLB-SE. It was also confirmed that the expression level of SERCA2a was increased by the treatment with ψPLB-SE (FIG. 12b). Then, in order to investigate the effect of ψPLB-SE on vascular adventitia fibrosis, the pulmonary tissues was subjected to Masson-trichrome staining to investigate the extent of collagen deposition. It was confirmed that the fibrosis extent increased due to pulmonary arterial hypertension was attenuated through ψPLB-SE (FIG. 13a). It was also confirmed through protein quantitative analysis that the increases in the protein and mRNA expression of TGF-β, Collagen 1, vimentin, and α-SMA, known as fibrosis target genes, were attenuated through ψPLB-SE treatment (FIGS. 13b-13c). Last, in order to verify the inflammation reduction effect of ψPLB-SE, the monocyte infiltration in the pulmonary tissues was investigated by hematoxylin and eosin staining and the mRNA levels of inflammation-related cytokines were measured, and as a result, it was confirmed that the increase in monocyte infiltration in the pulmonary arterial hypertension was attenuated through ψPLB-SE treatment (FIG. 14a), and it was confirmed that the mRNA expression levels of TNF-α, IL-17, IL-1β, F4/80, and MCP-1 as inflammation-related target genes were reduced through ψPLB-SE treatment (FIG. 14b). Last, the levels of inflammation-related cytokines were measured in the pulmonary tissues in the same manner as in the rats, and as a result, it was confirmed that proinflammatory cytokines, such as GM-CSF, TNF-α, IL-17, IL-1β, IL-6, and TGF-β, were increased in pulmonary arterial hypertension, and restored to nearly to the normal levels thereof by the treatment with ψPLB-SE (FIGS. 15a-15b).

7. ψPLB-SE Increases eNOS Activity Through PP1 in Pulmonary Arterial Endothelial Cells (PAECs)

Figure 16A:
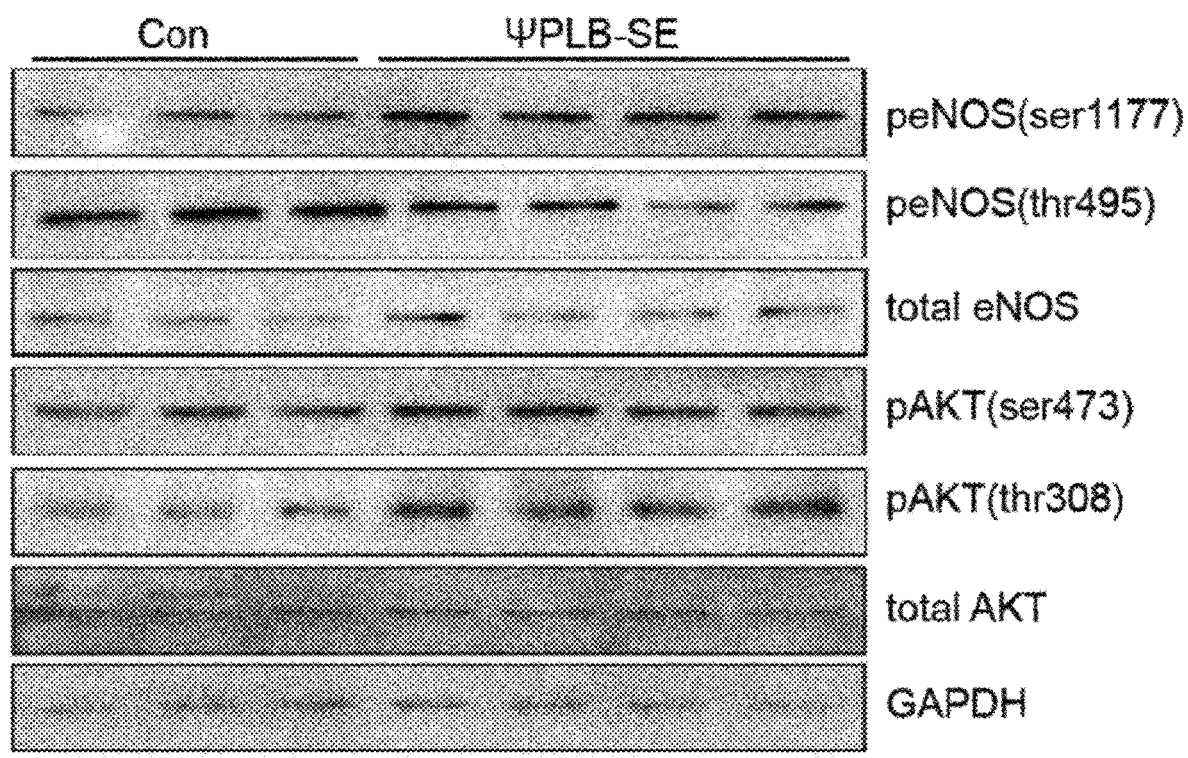
FIGS. 16a, 16b and 16c. (16a-16b) PAECs were treated with 3 μM ψPLB-SE for 1 hour, and protein expression was quantitatively analyzed through western blotting using antibodies against Phospho-eNOS (ser1177), total eNOS, phospho-Akt (Ser473, Thr308), total Akt, and GAPDH. (16c) The pulmonary tissue lysate was subjected to immunoprecipitation using PP1 antibody to investigate the interactions of PP1 with eNOS and Akt depending on the presence or absence of the treatment with ψPLB-SE using respective antibodies therefor.
Figure 16B:
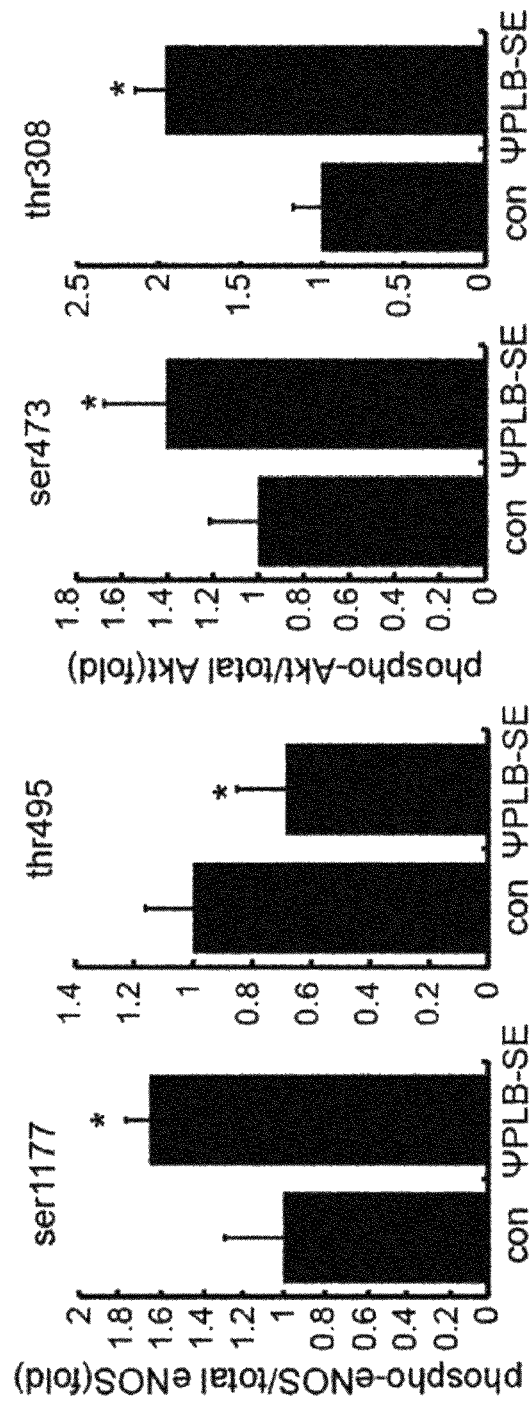
Figure 16C:
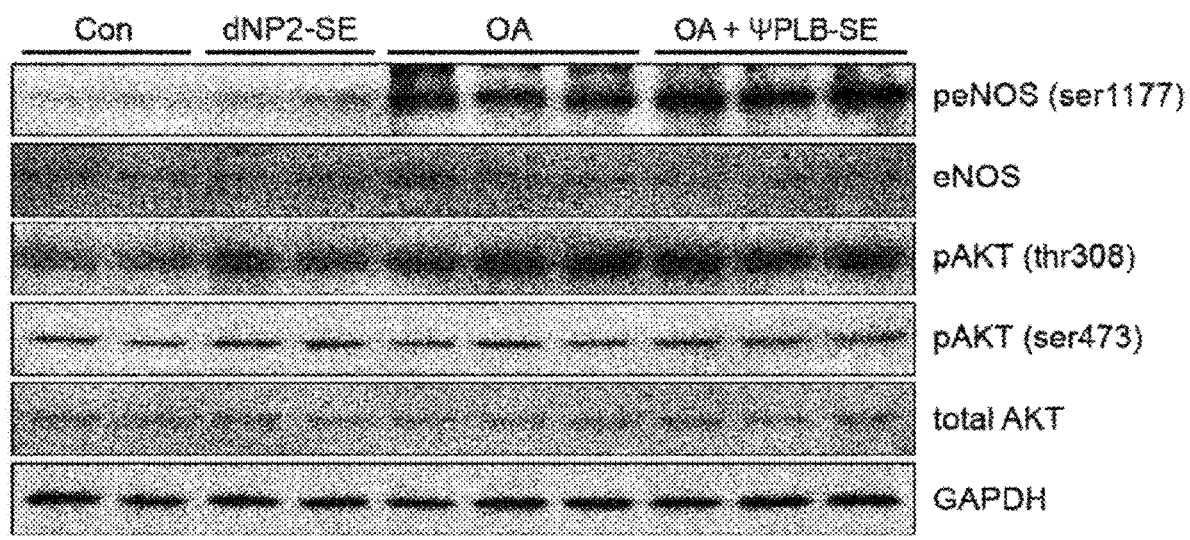

It is widely well known that the decreased eNOS activity due to dysfunction of endothelial cells reduces the production of NO as a vasodilator in pulmonary arterial hypertension [Giaid A et al. (1995) N Engl J Med 333: 214-221]. In the results of confirmation through histological experiments by the present inventors, the phosphorylation level of eNOS is increased by the treatment with ψPLB-SE, and studies for developing a new mechanism thereof was conducted. First, for the investigation of eNOS activity increase by ψPLB-SE in PAECs, the PAECs were treated with 3 μM ψPLB-SE for 1 hour, and as a result, the phosphorylation of serine 1177 as an eNOS activity phosphorylation reside was increased and the phosphorylation of threonine 495 as an inhibitory phosphorylation residue was reduced. It was also confirmed that the phosphorylation of the serine 473 residue and the threonine 308 residue showing the activity of Akt, a well-known high-order substance of eNOS [Michell B J et al. (1999) Curr Biol 9(15): 845-848] was increased (FIGS. 16a-16b). Considering that ψPLB-SE is a substance invented as a PP1 inhibitor, in order to investigate whether these results were actually attained through the PP1 inhibitory effect, pulmonary arterial endothelial cells (PAECs) were treated with 100 nM okadaic acid (OA) as a typical PP1 inhibitor, followed by the treatment with ψPLB-SE, to investigate the phosphorylation of eNOS and Akt. As a result, a synergistic effect that the phosphorylation of Akt of eNOS was increased by OA treatment and the phosphorylation was further increased by peptide treatment was confirmed. These results show that ψPLB-SE regulates the activity of eNOS and Akt by inhibiting PP1 (FIG. 16c).

Figure 17A:
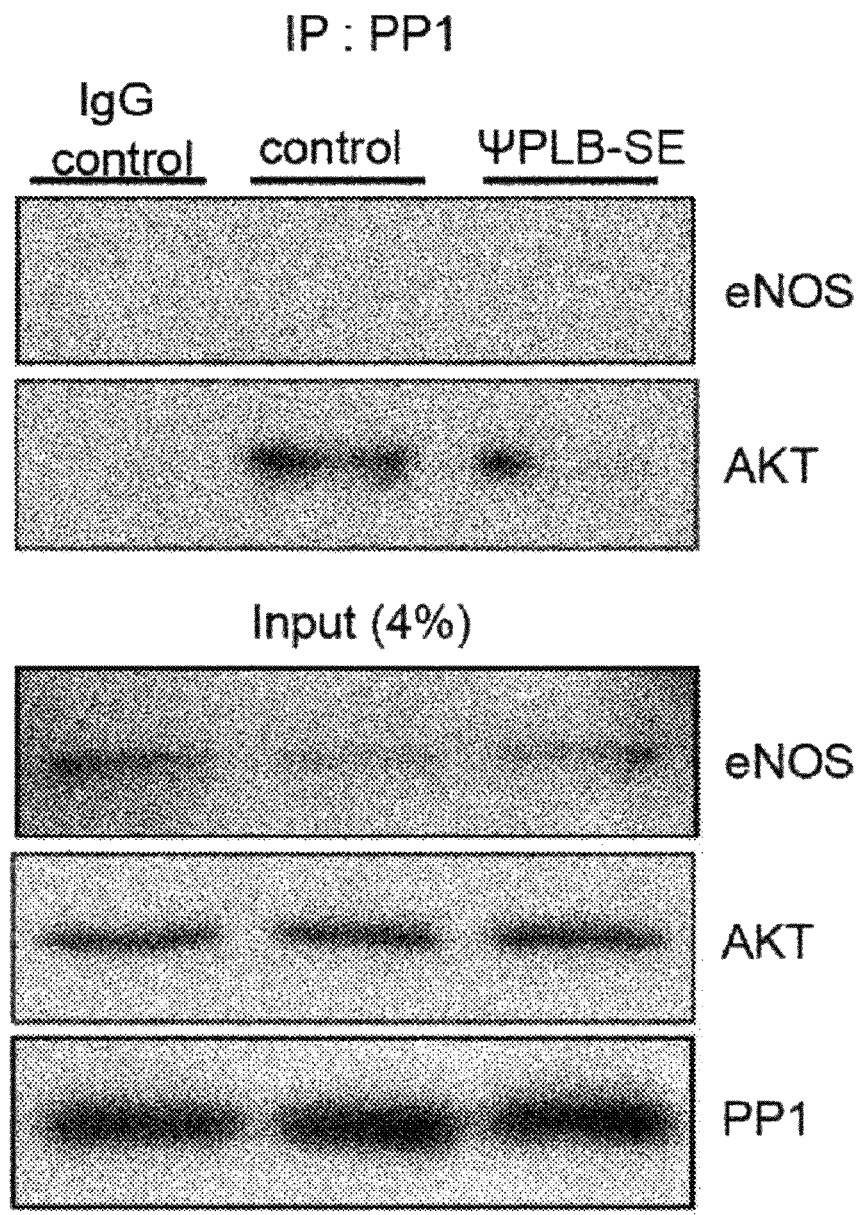
FIGS. 17a, 17b and 17c. (17a) PAECs were treated with 50 μM LY294002, a PI3K inhibitor, for 24 hours, and then treated with 3 μM ψPLB-SE for 1 hour. Protein expression was quantitatively analyzed through western blotting using antibodies against Phospho-eNOS (ser1177), total eNOS, phospho-Akt (Ser473, Thr308), total Akt, and GAPDH. (17b) PAECs were treated with 10 μM inhibitor IV, an Akt inhibitor, for 2 hours, and then treated with 3 μM ψPLB-SE for 1 hour. Protein expression was quantitatively analyzed through western blotting using antibodies against total eNOS and GAPDH. (17c) PAECs were treated with 100 nM OA, a PP1 inhibitor, for 24 hours, and then treated with 3 μM ψPLB-SE for 1 hour. Protein expression was quantitatively analyzed through western blotting using antibodies against Phospho-eNOS (ser1177), total eNOS, phospho-Akt (Ser473, Thr308), total Akt, and GAPDH.
Figure 17B:
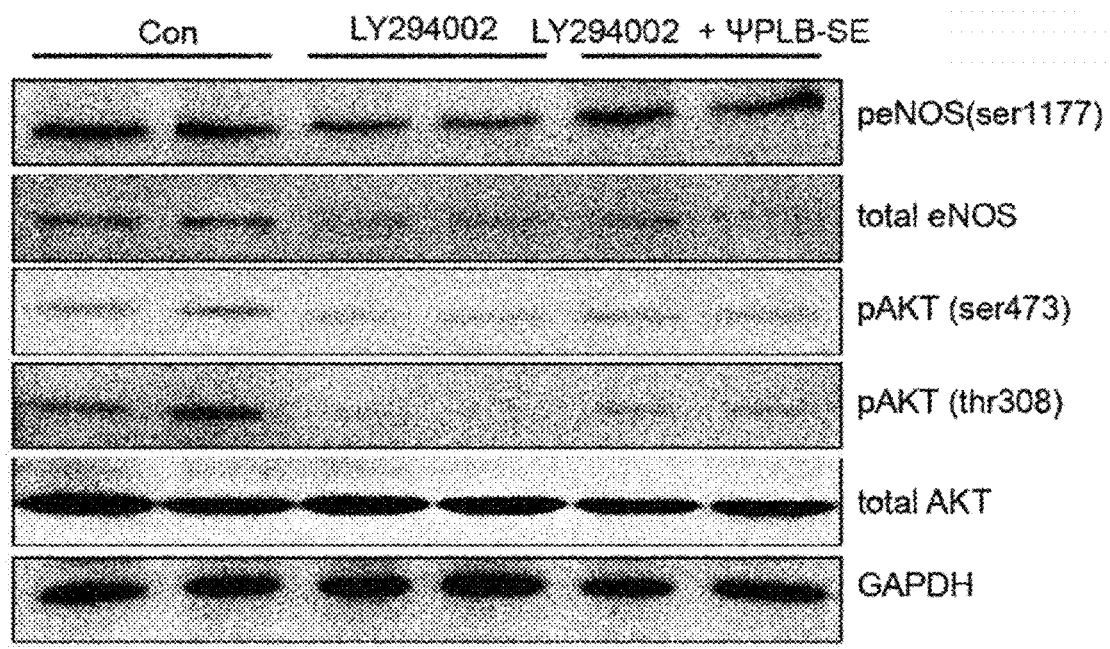
Figure 17C:
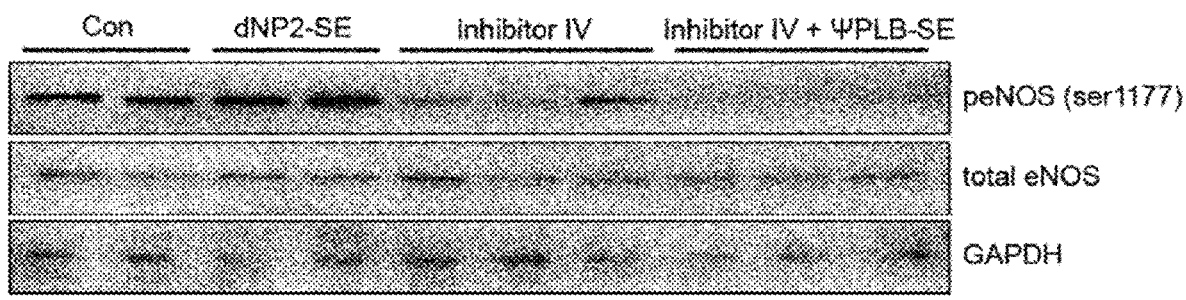

In order to intensively investigate the interactions of PP1 with eNOS and Akt, the pulmonary tissue lysate was subjected to immunoprecipitation using an antibody against PP1, and the effects of ψPLB-SE on the interactions were investigated by adding ψPLB-SE upon the precipitation. As a result, it was confirmed that Akt, unlike eNOS, had a direct interaction with PP1 and such an interaction was attenuated by the treatment with ψPLB-SE. These results show that ψPLB-SE inhibits the dephosphorylation of Akt and eNOS by inhibiting the interaction of PP1 and Akt (FIG. 17a). The activation of eNOS through the inhibition of the interaction between PP1 and Akt was supplemented through the experiments on the inhibition of the high-order kinase of Akt. The phosphorylation increases of Akt and eNOS due to the inhibition of dephosphorylation were investigated by offsetting the phosphorylation conditions of Akt through the treatment with LY294002, which is an inhibitor of phosphoinositide-3-kinase (PI3K), a known high-order kinase of Akt, at a concentration of 50 µM, followed by ψPLB-SE treatment. As a result, the phosphorylation of eNOS and Akt reduced due to PI3K inhibition was increased by the treatment with ψPLB-SE (FIG. 17b). Last, in order to determine whether the effects of ψPLB-SE treatment were actually exhibited through Akt, the effects on the phosphorylation of eNOS was investigated by the treatment with Inhibitor IV, an Akt inhibitor, at a concentration of 10 µM and then the treatment with ψPLB-SE. As a result, it was confirmed that the eNOS phosphorylation reduced by the Akt inhibitor did not increase regardless of the treatment with ψPLB-SE (FIG. 17c). These results indicate that the eNOS activation effect of ψPLB-SE was exhibited by inhibiting the interaction of PP1 and Akt to prevent Akt dephosphorylation and activating Akt.

8. ψPLB-SE Regulates SERCA2a Activity Through PP1 to Inhibit Cell Proliferation in Pulmonary Arterial Smooth Muscle Cells (PASMCs)

The abnormal proliferation of pulmonary arterial smooth muscle cells (PASMCs) due to the dysfunction of endothelial cells is a factor that plays a decisive role in increasing the pulmonary artery pressure in pulmonary arterial hypertension. The present inventors confirmed through the previous studies that ψPLB-SE inhibited abnormal proliferation by regulating SERCA2a activity in vascular smooth muscle cells isolated from rats. In order to investigate the same phenomenon in pulmonary arterial smooth muscle cells, a synthetic phenotype proliferated in a high concentration of serum (0.1% FBS) was induced compared with a contractile phenotype induced in a low concentration of serum (10% FBS). It could be confirmed that the reduced phosphorylation of the serine 16 residue of phospholamban in the synthetic phenotype was restored by the treatment with ψPLB-SE (FIG. 18a), and as a result of measurement of SERCA2a activity through $Ca^{2+}$ uptake assay in the same conditions, it was confirmed that the SERCA2a activity reduced in the synthetic phenotype was restored by the treatment with ψPLB-SE (FIG. 18b). These results are consistent with the results of the previous studies by the present inventors, and indicate that ψPLB-SE can also regulate the activity of SERCA2a in pulmonary arterial smooth muscle cells.

Figure 18A:
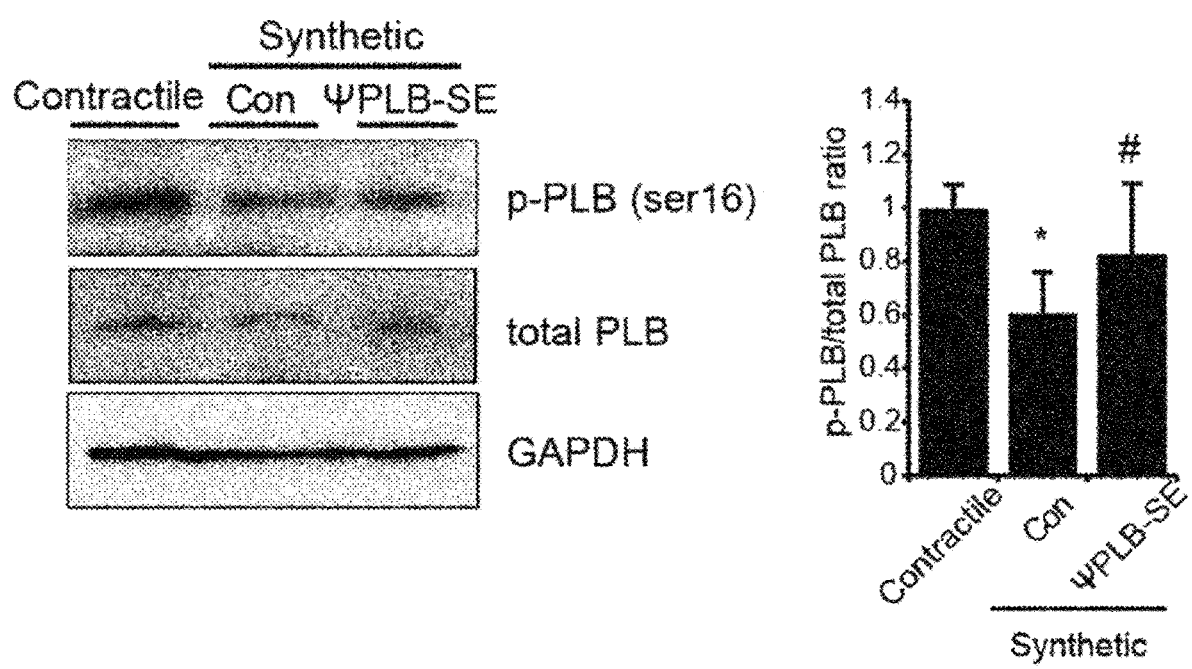
FIGS. 18a and 18b. PASMCs were incubated in DMEM supplemented with 0.1% (v/v) FBS for 3 days to induce a contractile phenotype, followed by incubation in DMEM supplemented with 10% (v/v) FBS for 3 days to induce a synthetic phenotype in the presence of 3 μM ψPLB-SE. (18a) Protein expression was quantitatively analyzed through western blotting using antibodies against phospho-PLB (ser16), total PLB, and GAPDH. Data are expressed as the means±SD (n=3~4; *, P<0.05 vs contractile; #, P<0.05 vs Synthetic-con). (18b) SERCA2a activity was measured through the calcium uptake assay.
Figure 18B:
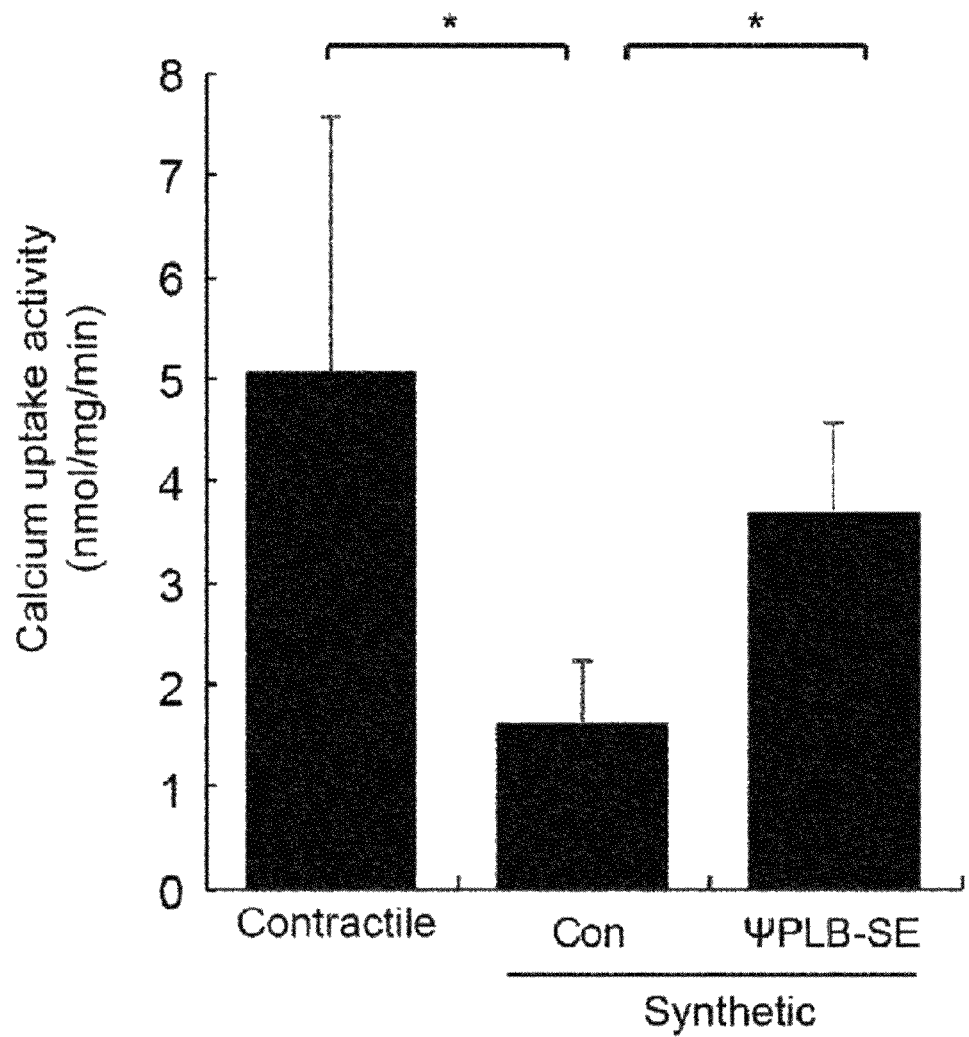
Figure 19A:
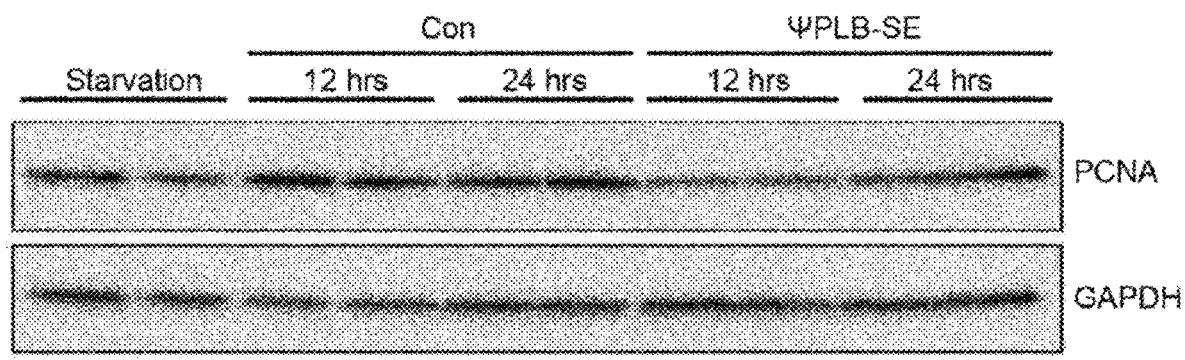
FIGS. 19a and 19b. PASMCs were subjected to the induction of a contractile phenotype in DMEM supplemented with 0.1% (v/v) FBS for 3 days, and then treated with 3 μM dNP2 for 24 hours. (19a) Protein expression was quantitatively analyzed through western blotting using antibodies against PCNA and GAPDH 12 and 24 hours after the treatment. (19b) Cell proliferation assay was performed using EZ-CyTox cell viability assay kit.
Figure 19B:
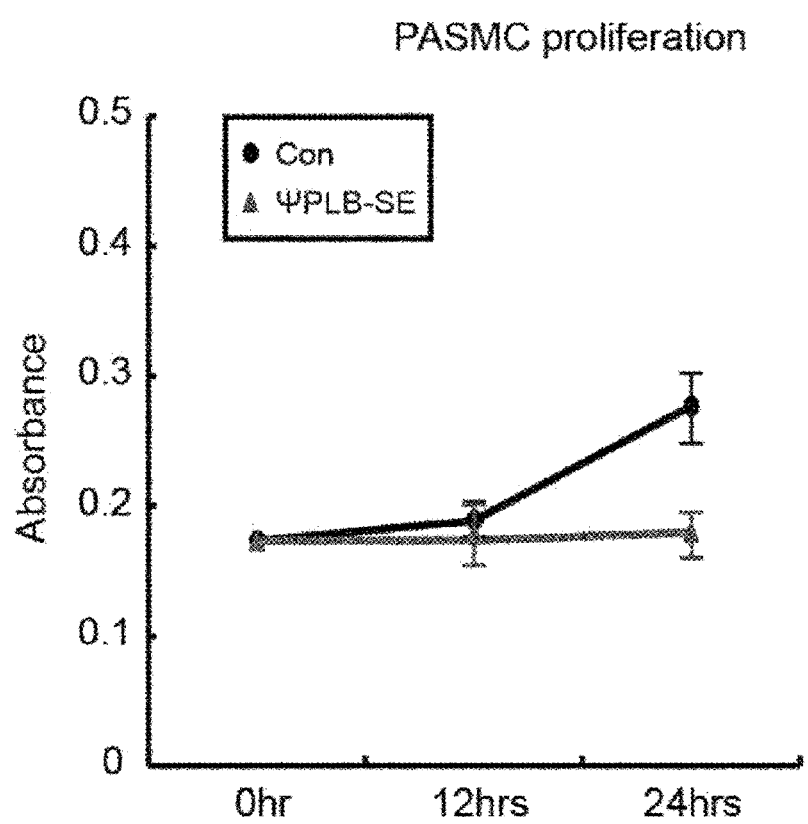

In order to investigate whether ψPLB-SE actually prevents the proliferation of pulmonary arterial smooth muscle cells through the regulation of SERCA2a activity, the expression of PCNA, a cell proliferation-related representative gene, was investigated in the conditions of FIGS. 18a-b and the cell proliferation assay was performed. As a result, it was confirmed that the expression of PCNA increased through synthetic phenotype induction was attenuated by the treatment with ψPLB-SE (FIG. 19a), and the effect of actually inhibiting cell proliferation was confirmed through the cell proliferation assay experiment (FIG. 19b). These results indicate that ψPLB-SE can inhibit abnormal proliferation of smooth muscle cells, which corresponds to a characteristics shown in pulmonary arterial hypertension.

9. ψPLB-SE Effects are not Affected by the Type and Form of Cell Penetrating Peptide (CPP)

Figure 20A:
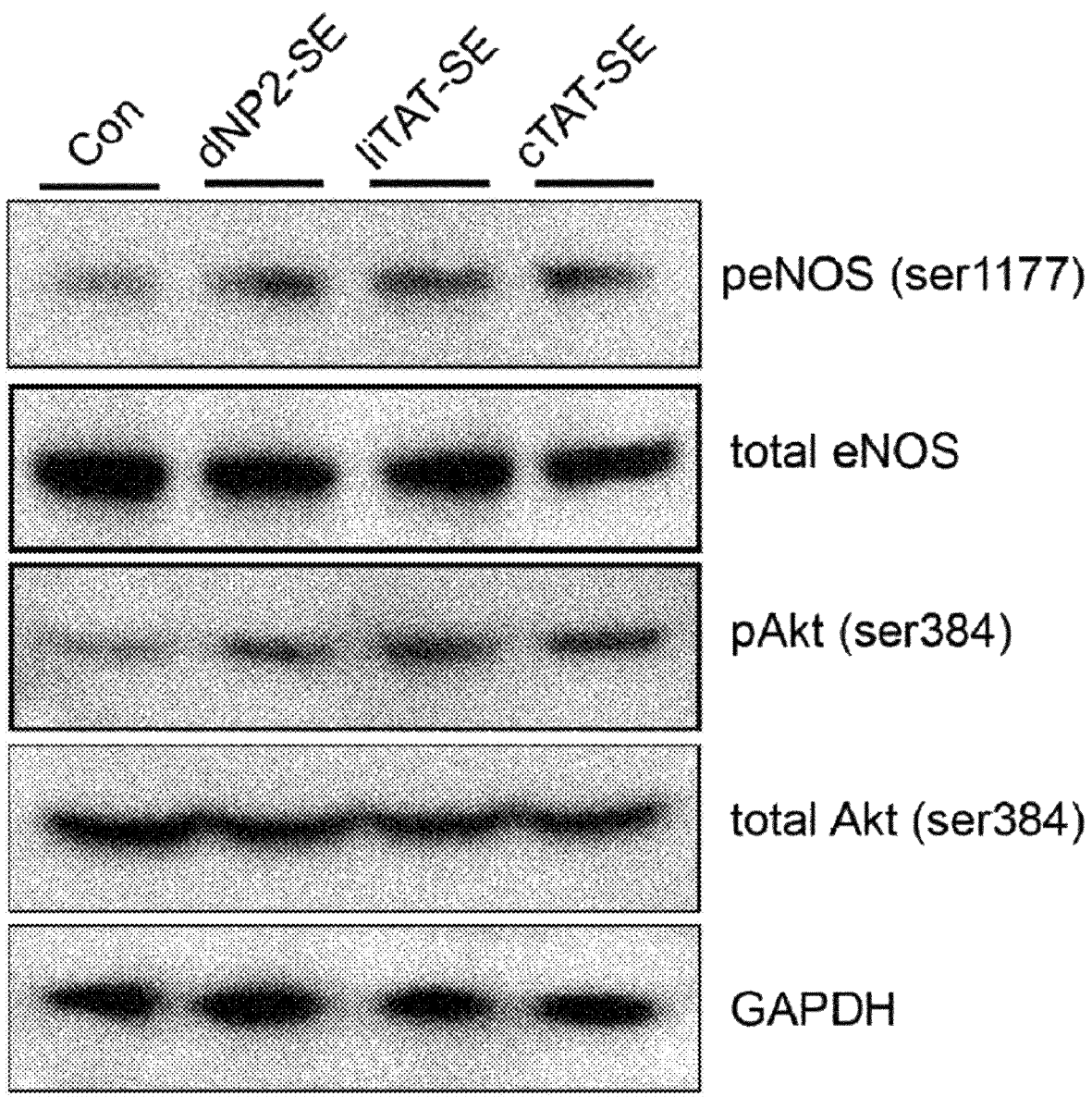
FIGS. 20a and 20b. (20a) PAECs were treated with 3 μM ψPLB-SE of three types (dNP2, linear TAT, cyclic TAT) for 1 hour, and protein expression was quantitatively analyzed through western blotting using antibodies against phospho-eNOS, eNOS, phospho-Akt, and Akt. (20b) In the same conditions as in FIG. 18, PASMCs were incubated in the presence of 3 μM ψPLB-SE of three types (dNP2, linear TAT, cyclic TAT), and protein expression was quantitatively analyzed through western blotting using antibodies against Phospho-PLB (ser16), total PLB, and GAPDH. (liTAT=linear TAT, cTAT=cyclic TAT)
Figure 20B:
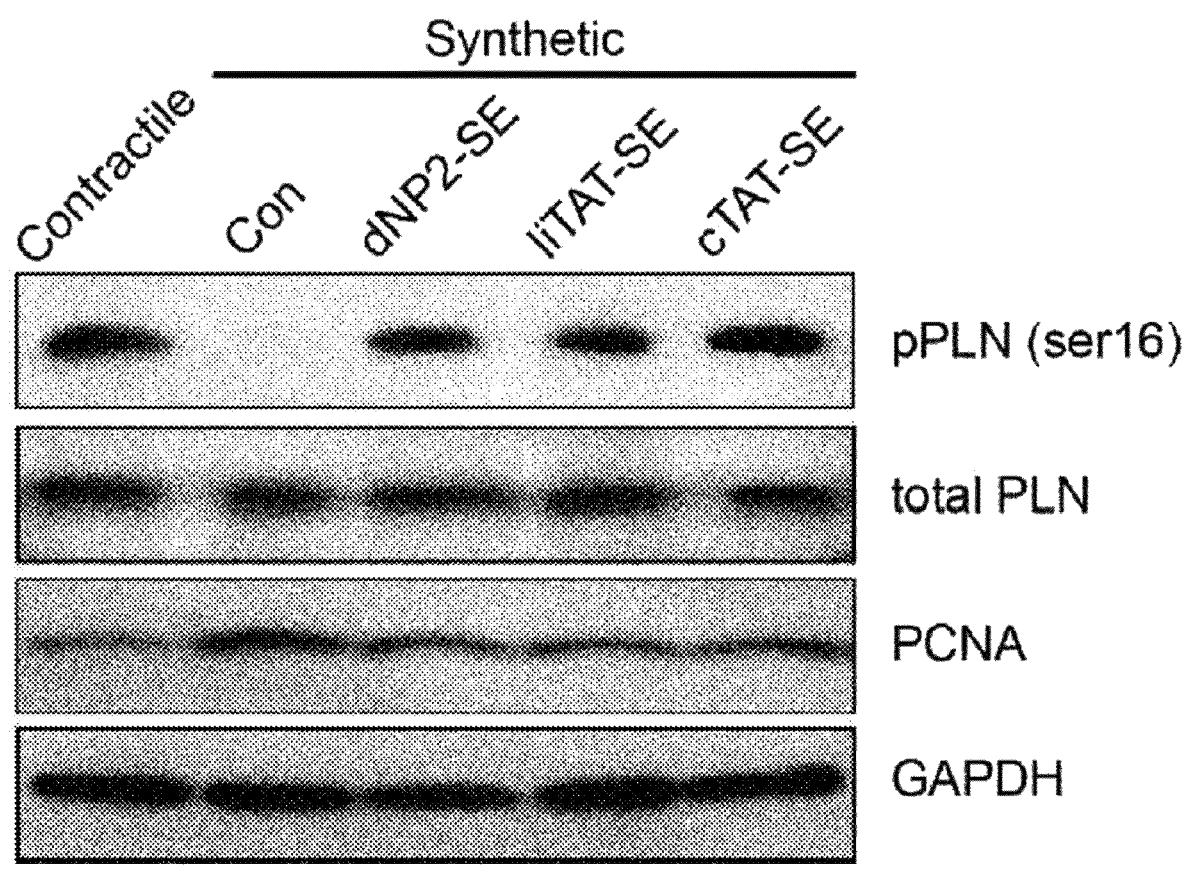

The cell penetrating peptide, which is a kind of signal peptide, is an amino acid combined peptide used for the purpose of delivering a substance, such as a protein or DNA, into cells. The present inventors established the previous therapeutic effects using dNP2, a human-derived sequence CPP. Besides, the present inventors diversified the kind and form of CPP by peptide cyclization as well as TAT, and compared such peptides with an existing peptide based on dND2 in view of effects. As a result, ψPLB-SE having sequences of linear TAT and cyclic TAT also increased the phosphorylation of eNOS and Akt in VECs (FIG. 20a), and increased the phosphorylation of PLB in VSMCs inducing a synthetic phenotype (FIG. 20b). These results indicate that the effects of ψPLB-SE are not restricted by the type and form of CPP.

Result Analysis and Further Discussion

Both pulmonary arterial hypertension (PAH) and restenosis shown after coronary artery intervention among the cardiovascular diseases are due to physical and pathological damages of VECs, and are ultimately diseases shown by the abnormal proliferation of vascular smooth muscle cells (VSMCs). These phenomena correspond to a wide concept and thus may be included in hypertension. The pulmonary arterial hypertension has been regarded as having no special medicine even 10 years ago. Although the life quality and survival time of patients have been increased through the development of many medicines resulting from the accumulation of many study results for many years, the pulmonary arterial hypertension has higher morbidity and mortality than other cardiovascular diseases. Studies have also been conducted in the absence of definitive therapy guidelines for restenosis not fully resolved.

Abnormal intracellular $Ca^{2+}$ handling resulting from a defect in sarco/endoplasmic reticulum (SR) function is one of main causes of cardiovascular disease [Lou Q et al. (2012) Adv Exp Med Biol 740: 1145-1174; Heijman J et al. (2012) Wien Med Wochenschr 162: 287-291]. Abnormal $Ca^{2+}$ uptake by SR is mainly due to a decrease in SERCA2a activity that can be caused by the expression and/or post-translational modification [Meyer M et al. (1995) Circulation 92: 778-784; Kho C et al. (2011) Nature 477: 601-605]. The gene transfer-mediated restoration of the SERCA2a level in cardiomyocytes is cardioprotective in mouse and pig models of heart failure [Miyamoto M I et al. (2000) Proc Natl Acad Sci USA 97: 793-798; Kawase Y et al (2008) J Am Coil Cardiol 51: 1112-1119; del Monte F et al. (2001) Circulation 104: 1424-1429]. In addition, SERCA2a gene transfer inhibits VSMC proliferation and neointimal growth in balloon-induced injury models. Therefore, SERCA2a can intervene in the treatment of vascular proliferative diseases including arterial restenosis and PAH.

SERCA2a activity is regulated by a series of signaling that involve inhibitor-1 (I-1), PP1, and phospholamban (PLB). I-1 binds to PP1 to inhibit PP1 to result in the elevation of PLB phosphorylation and SERCA2a activity. Therefore, the overexpression of continuously activated I-1

(I-1c) can restore SERCA2a activity in cardiomyocytes under various pathological insults [Nicolaou P et al. (2009) J Moll Cell Cardiol 47: 365-371]. In addition, I-1c gene transfer inhibits VSMC proliferation and neointimal formation by increasing SERCA2a activity. I-1c and SERCA2a gene transfer show a synergistic action [Lipskaia L et al. (2014) Cirucation 129: 773-785].

Figure 7:
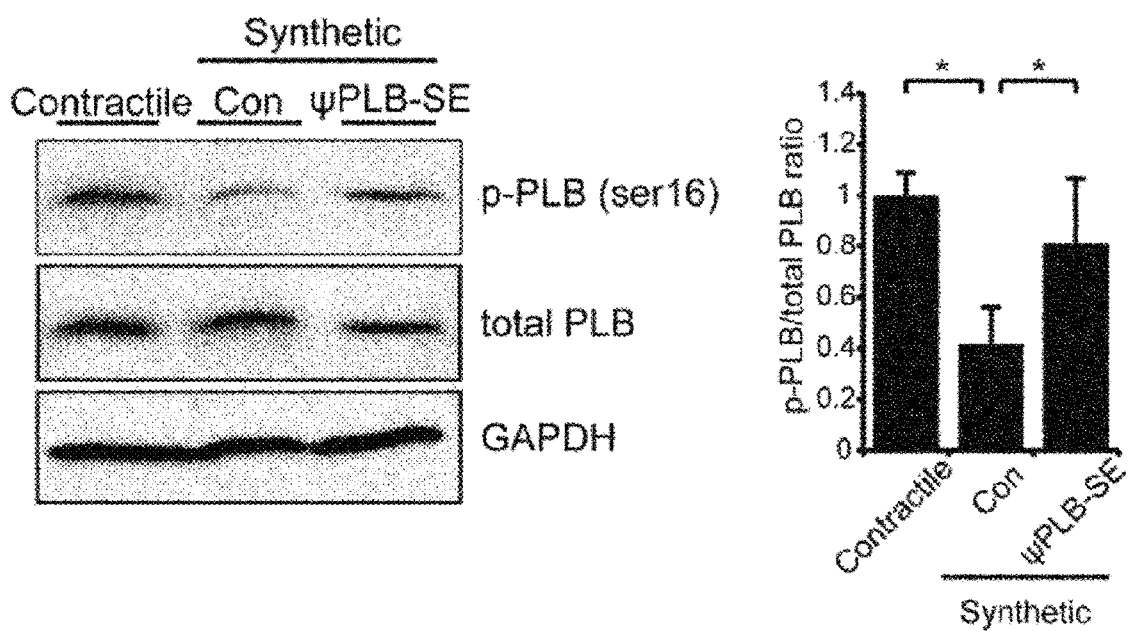
FIG. 7. ψPLB-SE attenuates PLB dephosphorylation in VSMCs. The proteins samples shown in FIG. 2C were subjected to western blotting. Antibodies against PLB or phospho-PLB were used. Data are expressed as the means±SD (n=3-4; *, P<0.05).

The present inventors showed in the previous studies that ψPLB-SE, a 9-mer peptide, targets PP1 and inhibits PLB dephosphorylation, leading to an increase in SERCA2a activity in cardiomyocytes. Similarly, ψPLB-SE inhibited the dephosphorylation of PLB even in RASMCs and PASMCs (see FIGS. 7, 18a, and 20b in the present specification).

In the present invention, the present inventors showed that ψPLB-SE inhibited VSMC proliferation and neointimal formation by elevating the SERCA2a level in VSMCs under synthetic conditions. In previous studies, SERCA gene transfer restored the SERCA2a level, whereas I-1c gene transfer restored SERCA2a activity. Therefore, it was surprising that the targeting of PP1 by ψPLB-SE also restored the SERCA2a level. To explain these observations, the present invention proposes a model in which the SERCA2a level and activity are closely interrelated to each other. Under synthetic conditions, the increased cytosolic $Ca^{2+}$ level may activate calpain to degrade the SERCA2a protein, and the decreased SERCA2a level may further increase the cytosolic $Ca^{2+}$ level. The data in the present invention show that the vicious cycle of cytosolic $Ca^{2+}$ increase and SERCA2a reduction can be interrupted by targeting PP1. By targeting PPI with ψPLB-SE, the increased SERCA2a activity may further decrease the cytosolic $Ca^{2+}$ level, thus attenuate the calpain-mediated SERCA2a degradation, thereby increasing the SERCA2a level.

Meanwhile, in the function of modulating vascular relaxation/tone, which corresponds to an important role of vascular endothelial cells, the production of NO as a vascular relaxant has a proliferation inhibitory effect. In pulmonary arterial hypertension, the reduced NO production is due to the decreased activity of eNOS, and the activation of eNOS is not sufficient to explain only by the regulation of intracellular calcium concentration through SERCA2a. There are a calcium-dependent pathway and a calcium-independent pathway in the activation pathway of eNOS [Zhao Y et al. (2015) J Pharmacol Sci 129(2): 83-94]. The calcium-independent pathway is made by regulating the phosphorylation of eNOS through by transduction of higher-order signals, such as Akt, AMPK, CamKII, and PKA. The resultant NO may also affect VSMCs to increase the activity of cGMP-dependent protein kinase, thereby lowering intracellular calcium [Blatter L A et al. (1994) Cell Calcium 15(2): 122-131]. The studies until the present have been fundamentally proceeding in a direction of maximizing the production or role of NO by eNOS gene transfer on the basis of endothelial precursor cells (EPCs), cGMP synthase activator (riociguat), cGMP hydrolysis inhibitor (Sildenafil), or the like [Prior D L et al. (2016) Med J Aust 205(6): 271-276; Granton J et al (2015) Circ Res 117(7): 645-654]. In the present invention, by presenting the PP1-Akt-eNOS signaling mechanism as well as the mechanism in which ψPLB-SE targets phospholamban, verified in the previously studies, it was verified that ψPLB-SE can not only inhibit the proliferation of VSMCs but also restore the dysfunction of VECs in charge of all vascular functions. It was verified that ψPLB-SE inhibits the interactions with PP1 and Akt to prevent Akt dephosphorylation, and thus regulates eNOS activity.

In addition, in the present invention, among features shown as phenotypes, the effect of inhibiting abnormal proliferation of VSMCs, shown in the blood vessels of rat and mouse pulmonary arterial hypertension models and the effect of reducing vascular fibrosis, shown from Masson's trichrome staining results and the normalization of the expression levels of genes, such as Collagen I and TGF-β, show the possibility that ψPLB-SE can potentially expect a therapeutic effect of hypertension.

Consequentially, the present invention verified that targeting PP1 with ψPLB-SE restored SERCA2a level and activity in VSMCs under synthetic conditions, and increased eNOS activity of VECs in pulmonary arterial hypertension. Therefore, ψPLB-SE can be a basis for a therapeutic strategy for vascular proliferative diseases and ψPLB-SE, as a peptide, may also have other advantages over gene therapies.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for treatment of hypertensive pulmonary disease, the method comprising administering a pharmaceutical composition to a subject, the composition comprising: (a) a pharmaceutically effective amount of a protein phosphatase 1 inhibitory peptide; and (b) a pharmaceutically acceptable carrier,
wherein the protein phosphatase 1 inhibitory peptide consists of an amino acid sequence selected from the group consisting of amino acid sequences of SEQ ID NO:2 to SEQ ID NO:6,
wherein a cell penetrating peptide (CPP) derived from human proteins is additionally bound to the protein phosphatase 1 inhibitory peptide.

2. The method of claim 1, wherein the protein phosphatase 1 inhibitory peptide is the amino acid sequence of SEQ ID NO: 2 or SEQ ID NO: 3.

3. The method of claim 1, wherein the pharmaceutical composition is administered orally or parenterally.

4. The method of claim 3, wherein the parenteral administration is intravenous injection, subcutaneous injection, intra-muscular injection, intraperitoneal injection, transdermal administration, nasal administration, or airway inhalation.

5. A method for mitigation or alleviation of hypertensive pulmonary disease, the method comprising administering a food composition to a subject, the composition comprising a protein phosphatase 1 inhibitory peptide,
wherein the protein phosphatase 1 inhibitory peptide consists of an amino acid sequence selected from the group consisting of amino acid sequences of SEQ ID NO:2 to SEQ ID NO:6,
wherein a cell penetrating peptide (CPP) derived from human proteins is additionally bound to the protein phosphatase 1 inhibitory peptide.

* * * * *

SEQUENCE LISTING

```
<160> NUMBER OF SEQ ID NOS: 23

<210> SEQ ID NO 1
<211> LENGTH: 52
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: 16Ser - phosphorylation

<400> SEQUENCE: 1

Met Glu Lys Val Gln Tyr Leu Thr Arg Ser Ala Ile Arg Arg Ala Ser
1               5                   10                  15

Thr Ile Glu Met Pro Gln Gln Ala Arg Gln Lys Leu Gln Asn Leu Phe
            20                  25                  30
```

Ile Asn Phe Cys Leu Ile Leu Ile Cys Leu Leu Ile Cys Ile Ile
        35                  40                  45

Val Met Leu Leu
    50

<210> SEQ ID NO 2
<211> LENGTH: 9
<212> TYPE: PRT
<213> ORGANISM: Artificial Sequence
<220> FEATURE:
<223> OTHER INFORMATION: protein phosphatase 1 inhibitory peptide

<400> SEQUENCE: 2

Arg Ala Glu Thr Ile Glu Met Pro Gln
1               5

<210> SEQ ID NO 3
<211> LENGTH: 9
<212> TYPE: PRT
<213> ORGANISM: Artificial Sequence
<220> FEATURE:
<223> OTHER INFORMATION: protein phosphatase 1 inhibitory peptide

<400> SEQUENCE: 3

Arg Ala Asp Thr Ile Glu Met Pro Gln
1               5

<210> SEQ ID NO 4
<211> LENGTH: 8
<212> TYPE: PRT
<213> ORGANISM: Artificial Sequence
<220> FEATURE:
<223> OTHER INFORMATION: protein phosphatase 1 inhibitory peptide

<400> SEQUENCE: 4

Ala Glu Thr Ile Glu Met Pro Gln
1               5

<210> SEQ ID NO 5
<211> LENGTH: 7
<212> TYPE: PRT
<213> ORGANISM: Artificial Sequence
<220> FEATURE:
<223> OTHER INFORMATION: protein phosphatase 1 inhibitory peptide

<400> SEQUENCE: 5

Arg Ala Glu Thr Ile Glu Met
1               5

<210> SEQ ID NO 6
<211> LENGTH: 6
<212> TYPE: PRT
<213> ORGANISM: Artificial Sequence
<220> FEATURE:
<223> OTHER INFORMATION: protein phosphatase 1 inhibitory peptide

<400> SEQUENCE: 6

Arg Ala Glu Thr Ile Glu
1               5

<210> SEQ ID NO 7
<211> LENGTH: 24
<212> TYPE: DNA
<213> ORGANISM: Artificial Sequence
<220> FEATURE:
<223> OTHER INFORMATION: mouse TGF-b 1 F primer

```
<400> SEQUENCE: 7
caacaattcc tggcgttacc ttgg                                          24

<210> SEQ ID NO 8
<211> LENGTH: 24
<212> TYPE: DNA
<213> ORGANISM: Artificial Sequence
<220> FEATURE:
<223> OTHER INFORMATION: mouse TGF-b 1 R primer

<400> SEQUENCE: 8
gaaagccctg tattccgtct cctt                                          24

<210> SEQ ID NO 9
<211> LENGTH: 21
<212> TYPE: DNA
<213> ORGANISM: Artificial Sequence
<220> FEATURE:
<223> OTHER INFORMATION: mouse Collagen 1 F-primer

<400> SEQUENCE: 9
cccaaggaaa agaagcacgt c                                             21

<210> SEQ ID NO 10
<211> LENGTH: 22
<212> TYPE: DNA
<213> ORGANISM: Artificial Sequence
<220> FEATURE:
<223> OTHER INFORMATION: mouse Collagen 1 R-primer

<400> SEQUENCE: 10
aggtcagctg gatagcgaca tc                                            22

<210> SEQ ID NO 11
<211> LENGTH: 15
<212> TYPE: DNA
<213> ORGANISM: Artificial Sequence
<220> FEATURE:
<223> OTHER INFORMATION: mouse a-SMA F primer

<400> SEQUENCE: 11
atcgtccacc gcaaa                                                    15

<210> SEQ ID NO 12
<211> LENGTH: 18
<212> TYPE: DNA
<213> ORGANISM: Artificial Sequence
<220> FEATURE:
<223> OTHER INFORMATION: mouse a-SMA R primer

<400> SEQUENCE: 12
aaggaactgg aggcgctg                                                 18

<210> SEQ ID NO 13
<211> LENGTH: 24
<212> TYPE: DNA
<213> ORGANISM: Artificial Sequence
<220> FEATURE:
<223> OTHER INFORMATION: mouse IL-1b F primer

<400> SEQUENCE: 13
caaccaacaa gtgatattct ccat                                          24

<210> SEQ ID NO 14
```

```
<211> LENGTH: 21
<212> TYPE: DNA
<213> ORGANISM: Artificial Sequence
<220> FEATURE:
<223> OTHER INFORMATION: mouse IL-1b R primer

<400> SEQUENCE: 14
gatccacact ctccagctgc a                                               21

<210> SEQ ID NO 15
<211> LENGTH: 25
<212> TYPE: DNA
<213> ORGANISM: Artificial Sequence
<220> FEATURE:
<223> OTHER INFORMATION: mouse TNF-a F primer

<400> SEQUENCE: 15
catcttctca aaattcgagt gacaa                                           25

<210> SEQ ID NO 16
<211> LENGTH: 23
<212> TYPE: DNA
<213> ORGANISM: Artificial Sequence
<220> FEATURE:
<223> OTHER INFORMATION: mouse TNF-a R primer

<400> SEQUENCE: 16
tgggagtaga caaggtacaa ccc                                             23

<210> SEQ ID NO 17
<211> LENGTH: 21
<212> TYPE: DNA
<213> ORGANISM: Artificial Sequence
<220> FEATURE:
<223> OTHER INFORMATION: mouse F4/80 F-primer

<400> SEQUENCE: 17
cttggctatg ggcttccagt c                                               21

<210> SEQ ID NO 18
<211> LENGTH: 24
<212> TYPE: DNA
<213> ORGANISM: Artificial Sequence
<220> FEATURE:
<223> OTHER INFORMATION: mouse F4/80 R-primer

<400> SEQUENCE: 18
gcaaggagga cagagtttat cgtg                                            24

<210> SEQ ID NO 19
<211> LENGTH: 20
<212> TYPE: DNA
<213> ORGANISM: Artificial Sequence
<220> FEATURE:
<223> OTHER INFORMATION: mouse MCP1 F primer

<400> SEQUENCE: 19
gctcagccag atgcagttaa                                                 20

<210> SEQ ID NO 20
<211> LENGTH: 23
<212> TYPE: DNA
<213> ORGANISM: Artificial Sequence
<220> FEATURE:
<223> OTHER INFORMATION: mouse MCP1 R primer

<400> SEQUENCE: 20
```

```
tcttgagctt ggtgacaaaa act                                          23
```

```
<210> SEQ ID NO 21
<211> LENGTH: 24
<212> TYPE: PRT
<213> ORGANISM: Artificial Sequence
<220> FEATURE:
<223> OTHER INFORMATION: dNP2

<400> SEQUENCE: 21

Lys Ile Lys Lys Val Lys Lys Lys Gly Arg Lys Gly Ser Lys Ile Lys
1               5                   10                  15

Lys Val Lys Lys Lys Gly Arg Lys
            20

<210> SEQ ID NO 22
<211> LENGTH: 11
<212> TYPE: PRT
<213> ORGANISM: Artificial Sequence
<220> FEATURE:
<223> OTHER INFORMATION: TAT

<400> SEQUENCE: 22

Tyr Gly Arg Lys Lys Arg Arg Gln Arg Arg Arg
1               5                   10

<210> SEQ ID NO 23
<211> LENGTH: 9
<212> TYPE: PRT
<213> ORGANISM: Artificial Sequence
<220> FEATURE:
<223> OTHER INFORMATION: wild type peptide
<220> FEATURE:
<221> NAME/KEY: MISC_FEATURE
<222> LOCATION: (3)..(3)
<223> OTHER INFORMATION: 3Ser - phosphorylation

<400> SEQUENCE: 23

Arg Ala Ser Thr Ile Glu Met Pro Gln
1               5
```